US006489354B1

United States Patent
Bao et al.

(10) Patent No.: US 6,489,354 B1
(45) Date of Patent: *Dec. 3, 2002

(54) 3-ALKYL SUBSTITUTED PYRROLIDINE MODULATORS OF CHEMOKINE RECEPTOR ACTIVITY

(75) Inventors: Jianming Bao, Scotch Plains, NJ (US); Robert K. Baker, Cranford, NJ (US); William H. Parsons, Edison, NJ (US); Kathleen Rupprecht, Cranford, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/516,771

(22) Filed: Mar. 1, 2000

Related U.S. Application Data

(60) Provisional application No. 60/122,575, filed on Mar. 2, 1999.

(51) Int. Cl.[7] .................. A61K 31/40; A61K 31/33; C07D 401/00; C07D 403/00; C07D 409/00
(52) U.S. Cl. ............ 514/422; 514/210.16; 514/210.19; 514/210.2; 514/215; 514/217.02; 514/217.03; 514/217.08; 514/235.5; 514/252.13; 514/253.09; 514/278; 514/309; 514/319; 514/323; 514/326; 514/336; 514/339; 514/343; 514/366; 514/408; 514/409; 514/410; 514/414; 514/443; 540/595; 540/602; 544/129; 544/372; 546/16; 546/17; 546/200; 546/208; 546/209; 546/276.4; 546/277.4; 546/279.7; 548/416; 548/517; 548/565; 548/950
(58) Field of Search .................. 514/236.5, 278, 514/309, 323, 326, 336, 343, 339, 408, 409, 410, 414, 422, 210.16, 210.19, 210.2, 215, 217.02, 217.03, 217.08, 252.13, 253.09, 319, 366, 443; 540/595, 602; 544/129, 372; 546/16, 17, 200, 208, 209, 276.4, 277.4, 279.7; 548/416, 517, 565, 960

(56) References Cited

U.S. PATENT DOCUMENTS

| | | | |
|---|---|---|---|
| 5,217,967 A | 6/1993 | Lehr et al. ............ | 514/217 |
| 5,541,343 A | 7/1996 | Himmelsbach et al. .... | 514/424 |
| 5,998,444 A | 12/1999 | Russell et al. .......... | 514/331 |
| 6,136,827 A | 10/2000 | Caldwell et al. ........ | 514/329 |
| 6,140,349 A | 10/2000 | Caldwell et al. ........ | 514/326 |
| 6,166,037 A | 12/2000 | Budhu et al. ........... | 514/326 |
| 6,362,201 B1 * | 3/2002 | Baker et al. ........... | 514/326 |
| 6,372,754 B1 * | 4/2002 | Bao et al. ............. | 514/326 |

FOREIGN PATENT DOCUMENTS

| | | |
|---|---|---|
| EP | 0 136 658 | 9/1984 |
| JP | 10-273489 | 10/1998 |
| WO | WO00/51607 | 9/2000 |
| WO | WO00/51608 | 9/2000 |
| WO | WO00/51609 | 9/2000 |
| WO | WO00/51610 | 9/2000 |

OTHER PUBLICATIONS

STN/CAS online, file CAPLUS, Acc. No. 1996:351172, Doc. No. 125:31527 (Cohen et al., Am. J. Clin. Pathol. (1996), 105 (5), 589–598), Abstract.*
STN/CAS online, file CAPLUS, Acc. No. 2000:644858, Doc. No. 133:329677 (Hatina et al., Cesk. Fyziol. (2000), 49(3), 99–115), Abstract.*
STN/CAS online, file CANCERLIT, Acc. No. 1998078461, Doc. No. 98078461 (Cohen et al., Immunological Reviews (1997), vol. 159, pp. 31–48), Abstract.*
Wiedermann, et al, CA 1989: 546934 (Naunyn–Schmiedeburg's Arch. Pharmacol., vol. 340, No. 2, pp. 185–190, 1989).
Gerard, C., CA 1999:391992 (Contem. Cancer Res., vol. 4, pp. 21–31, 1999).

* cited by examiner

Primary Examiner—Jose' G. Dees
Assistant Examiner—Frank Choi
(74) Attorney, Agent, or Firm—Mollie M. Yang; David L. Rose; J. Eric Thies

(57) ABSTRACT

The present invention is directed to pyrrolidine compounds of the formula I:

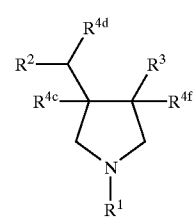

(wherein $R^1$, $R^2$, $R^3$, $R^{4c}$, $R^{4d}$, and $R^{4f}$ are defined herein) which are useful as modulators of chemokine receptor activity. In particular, these compounds are useful as modulators of the chemokine receptors CCR-3 and/or CCR-5.

16 Claims, No Drawings

3-ALKYL SUBSTITUTED PYRROLIDINE MODULATORS OF CHEMOKINE RECEPTOR ACTIVITY

CROSS REFERENCE TO RELATED APPLICATIONS

This application claims priority under 35 U.S.C. 119(e) from Provisional Application No. 60/122,575, filed Mar. 2, 1999.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, Cytokine, 3, 165–183 (1991) and Murphy, Rev. Immun., 12, 593–633 (1994)). These are two classes of chemokines, C-X-C (α) and C-C (β), depending on whether the first two cysteines are separated by a single amino acid (C-X-C) or are adjacent (C-C). The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, T-cells, eosinophils and basophils (Deng, et al., Nature, 381, 661–666 (1996)).

The chemokines bind specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., J. Biol. Chem., 270, 22123–22128 (1995); Beote, et al, Cell, 72, 414–415 (1993)); CCR-2A and CCR-2B (or "CKR-2A"/"CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., J. Biol. Chem., 270, 16491–16494 (1995); CCR-4 (or "CKR-4" or "CC-CKR-4") [MIP-1α, RANTES, MCP-1] (Power, et al., J. Biol. Chem., 270, 19495–19500 (1995)); CCR-5 (or "CKR-5" or "CC-CKR-5") [MIP-1α, RANTES, MIP-1β] (Sanson, et al., Biochemistry, 35, 3362–3367 (1996)); and the Duffy blood-group antigen [RANTES, MCP-1] (Chaudhun, et al., J. Biol. Chem., 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., J. Exp. Med. 183, 2421–2426 (1996). An antagonist of the CCR3 receptor, Met-chemokine beta 7, has been proposed to be useful in ameliorating leukocyte infiltration associated with allergic inflammation (Nibbs, et al., J. Immunol., 164, 1488–1497 (2000)). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., Science, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require the chemokine receptors CCR-5 and CXCR-4, as well as the primary receptor CD4 (Levy, N. Engl. J. Med., 335(20), 1528–1530 (Nov. 14, 1996). The principal cofactor for entry mediated by the envelope glycoproteins of primary macrophage-trophic strains of HIV-1 is CCR5, a receptor for the β-chemokines RANTES, MIP-1α and MIP-1β (Deng, et al., Nature, 381, 661–666 (1996)), HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that β-chemokine ligands prevent HIV-1 from fusing with the cell (Dragic, et al., Nature, 381, 667–673 (1996)). It has further been demonstrated that a complex of gp120and soluble CD4 interacts specifically with CCR-5 and inhibits the binding of the natural CCR-5 ligands MIP-1α and MIP-1β (Wu, et al., Nature, 384, 179–183 (1996); Trkola, et al., Nature, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (Nature, 382, 722–725 (1996)). Absence of CCR-5 appears to confer protection from HIV-1 infection (Nature, 382, 668–669 (1966)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (Nature Medicine, 2(11), 1240–1243 (1996)). Nevertheless, drugs targeting chemokine receptors may not be unduly compromised by the genetic diversity of HIV-1

(Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

SUMMARY OF THE INVENTION

The present invention is directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

The present invention is further concerned with compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection of HIV.

DETAILED DESCRIPTION OF THE INVENTION

The present invention is directed to compounds of formula I:

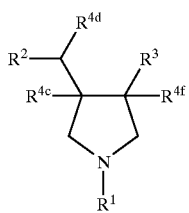

I wherein
$R^1$ is —X—$R^8$, wherein X is selected from the group consisting of:
(1) —$CH_2$—,
(2) —CO—,
(3) —$CH_2CH_2$—,
(4) —$CH_2CH_2CH_2$—, and
(5) —CH($C_{1-6}$alkyl)—,
and wherein $R^8$ is a selected from:
phenyl, naphthyl, biphenyl, fluorenyl, indenyl, indanyl, dihydronaphthyl, tetrahydronaphthyl, octahydronaphthyl, adamantyl, and heterocycle, which may be unsubstituted or substituted, where the substituents are independently selected from:
(a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
(A) phenyl, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —NH($C_{1-6}$ alkyl), —N($C_{1-6}$ alkyl)($C_{1-6}$ alkyl), or trifluoromethyl,
(B) naphthyl, unsubstituted or substituted, wherein the substituents are independently selected from: halogen hydroxy, $C_{1-6}$alkyl, $C_{1-6}$alkoxy, —$CO_2(C_{1-6}$ alkyl), —$NH_2$, —NH ($C_{1-6}$ alkyl), —N($C_{1-6}$ alkyl)($C_{1-6}$ alkyl, or trifluoromethyl,
(C) heterocycle, unsubstituted or substituted, wherein the substituents are independently selected from: halogen, hydroxy, $C_{1-6}$alkyl, $C_{1-6}$alkoxy, —$CO_2(C_{1-6}$ alkyl), —$NH_2$, —NH ($C_{1-6}$ alkyl), —N($C_{1-6}$ alkyl)($C_{1-6}$ alkyl), or trifluoromethyl,
(D) hydroxy,
(E) —O($C_{1-6}$ alkyl),
(F) —$CO_2(C_{1-6}$ alkyl),
(G) —S(O)$_n$—($C_{1-6}$ alkyl), wherein n is an integer selected from 0, 1 and 2,
(H) halogen,
(I) —$NH_2$,
(J) —NH($C_{1-6}$ alkyl), and
(K) —N($C_{1-6}$ alkyl)($C_{1-6}$ alkyl),
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9CO$—$NR^9R^{10}$,
(ix) —$S(O)_2$—$NR^9R^{10}$, wherein n is an integer selected from 0, 1 and 2,
(x) —$NR^9S(O)_2$—$R^{10}$,
(xi) —$NR^9S(O)_2$—$NR^9R^{10}$,
(xii) —$S(O)_n$—$R^9$,
(xiii) —$CF_3$,
(xiv) —$CHF_2$,
(xv) —$CH_2F$,
(xvi) —O—$R^9$,
(xvii) —O($C_{1-6}$ alkyl)—O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$, (xxix) —OCO$_2$—R$^9$, and
(xxx) —CO—R$^9$,
(b) —O—C$_{1-6}$alkyl, —O—C$_{2-6}$ alkenyl, —O—C$_{2-6}$ alkynyl, wherein the alkyl, alkenyl, or alkynyl is unsubstituted or substituted, wherein the substituents are independently selected from:
(i) hydroxy,
(ii) halogen,
(iii) —NR$^9$R$^{10}$,
(iv) —NR$^9$—COR$^{10}$,
(v) —NR$^9$—CO$_2$R$^{10}$,
(vi) —CO—NR$^9$R$^{10}$,
(vii) —OCO—NR$^9$R$^{10}$,
(viii) —NR$^9$CO—NR$^9$R$^{10}$,
(ix) —S(O)$_2$—NR$^9$R$^{10}$,
(x) —NR$^9$S(O)$_2$—R$^{10}$,
(xi) —NR$^9$S(O)$_2$—NR$^9$R$^{10}$,
(xii) —S(O)$_n$—R$^9$,
(xiii) —CF$_3$,
(xiv) —CHF$_2$,
(xv) —CH$_2$F,
(xvii) —O—R$^9$,
(xvii) —O(C$_{1-6}$ alkyl)—O—R$^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—R$^9$,
(xxix) —OCO$_2$—R$^9$, and
(xxx) —CO—R$^9$,
(c) —NO$_2$,
(d) hydroxy,
(e) halogen,
(f) —NR$^9$R$^{10}$,
(g) —NR$^9$—COR$^{10}$,
(h) —NR$^9$—CO$_2$R$^{10}$,
(i) —CO—NR$^9$R$^{10}$,
(j) —OCO—NR$^9$R$^{10}$,
(k) —NR$^9$CO—NR$^9$R$^{10}$,
(l) —S(O)$_2$—NR$^9$R$^{10}$,
(m) —NR$^9$S(O)$_2$—R$^{10}$,
(n) —NR$^9$S(O)$_2$—NR$^9$R$^{10}$,
(o) —S(O)$_n$—R$^9$,
(p) —CF$_3$,
(q) —CHF$_2$,
(r) —CH$_2$F,
(s) —OCO—R$^9$,
(t) —OCO$_2$—R$^9$, and
(u) —CO—R$^9$;

R$^2$ is selected from the group consisting of:

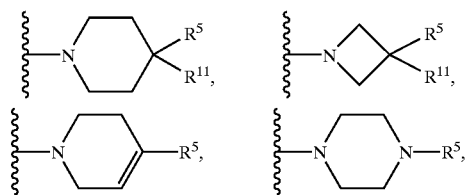

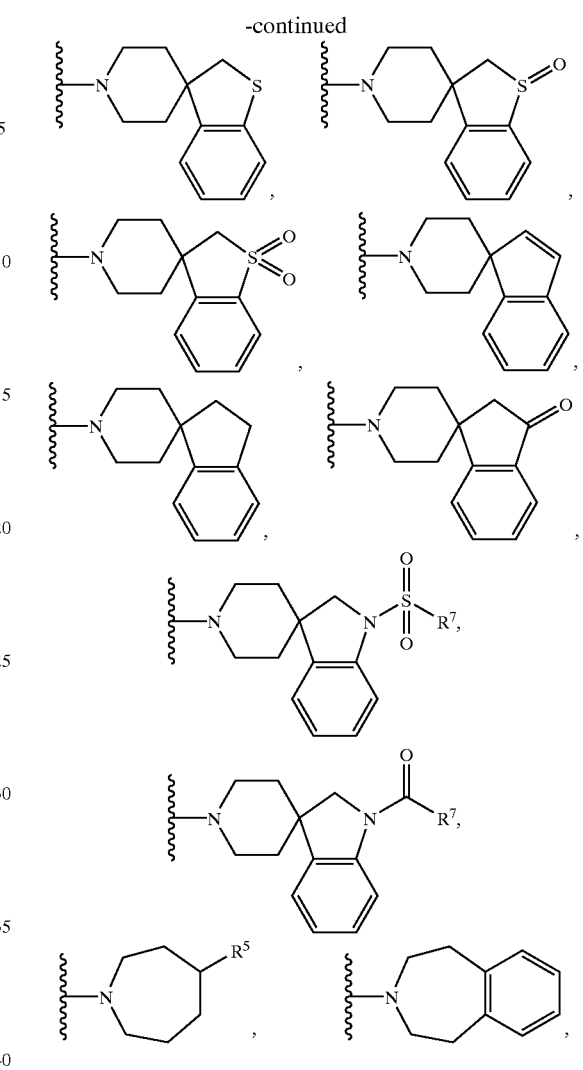

wherein R$^5$ is a selected from:
(1) —NR$^6$CO—O—R$^7$, wherein R$^6$ is hydrogen, C$_{1-6}$ alkyl or C$_{1-6}$ alkyl—C$_{5-6}$ cycloalkyl, and R$^7$ is C$_{1-6}$ alkyl, C$_{5-6}$ cycloalkyl, benzyl, or phenyl, wherein the alkyl, cycloalkyl, benzyl or phenyl is unsubstituted or substituted with halogen, C$_{1-3}$alkyl, C$_{1-3}$alkoxy or trifluoromethyl,
(2) phenyl, which is unsubstituted or substituted with halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl,
(3) -pyridyl,
(4) -thienyl,
(5) —C$_{1-6}$alkyl-phenyl, —C$_{1-6}$alkyl-naphthyl, —C$_{1-6}$alkyl-indenyl, —C$_{1-6}$alkyl-indanyl, and —C$_{1-6}$alkyl-heterocycle, wherein the phenyl, naphthyl, indenyl, indanyl, or heterocycle is unsubstituted or substituted with: halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl; and wherein the —C$_{1-6}$alkyl is optionally substituted with oxo, hydroxy, C$_{1-6}$alkoxy, acetoxy, or halogen,
(6) —O—C$_{1-6}$alkyl-phenyl, —O—C$_{1-6}$alkyl-naphthyl, —O—C$_{1-6}$alkyl-indenyl, —O—C$_{1-6}$alkyl-indanyl, and —O—C$_{1-6}$alkyl-heterocycle, wherein the phenyl, naphthyl, indenyl, indanyl., or heterocycle is unsubstituted or substituted with: halogen, hydroxy, $C_{1-6}$alkyl, $C_{1-6}$alkoxy, $-CO_2(C_{1-6}$ alkyl), $-NH_2$, $-NHR^9$, $-NR^9R^{10}$, or trifluoromethyl, (7) $-C_{1-4}$alkyl$-O-C_{1-4}$alkyl-phenyl, wherein the phenyl is unsubstituted or substituted with halogen, hydroxy, $C_{1-6}$alkyl, $C_{1-6}$alkoxy, $-CO_2(C_{1-6}$ alkyl), $-NH_2$, $-NHR^9$, $-NR^9R^{10}$, or trifluoromethyl, and (8) $-C_{1-4}$alkyl-$S(O)_n-C_{1-4}$alkyl-phenyl, wherein the phenyl is unsubstituted or substituted with halogen, hydroxy, $C_{1-6}$alkyl, $C_{1-6}$alkoxy, $-CO_2(C_{1-6}$ alkyl), $-NH_2$, $-NHR^9$, $-NR^9R^{10}$, or trifluoromethyl;

and wherein $R^{11}$ is a selected from:
(1) -hydrogen,
(2) $-OH$,
(3) $-C_{1-6}$alkyl, and
(4) -halogen;

$R^3$ is selected from:
$C_{1-8}$ alkyl, $C_{2-8}$ alkenyl, and $C_{2-8}$ alkynyl, wherein the alkyl, alkenyl, or alkynyl is unsubstituted or substituted, wherein the substituents are independently selected from:
(a) halogen,
(b) hydroxy,
(c) $-CO_2(C_{1-6}$ alkyl),
(d) $-OCO-R^9$,
(e) $-OCO_2-R^9$,
(f) $-CO-R^9$,
(g) phenyl or heterocycle, wherein the phenyl or heterocycle is unsubstituted or substituted, wherein the substituents are independently selected from: halogen, hydroxy, $C_{1-6}$alkyl, $C_{1-6}$alkoxy, $-CO_2(C_{1-6}$ alkyl), $-NR^9R^{10}$, or trifluoromethyl;
(h) $-S(O)_n-R^9$,
(i) $-NR^9R^{10}$,
(j) $-NR^9-COR^{10}$,
(k) $-NR^9-CO_2R^{10}$,
(l) $-CO-NR^9R^{10}$,
(m) $-OCO-NR^9R^{10}$,
(n) $-NR^9CO-NR^9R^{10}$,
(o) $-S(O)_2-NR^9R^{10}$,
(p) $-NR^9S(O)_2-R^{10}$,
(q) $-NR^9S(O)_2-NR^9R^{10}$,
(r) $-CF_3$,
(s) $-CHF_2$,
(t) $-CH_2F$, and
(u) $-O-R^9$;

$R^{4c}$, $R^{4d}$, and $R^{4f}$ are independently selected from the group consisting of:
(1) hydrogen, and
(2) $C_{1-6}$ alkyl;
and pharmaceutically acceptable salts thereof and individual diastereomers thereof.

Preferred compounds of the present invention include those of formula Ia:

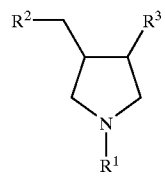

Ia wherein:
$R^1$, $R^2$ and $R^3$ are defined herein; and pharmaceutically acceptable salts and individual diastereomers thereof.

Preferred compounds of the present invention include those of the formula Ib:

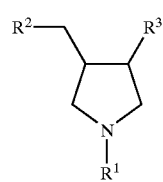

Ib wherein:
$R^1$ is $-X-R^8$, wherein X is selected from the group consisting of:
(1) $-CH_2-$,
(2) $-CO-$, and
(3) $-CH_2CH_2-$, and wherein $R^8$ is a selected from:
phenyl, naphthyl, biphenyl, fluorenyl, indenyl, indanyl, dihydronaphthyl, tetrahydronaphthyl, octahydronaphthyl, adamantyl, and heterocycle, which may be unsubstituted or substituted, where the substituents are independently selected from:
(a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
(i) hydroxy,
(ii) halogen,
(iii) $-NR^9R^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
(A) phenyl unsubstituted or substituted, wherein the substituents are independently selected from: halogen, hydroxy, $C_{1-6}$alkyl, $C_{1-6}$alkoxy, $-CO_2(C_{1-6}$ alkyl), $-NH_2$, $-NH(C_{1-6}$ alkyl), $-N(C_{1-6}$ alkyl)($C_{1-6}$ alkyl), or trifluoromethyl,
(B) naphthyl, unsubstituted or substituted, wherein the substituents are independently selected from: halogen, hydroxy, $C_{1-6}$alkyl, $C_{1-6}$alkoxy, $-CO_2(C_{1-6}$ alkyl), $-NH_2$, $-NH(C_{1-6}$ alkyl), $-N(C_{1-6}$ alkyl)($C_{1-6}$ alkyl), or trifluoromethyl,
(C) heterocycle, unsubstituted or substituted, wherein the substituents are independently selected from: halogen, hydroxy, $C_{1-6}$alkyl, $C_{1-6}$alkoxy, $-CO_2(C_{1-6}$ alkyl), $-NH_2$, $-NH(C_{1-6}$ alkyl), $-N(C_{1-6}$ alkyl)($C_{1-6}$ alkyl), or trifluoromethyl,
(D) hydroxy,
(E) $-O(C_{1-6}$ alkyl),
(F) $-CO_2(C_{1-6}$ alkyl),
(G) $-S(O)_n-(C_{1-6}$ alkyl), wherein n is an integer selected from 0, 1 and 2,
(H) halogen,
(I) $-NH_2$,
(J) $-NH(C_{1-6}$ alkyl), and
(K) $-N(C_{1-6}$ alkyl)($C_{1-6}$ alkyl),
(iv) $-NR^9-COR^{10}$,
(v) $-NR^9-CO_2R^{10}$,
(vi) $-CO-NR^9R^{10}$,
(vii) $-OCO-NR^9R^{10}$,
(viii) $-NR^9CO-NR^9R^{10}$, (ix) —S(O)$_2$—NR$^9$R$^{10}$, wherein n is an integer selected from 0, 1 and 2,
(x) —NR$^9$S(O)$_2$—R$^{10}$,
(xi) —NR$^9$S(O)$_2$—NR$^9$R$^{10}$,
(xii) —S(O)$_n$—R$^9$,
(xiii) —CF$_3$,
(xiv) —CHF$_2$,
(xv) —CH$_2$F,
(xvi) —O—R$^9$,
(xvii) —O(C$_{1-6}$ alkyl)—O—R$^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—R$^9$,
(xxix) —OCO$_2$—R$^9$, and
(xxx) —CO—R$^9$,
(b) —O—C$_{1-6}$alkyl, —O—C$_{2-6}$ alkenyl, —O—C$_{2-6}$ alkynyl, wherein the alkyl, alkenyl, or alkynyl is unsubstituted or substituted, wherein the substituents are independently selected from:
(i) hydroxy,
(ii) halogen,
(iii) —NR$^9$R$^{10}$,
(iv) —NR$^9$—COR$^{10}$,
(v) —NR$^9$—CO$_2$R$^{10}$,
(vi) —CO—NR$^9$R$^{10}$,
(vii) —OCO—NR$^9$R$^{10}$,
(viii) —NR$^9$CO—NR$^9$R$^{10}$,
(ix) —S(O)$_2$—NR$^9$R$^{10}$,
(x) —NR$^9$S(O)$_2$—R$^{10}$,
(xi) —NR$^9$S(O)$_2$—NR$^9$R$^{10}$,
(xii) —S(O)$_n$—R$^9$,
(xiii) —CF$_3$,
(xiv) —CHF$_2$,
(xv) —CH$_2$F,
(xvii) —O—R$^9$,
(xvii) —O(C$_{1-6}$ alkyl)—O—R$^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—R$^9$,
(xxix) —OCO$_2$—R$^9$, and
(xxx) —CO—R$^9$,
(c) —NO$_2$,
(d) hydroxy,
(e) halogen,
(f) —NR$^9$R$^{10}$,
(g) —NR$^9$—COR$^{10}$,
(h) —NR$^9$—CO$_2$R$^{10}$,
(i) —CO—NR$^9$R$^{10}$,
(j) —OCO—NR$^9$R$^{10}$,
(k) —NR$^9$CO—NR$^9$R$^{10}$,
(l) —S(O)$_2$—NR$^9$R$^{10}$,
(m) —NR$^9$S(O)$_2$—R$^{10}$,
(n) —NR$^9$S(O)$_2$—NR$^9$R$^{10}$,
(o) —S(O)$_n$—R$^9$,
(p) —CF$_3$,
(q) —CHF$_2$,
(r) —CH$_2$F,
(s) —OCO—R$^9$,
(t) —OCO$_2$—R$^9$, and
(u) —CO—R$^9$;
R$^2$ is:

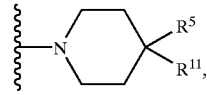

wherein R$^5$ is a selected from:
(1) —NR$^6$CO—O—R$^7$, wherein R$^6$ is hydrogen, C$_{1-6}$ alkyl or C$_{1-6}$ alkyl—C$_{5-6}$ cycloalkyl, and R$^7$ is C$_{1-6}$ alkyl, C$_{5-6}$ cycloalkyl, benzyl or phenyl, wherein the alkyl, cycloalkyl, benzyl or phenyl is unsubstituted or substituted with halogen, C$_{1-3}$alkyl, C$_{1-3}$alkoxy or trifluoromethyl,
(2) phenyl, which is unsubstituted or substituted with halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl,
(3) -pyridyl,
(4) -thienyl,
(5) —C$_{1-6}$alkyl-phenyl, —C$_{1-6}$alkyl-naphthyl, —C$_{1-6}$alkyl-indenyl, —C$_{1-6}$alkyl-indanyl, and —C$_{1-6}$alkyl-heterocycle, wherein the phenyl, naphthyl, indenyl, indanyl, or heterocycle is unsubstituted or substituted with: halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl; and wherein the —C$_{1-6}$alkyl is optionally substituted with oxo, hydroxy, C$_{1-6}$alkoxy, acetoxy, or halogen,
(6) —O—C$_{1-6}$alkyl-phenyl, —O—C$_{1-6}$alkyl-naphthyl, —O—C$_{1-6}$alkyl-indenyl, —O—C$_{1-6}$alkyl-indanyl, and —O—C$_{1-6}$alkyl-heterocycle, wherein the phenyl, naphthyl, indenyl, indanyl, or heterocycle is unsubstituted or substituted with: halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl,
(7) —C$_{1-4}$alkyl—O—C$_{1-4}$alkyl-phenyl, wherein the phenyl is unsubstituted or substituted with halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl, and
(8) —C$_{1-4}$alkyl—S(O)$_n$—C$_{1-4}$alkyl-phenyl, wherein the phenyl is unsubstituted or substituted with halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl;
and wherein R$^{11}$ is a selected from:
(1) -hydrogen,
(2) —OH,
(3) —C$_{1-6}$alkyl, and
(4) -halogen;
R$^3$ is selected from:
C$_{1-8}$ alkyl, C$_{2-8}$ alkenyl, and C$_{2-8}$ alkynyl, wherein the alkyl, alkenyl, or alkynyl is unsubstituted or substituted, wherein the substituents are independently selected from:
(a) halogen,
(b) hydroxy, (c) —CO$_2$(C$_{1-6}$ alkyl),
(d) —OCO—R$^9$,
(e) —OCO$_2$—R$^9$,
(f) —CO—R$^9$,
(g) phenyl or heterocycle, wherein the phenyl or heterocycle is unsubstituted or substituted, wherein the substituents are independently selected from: halogen, hydroxy, C$_{1-6}$alkyl, C$_{1-6}$alkoxy, —CO$_2$(C$_{1-6}$ alkyl), —NR$^9$R$^{10}$, or trifluoromethyl;
(h) —S(O)$_n$—R$^9$,
(i) —NR$^9$R$^{10}$,
(j) —NR$^9$—COR$^{10}$,
(k) —NR$^9$—CO$_2$R$^{10}$,
(l) —CO—NR$^9$R$^{10}$,
(m) —OCO—NR$^9$R$^{10}$,
(n) —NR$^9$CO—NR$^9$R$^{10}$,
(o) —S(O)$_2$—NR$^9$R$^{10}$,
(p) —NR$^9$S(O)$_2$—R$^{10}$,
(q) —NR$^9$S(O)$_2$—NR$^9$R$^{10}$,
(r) —CF$_3$,
(s) —CHF$_2$,
(t) —CH$_2$F, and
(u) —O—R$^9$;
and pharmaceutically acceptable salts thereof and individual diastereomers thereof.

More preferred compounds of the present invention include those of the formula Ic:

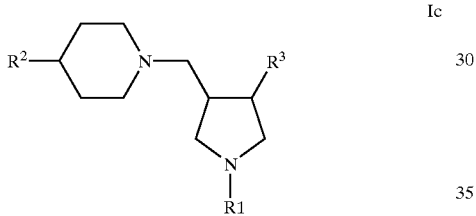

Ic wherein:
R$^1$, R$^5$, R$^{12}$, R$^{13}$, Y, Z and m are defined herein; and pharmaceutically acceptable salts and individual diastereomers thereof.

Highly preferred compounds of the present invention further include those of the formula Id:

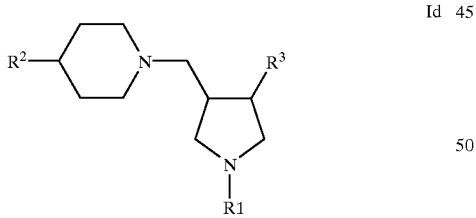

Id wherein:
R$^1$ is —X—R$^8$, wherein X is selected from the group consisting of:
(1) —CH$_2$—, and
(2) —CO—, and wherein R$^8$ is selected from: phenyl, naphthyl, indenyl, indanyl, indolyl, quinolyl, isoquinolyl, benzofuranyl, dihydrobenzofuranyl, methylenedioxybenzoyl, benzopyrazolyl, and benzotriazolyl, which may be unsubstituted or substituted, where the substituents are independently selected from:
(a) C$_{1-6}$ alkyl, C$_{2-6}$ alkenyl, C$_{2-6}$ alkynyl, wherein the alkyl, alkenyl, or alkynyl is unsubstituted or substituted, wherein the substituents are independently selected from:
(i) hydroxy,
(ii) halogen,
(iii) —NR$^9$R$^{10}$, wherein R$^9$ and R$^{10}$ are independently selected from hydrogen, C$_{1-6}$ alkyl, C$_{2-6}$ alkenyl, and C$_{2-6}$ alkynyl, wherein the alkyl, alkenyl, or alkynyl is unsubstituted or substituted, wherein the substituents are independently selected from:
  (A) phenyl, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
  (B) naphthyl, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
  (C) heterocycle, unsubstituted or substituted, wherein the substituents are independently selected from: halogen, hydroxy, C$_{1-6}$alkyl, C$_{1-6}$alkoxy, —CO$_2$(C$_{1-6}$ alkyl), —NH$_2$, —NH(C$_{1-6}$ alkyl), —N(C$_{1-6}$ alkyl)(C$_{1-6}$ alkyl), or trifluoromethyl,
  (D) hydroxy,
  (E) —O(C$_{1-6}$ alkyl),
  (F) —CO$_2$(C$_{1-6}$ alkyl),
  (G) —S(O)$_n$—(C$_{1-6}$ alkyl, wherein n is an integer selected from 0, 1 and 2,
  (H) halogen,
  (I) —NH$_2$,
  (J) —NH(C$_{1-6}$ alkyl), and
  (K) —N(C$_{1-6}$ alkyl)(C$_{1-6}$ alkyl),
(iv) —NR$^9$—COR$^{10}$,
(v) —NR$^9$—CO$_2$R$^{10}$,
(vi) —CO—NR$^9$R$^{10}$,
(vii) —OCO—NR$^9$R$^{10}$,
(viii) —NR$^9$CO—NR$^9$R$^{10}$,
(ix) —S(O)$_2$—NR$^9$R$^{10}$, wherein n is an integer selected from 0, 1 and 2,
(x) —NR$^9$S(O)$_2$—R$^{10}$,
(xi) —NR$^9$S(O)$_2$—NR$^9$R$^{10}$,
(xii) —S(O)$_n$—R$^9$,
(xiii) —CF$_3$,
(xiv) —CHF$_2$,
(xv) —CH$_2$F,
(xvi) —O—R$^9$,
(xvii) —O(C$_{1-6}$ alkyl)—O—R$^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—R$^9$,
(xxix) —OCO$_2$—R$^9$, and
(xxx) —CO—R$^9$,
(b) —O—C$_{1-6}$alkyl, —O—C$_{2-6}$ alkenyl, —O—C$_{2-6}$ alkynyl, wherein the alkyl, alkenyl, or alkynyl is unsubstituted or substituted, wherein the substituents are independently selected from:
(i) hydroxy,
(ii) halogen,
(iii) —NR$^9$R$^{10}$, (iv) —NR$^9$—COR$^{10}$,
(v) —NR$^9$—CO$_2$R$^{10}$,
(vi) —CO—NR$^9$R$^{10}$,
(vii) —OCO—NR$^9$R$^{10}$,
(viii) —NR$^9$CO—NR$^9$R$^{10}$,
(ix) —S(O)$_2$—NR$^9$R$^{10}$,
(x) —NR$^9$S(O)$_2$—R$^{10}$,
(xi) —NR$^9$S(O)$_2$—NR$^9$R$^{10}$,
(xii) —S(O)$_n$—R$^9$,
(xiii) —CF$_3$,
(xiv) —CHF$_2$,
(xv) —CH$_2$F,
(xvii) —O—R$^9$,
(xvii) —O(C$_{1-6}$ alkyl)—O—R$^9$,
(xviii) phenyl,
(xix) naphthyl,
(xx) indenyl,
(xxi) indanyl,
(xxii) heterocycle,
(xxiii) —CO-phenyl
(xxiv) —CO-naphthyl,
(xxv) —CO-indenyl,
(xxvi) —CO-indanyl,
(xxvii) —CO-heterocycle,
(xxviii) —OCO—R$^9$,
(xxix) —OCO$_2$—R$^9$, and
(xxx) —CO—R$^9$,
(c) —NO$_2$,
(d) hydroxy,
(e) halogen,
(f) —NR$^9$R$^{10}$,
(g) —NR$^9$—COR$^{10}$,
(h) —NR$^9$—CO$_2$R$^{10}$,
(i) —CO—NR$^9$R$^{10}$,
(j) —OCO—NR$^9$R$^{10}$,
(k) —NR$^9$CO—NR$^9$R$^{10}$,
(l) —S(O)$_2$—NR$^9$R$^{10}$,
(m) —NR$^9$S(O)$_2$—R$^{10}$,
(n) —NR$^9$S(O)$_2$—NR$^9$R$^{10}$,
(o) —S(O)$_n$—R$^9$,
(p) —CF$_3$,
(q) —CHF$_2$,
(r) —CH$_2$F,
(s) —OCO—R$^9$,
(t) —OCO$_2$—R$^9$, and
(u) —CO—R$^9$;
wherein R$^5$ is a selected from:
(1) phenyl, which is unsubstituted or substituted with halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl,
(2) —C$_{1-6}$alkyl-phenyl, —C$_{1-6}$alkyl-naphthyl, —C$_{1-6}$alkyl-indenyl, —C$_{1-6}$alkyl-indanyl, and —C$_{1-6}$alkyl-heterocycle, wherein the phenyl, naphthyl, indenyl, indanyl, or heterocycle is unsubstituted or substituted with: halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl; and wherein the —C$_{1-6}$alkyl is optionally substituted with oxo, hydroxy, C$_{1-6}$alkoxy, acetoxy, or halogen,
(3) —O—C$_{1-6}$alkyl-phenyl, —O—C$_{1-6}$alkyl-naphthyl, —O—C$_{1-6}$alkyl-indenyl, —O—C$_{1-6}$alkyl-indanyl, and —O—C$_{1-6}$alkyl-heterocycle, wherein the phenyl, naphthyl, indenyl, indanyl, or heterocycle is unsubstituted or substituted with: halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl,
(4) —C$_{1-4}$alkyl—O—C$_{1-4}$alkyl-phenyl, wherein the phenyl is unsubstituted or substituted with halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl, and
(5) —C$_{1-4}$alkyl—S(O)$_n$—C$_{1-4}$alkyl-phenyl, wherein the phenyl is unsubstituted or substituted with halogen, hydroxy, C$_{1-6}$alkyl, C$_{1-6}$alkoxy, —CO$_2$(C$_{1-6}$ alkyl), —NH$_2$, —NHR$^9$, —NR$^9$R$^{10}$, or trifluoromethyl;

R$^3$ is selected from:
C$_{1-8}$ alkyl, C$_{2-8}$ alkenyl, and C$_{2-8}$ alkynyl, wherein the alkyl, alkenyl, or alkynyl is unsubstituted or substituted, wherein the substituents are independently selected from:
(a) halogen,
(b) hydroxy,
(c) —CO$_2$(C$_{1-6}$ alkyl),
(d) —OCO—R$^9$,
(e) —OCO$_2$—R$^9$,
(f) —CO—R$^9$,
(g) phenyl or heterocycle, wherein the phenyl or heterocycle is unsubstituted or substituted, wherein the substituents are independently selected from: halogen, hydroxy, C$_{1-6}$alkyl, C$_{1-6}$alkoxy, —CO$_2$(C$_{1-6}$ alkyl), —NR$^9$R$^{10}$, or trifluoromethyl;
(h) —S(O)$_n$—R$^9$,
(i) —NR$^9$R$^{10}$,
(j) —NR$^9$—COR$^{10}$,
(k) —NR$^9$—CO$_2$R$^{10}$,
(l) —CO—NR$^9$R$^{10}$,
(m) —OCO—NR$^9$R$^{10}$,
(n) —NR$^9$CO—NR$^9$R$^{10}$,
(o) —S(O)$_2$—NR$^9$R$^{10}$,
(p) —NR$^9$S(O)$_2$—R$^{10}$,
(q) —NR$^9$S(O)$_2$—NR$^9$R$^{10}$,
(r) —CF$_3$,
(s) —CHF$_2$,
(t) —CH$_2$F, and
(u) —O—R$^9$;
and pharmaceuticaly acceptable salts and individual diastereomers thereof.

In the present invention it is preferred that
R$^1$ is —X—R$^8$, wherein X is selected from the group consisting of:
(1) —CH$_2$-, and
(2) —CO—, and wherein R$^8$ is a selected from: phenyl, naphthyl, biphenyl, indenyl, indanyl, and heterocycle, which may be unsubstituted or substituted, where the substituents are independently selected from:
(a) C$_{1-6}$alkyl, C$_{2-6}$alkenyl, C$_{2-6}$alkynyl, wherein the alkyl, alkenyl, or alkynyl is unsubstituted or substituted, wherein the substituents are independently selected from:
(i) hydroxy,
(ii) halogen,
(iii) —NR$^9$R$^{10}$, wherein R$^9$ and R$^{10}$ are independently selected from hydrogen, C$_{1-6}$alkyl, C$_{2-6}$alkenyl, and C$_{2-6}$alkynyl, wherein the alkyl, alkenyl, or alkynyl is unsubstituted or substituted, wherein the substituents are independently selected from:
(A) phenyl, unsubstituted or substituted, wherein the substituents are independently selected from: halogen, hydroxy, C$_{1-6}$alkyl, C$_{1-6}$alkoxy, —CO$_2$(C$_{1-6}$alkyl), —NH$_2$, —NH(C$_{1-6}$alkyl), —N(C$_{1-6}$alkyl)(C$_{1-6}$alkyl), or trifluoromethyl,
(B) naphthyl, unsubstituted or substituted, wherein the substituents are independently selected from: halogen, hydroxy, $C_{1-6}$alkyl, $C_{1-6}$alkoxy, —$CO_2(C_{1-6}$alkyl), —$NH_2$, —NH($C_{1-6}$alkyl), —N($C_{1-6}$alkyl)($C_{1-6}$alkyl), or trifluoromethyl,
(C) heterocycle, unsubstituted or substituted, wherein the substituents are independently selected from: halogen, hydroxy, $C_{1-6}$alkyl, $C_{1-6}$alkoxy, —$CO_2(C_{1-6}$alkyl), —$NH_2$, —NH($C_{1-6}$alkyl), —N($C_{1-6}$alkyl)($C_{1-6}$alkyl), or trifluoromethyl,
(D) hydroxy,
(E) —O($C_{1-6}$alkyl),
(F) —$CO_2(C_{1-6}$alkyl),
(G) —S(O)$_n$-($C_{1-6}$alkyl), wherein n is an integer selected from 0, 1 and 2,
(H) halogen,
(I) —$NH_2$,
(J) —NH($C_{1-6}$alkyl), and
(K) —N($C_{1-6}$alkyl)($C_{1-6}$alkyl),
(iv) —$NR^9$-$COR^{10}$,
(v) —$NR^9$-$CO_2R^{10}$,
(vi) —CO—$NR^9R^{10}$,
(vii) —OCO—$NR^9R^{10}$,
(viii) —$NR^9$CO—$NR^9R^{10}$,
(ix) —S(O)$_2$-$NR^9R^{10}$, wherein n is an integer selected from 0, 1 and 2,
(x) —$NR^9$S(O)$_2$-$R^{10}$,
(xi) —$NR^9$S(O)$_2$-$NR^9R^{10}$,
(xii) —S(O)$_n$-$R^9$,
(xiii) —$CF_3$,
(xiv) —$CHF_2$,
(xv) —$CH_2F$,
(xvi) —O—$R^9$,
(xvii) —O($C_{1-6}$alkyl)-O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$-$R^9$, and
(xxx) —CO—$R^9$,
(b) —O—$C_{1-6}$alkyl, —O—$C_{2-6}$alkenyl, —O—$C_{2-6}$alkynyl, wherein the alkyl, alkenyl, or alkynyl is unsubstituted or substituted, wherein the substituents are independently selected from:
(i) hydroxy,
(ii) halogen,
(iii) —$NR^9R^{10}$,
(iv) —$NR^9$-$COR^{10}$,
(v) —$NR^9$-$CO_2R^{10}$,
(vi) —CO—$NR^9R^{10}$,
(vii) —OCO—$NR^9R^{10}$,
(viii) —$NR^9$CO—$NR^9R^{10}$,
(ix) —S(O)$_2$-$NR^9R^{10}$,
(x) —$NR^9$S(O)$_2$-$R^{10}$,
(xi) —$NR^9$S(O)$_2$-$NR^9R^{10}$,
(xii) —S(O)$_n$-$R^9$,
(xiii) —$CF_3$,
(xiv) —$CHF_2$,
(xv) —$CH_2F$,
(xvii) —O—$R^9$,
(xvii) —O($C_{1-6}$alkyl)-O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$-$R^9$, and
(xxx) —CO—$R^9$,
(c) —$NO_2$,
(d) hydroxy,
(e) halogen,
(f) —$NR^9R^{10}$,
(g) —$NR^9$-$COR^{10}$,
(h) —$NR^9$-$CO_2R^{10}$,
(i) —CO—$NR^9R^{10}$,
(j) —OCO—$NR^9R^{10}$,
(k) —$NR^9$CO—$NR^9R^{10}$,
(l) —S(O)$_2$-$NR^9R^{10}$,
(m) —$NR^9$S(O)$_2$-$R^{10}$,
(n) —$NR^9$S(O)$_2$-$NR^9{}^{10}$,
(o) —S(O)$_n$-$R^9$,
(p) —$CF_3$,
(q) —$CHF_2$,
(r) —$CH_2F$,
(s) —OCO—$R^9$,
(t) —$OCO_2$-$R^9$, and
(u) —CO—$R^9$.

In the present invention it is even more preferred that $R^1$ is —X—$R^8$, wherein X is selected from the group consisting of:
(1) —$CH_2$, and
(2) —CO—, and wherein $R^8$ is a selected from: phenyl, naphthyl, indenyl, indanyl, indolyl, quinolyl, isoquinolyl, benzofuranyl, dihydrobenzofuranyl, methylenedioxybenzoyl, benzopyrazolyl, and benzotriazolyl, which may be unsubstituted or substituted, where the substituents are independently selected from:
(a) $C_{1-6}$alkyl, $C_{2-6}$alkenyl, $C_{2-6}$alkynyl, wherein the alkyl, alkenyl, or alkynyl is unsubstituted or substituted, wherein the substituents are independently selected from:
(i) hydroxy,
(ii) halogen,
(iii) —$NR^9R^{10}$, wherein $R^9$ and $R^{10}$ are independently selected from hydrogen, $C_{1-6}$alkyl, $C_{2-6}$alkenyl, and $C_{2-6}$alkynyl, wherein the alkyl, alkenyl, or alkynyl is unsubstituted or substituted, wherein the substituents are independently selected from:
(A) phenyl, unsubstituted or substituted, wherein the substituents are independently selected from: halogen, hydroxy, $C_{1-6}$alkyl, $C_{1-6}$alkoxy, —$CO_2(C_{1-6}$alkyl), —$NH_2$, —NH($C_{1-6}$alkyl), —N($C_{1-6}$alkyl)($C_{1-6}$alkyl), or trifluoromethyl,
(B) naphthyl, unsubstituted or substituted, wherein the substituents are independently selected from: halogen, hydroxy, $C_{1-6}$alkyl, $C_{1-6}$alkoxy, —$CO_2(C_{1-6}$aklyl), —$NH_2$, —NH($C_{1-6}$alkyl), —N($C_{1-6}$alkyl)($C_{1-6}$alkyl), or trifluoromethyl, (C) heterocycle, unsubstituted or substituted, wherein the substituents are independently selected from: halogen, hydroxy, $C_{1-6}$alkyl, $C_{1-6}$alkoxy, —$CO_2(C_{1-6}$alkyl), —$NH_2$, —NH($C_{1-6}$alkyl), —N($C_{1-6}$alkyl)($C_{1-6}$alkyl), or trifluoromethyl,
(D) hydroxy,
(E) —O($C_{1-6}$alkyl),
(F) —$CO_2(C_{1-6}$alkyl),
(G) —S(O)$_n$-($C_{1-6}$alkyl), wherein n is an integer selected from 0, 1 and 2,
(H) halogen,
(I) —$NH_2$,
(J) —NH($C_{1-6}$alkyl), and
(K) —N($C_{1-6}$alkyl)($C_{1-6}$alkyl),
(v) —$NR^9$-$COR^{10}$,
(vi) —$NR^9$-$CO_2R^{10}$,
(vii) —CO—$NR^9R^{10}$,
(viii) —OCO—$NR^9R^{10}$,
(ix) —$NR^9$CO—$NR^9R^{10}$,
(x) —S(O)$_2$-$NR^9R^{10}$, wherein n is an integer selected from 0, 1 and 2,
(xi) —$NR^9$S(O)$_2$-$R^{10}$,
(xii) —$NR^9$S(O)$_2$-$NR^9R^{10}$,
(xiii) —S(O)$_n$-$R^9$,
(xiv) —$CF_3$,
(xv) —$CHF_2$,
(xvi) —$CH_2F$,
(xvii) —O—$R^9$,
(xvii) —O($C_{1-6}$alkyl)-O—$R^9$,
(xix) phenyl,
(xx) naphthyl,
(xxi) indenyl,
(xxii) indanyl,
(xxiii) heterocycle,
(xxiv) —CO-phenyl,
(xxv) —CO-naphthyl,
(xxvi) —CO-indenyl,
(xxvii) —CO-indanyl,
(xxviii) —CO-heterocycle,
(xxix) —OCO—$R^9$,
(xxx) —$OCO_2$-$R^9$, and
(xxxi) —CO—$R^9$,
(b) —O—$C_{1-6}$alkyl, —O—$C_{2-6}$alkenyl, —O—$C_{2-6}$alkynyl, wherein the alkyl, alkenyl, or alkynyl is unsubstituted or substituted, wherein the substituents are independently selected from:
(i) hydroxy,
(ii) halogen,
(iii) —$NR^9R^{10}$,
(iv) —$NR^9$-$COR^{10}$,
(v) —$NR^9$-$CO_2R^{10}$,
(vi) —CO—$NR^9R^{10}$,
(vii) —OCO—$NR^9R^{10}$,
(viii) —$NR^9$CO—$NR^9R^{10}$,
(ix) —S(O)$_2$-$NR^9R^{10}$,
(x) —$NR^9$S(O)$_2$-$R^{10}$,
(xi) —$NR^9$S(O)$_2$-$NR^9R^{10}$,
(xii) —S(O)$_n$-$R^9$,
(xiii) —$CF_3$,
(xiv) —$CHF_2$,
(xv) —$CH_2F$,
(xvii) —O—$R^9$,
(xvii) —O($C_{1-6}$alkyl)-O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$-$R^9$, and
(xxx) —CO—$R^9$,
(c) —$NO_2$,
(d) hydroxy,
(e) halogen,
(f) —$NR^9R^{10}$,
(g) —$NR^9COR^{10}$,
(h) —$NR^9CO_2R^{10}$,
(i) —CO—$NR^9R^{10}$,
(j) —OCO—$NR^9R^{10}$,
(k) —$NR^9$CO—$NR^9R^{10}$,
(l) —S(O)$_2$-$NR^9R^{10}$,
(m) —$NR^9$S(O)$_2$-$R^{10}$,
(n) —$NR^9$S(O)$_2NR^9R^{10}$,
(o) —S(O)$_n$-$R^9$,
(p) —$CF_3$,
(q) —$CHF_2$,
(r) —$CH_2F$,
(s) —OCO—$R^9$,
(t) —$OCO_2$-$R^9$, and
(u) —CO—$R^9$.

In the present invention it is highly preferred that $R^1$ is selected from the group consisting of:
(1) —$CH_2$-phenyl,
(2) —CO-phenyl,
(3) —$CH_2$-(2,4-dichlorophenyl),
(4) —CO-(2,4-dichlorophenyl),
(5) —$CH_2$-(2-naphthyl),
(6) —CO-(1-naphthyl),
(7) —$CH_2$-indoyl, and
(8) —CO-indolyl.

In the present invention it is more preferred that $R^1$ is selected from the group consisting of:
(1) —$CH_2$-phenyl,
(2) —CO-phenyl,
(3) —$CH_2$-(2,4-dichlorophenyl),
(4) —$CH_2$-(7-indolyl), and
(5) —CO-(7-indolyl).

In the present invention it is preferred that $R^2$ is:

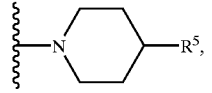

wherein $R^5$ is selected from:
(1) phenyl, which is unsubstituted or substituted with halogen, hydroxy, $C_{1-6}$alkyl, $C_{1-6}$alkoxy, and trifluoromethyl,
(2) —$C_{1-6}$alkyl-phenyl, wherein the phenyl is unsubstituted or substituted with: halogen, hydroxy, $C_{1-6}$alkyl, $C_{1-6}$alkoxy, or trifluoromethyl; and wherein the —$C_{1-6}$alkyl is optionally substituted with oxo, hydroxy, $C_{1-6}$alkoxy, acetoxy, or halogen,
(3) —O—$C_{1-6}$alkyl-phenyl, wherein the phenyl is unsubstituted or substituted with halogen, hydroxy, $C_{1-6}$alkyl, $C_{1-6}$alkoxy, or trifluoromethyl, (4) —C$_{1-4}$alkyl-O—C$_{1-4}$alkyl-phenyl, wherein the phenyl is unsubstituted or substituted with halogen, hydroxy, C$_{1-6}$alkyl, C$_{1-6}$alkoxy, or trifluoromethyl, and (5) —C$_{1-4}$alkyl-S(O)$_n$-C$_{1-4}$alkyl-phenyl, wherein n is an integer selected from 0, 1 and 2, and wherein the phenyl is unsubstituted or substituted with halogen, hydroxy, C$_{1-6}$alkyl, C$_{1-6}$alkoxy, or trifluoromethyl.

In the present invention it is more preferred that R$^2$ is:

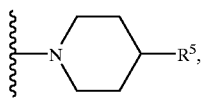

wherein R$^5$ is a selected from:

(1) phenyl, which is unsubstituted or substituted with halogen, hydroxy, C$_{1-6}$alkyl, C$_{1-6}$alkoxy, or trifluoromethyl, (2) —C$_{2-4}$alkyl-phenyl, wherein the phenyl is unsubstituted or substituted with chloro, fluoro, trifluoromethyl, methyl or ethyl and wherein the —C$_{2-4}$alkyl is optionally substituted with oxo, hydroxy, halogen, or methoxy, (3) —C$_{1-3}$alkyl-O—C$_{1-3}$alkyl-phenyl, wherein the phenyl is unsubstituted or substituted with chloro, fluoro, trifluoromethyl, methyl or ethyl, and (4) —C$_{1-3}$alkyl-S(O)$_n$-C$_{1-3}$alkyl-phenyl, wherein the phenyl is unsubstituted or substituted with chloro, fluoro, trifluoromethyl, methyl, or ethyl.

In the present invention it is still more preferred that R$^2$ is:

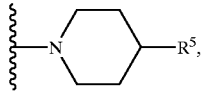

wherein R$^5$ is a selected from:

(1) phenyl, which is unsubstituted or substituted with halogen, hydroxy, C$_{1-6}$alkyl, C$_{1-6}$alkoxy, or trifluoromethyl, (2) —C$_{3-4}$alkyl-phenyl, wherein the phenyl is unsubstituted or substituted with chloro, fluoro or methyl, and wherein the —C$_{3-4}$alkyl is optionally substituted with oxo, hydroxy, or methoxy, (3) —C$_{1-3}$alkyl-O—C$_{1-3}$alkyl-phenyl, wherein the phenyl is unsubstituted or substituted with chloro, fluoro or methyl, and (4) —C$_{1-3}$alkyl-S(O)$_n$-C$_{1-3}$alkyl-phenyl, wherein the phenyl is unsubstituted or substituted with chloro, fluoro or methyl.

In the present invention it is highly preferred that R$^2$ is:

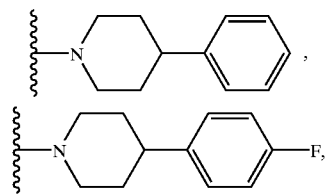

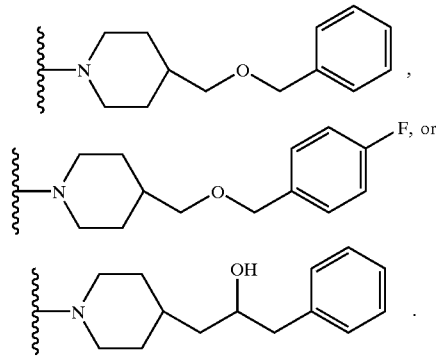

In the present invention it is preferred that R$^3$ is selected from:

C$_{1-8}$alkyl, C$_{2-8}$alkenyl, C$_{2-8}$alkynyl, wherein the alkyl, alkenyl, or alkynyl is unsubstituted or substituted, wherein the substituents are independently selected from:
(a) halogen,
(b) hydroxy,
(c) —CO$_2$(C$_{1-6}$alkyl),
(d) —OCO—R$^9$,
(e) —OCO$_2$-R$^9$,
(f) —CO—R$^9$,
(g) phenyl, wherein the phenyl is unsubstituted or substituted with: halogen, hydroxy, C$_{1-6}$alkyl, C$_{1-6}$alkoxy, —CO$_2$(C$_{1-6}$alkyl), —NR$^9$R$^{10}$, or trifluoromethyl;
(h) —S(O)$_n$-R$^9$,
(i) —NR$^9$R$^{10}$,
(j) —NR$^9$-COR$^{10}$,
(k) —NR$^9$-CO$_2$R$^{10}$,
(l) —CO—NR$^9$R$^{10}$,
(m) —OCO—NR$^9$R$^{10}$,
(n) —NR$^9$CO—NR$^9$R$^{10}$,
(o) —S(O)$_2$-NR$^9$R$^{10}$,
(p) —NR$^9$S(O)$_2$-R$^{10}$,
(q) —NR$^9$S(O)$_2$-NR$^9$R$^{10}$,
(r) —CF$_3$,
(s) —CHF$_2$, and
(t) —CH$_2$F.

In the present invention it is more preferred that R$^3$ is selected from:

C$_{1-6}$alkyl, C$_{2-6}$alkenyl, and C$_{2-6}$alkynyl, wherein the alkyl, alkenyl, or alkynyl is unsubstituted or substituted, wherein the substituents are independently selected from:
(a) halogen,
(b) hydroxy,
(c) —O—C$_{1-6}$alkyl,
(d) phenyl,
(e) —O-phenyl,
(f) —CO$_2$-C$_{1-6}$alkyl, and
(g) —CF$_3$.

In the present invention it is highly preferred that R$^3$ is selected from:

(1) —C(CH$_3$)$_3$,
(2) —CH=CH$_2$,
(3) —CF$_3$,
(4) —CH$_2$OH,
(5) —CH(OH)CH$_3$,
(6) —C(OH)(CH$_3$)$_2$, (7) —CH(OH)CH$_2$CH$_3$,
(8) —CH(OH)CH=CH$_2$,
(9) —CH(OH)CH$_2$CH=CH$_2$,
(10) —CH(OH)C≡CH,
(11) —CH(OH)phenyl,
(12) —CH(OH)CH$_2$-phenyl,
(13) —CH$_2$-O-phenyl,
(14) —CH$_2$-O—CH$_3$,
(15) —CH$_2$-O—CH$_2$CH$_3$,
(16) —CH(CH$_3$)-O—CH$_3$,
(17) —CH(—O—CH$_3$)$_2$,
(18) —CH(—O—CH$_2$CH$_3$)$_2$, and
(19) —CH$_2$NHCH$_2$-phenyl.

In the present invention it is preferred that $R^{4c}$, $R^{4d}$, and $R^{4h}$ are independently selected from the group consisting of:
(1) hydrogen, and
(2) C$_{1-6}$alkyl.

In the present invention it is more preferred that $R^{4c}$, and $R^{4h}$ are each hydrogen and that $R^{4d}$ is selected from the group consisting of hydrogen, and —CH$_3$ In the present invention it is most preferred that $R^{4c}$, $R^{4d}$, and $R^{4h}$ are each hydrogen.

The compounds of the instant invention have at least two asymmetric centers at the ring junction of the substituents bearing $R^2$ and $R^3$. Additional asymmetric centers may be present depedening upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the most preferred compounds of this invention are of the trans orientation, i.e. as depicted:

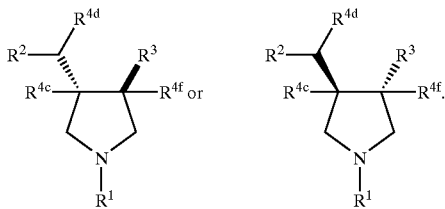

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, C$_{1-8}$, as in C$_{1-8}$alkyl is defined to identify the group as having 1, 2, 3, 4, 5, 6, 7 or 8 carbons in a linear or branched arrangement, such that C$_{1-8}$alkyl specifically includes methyl, ethyl, propyl, butyl, pentyl, hexyl, heptyl and octyl. The term "heterocycle" as used herein is intended to include the following groups: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyrindinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, Exemplifying the invention is the use of the compounds disclosed in the Examples and herein.

Specific compounds within the present invention include a compound which is selected from the group consisting of:

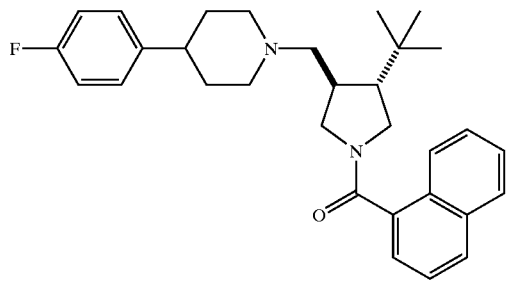

1-(1-Naphthoyl)-3-(RS)-(4-(4-fluorophenyl)piperidinylmethyl)-4-(RS)-(t-butyl)pyrrolidine;

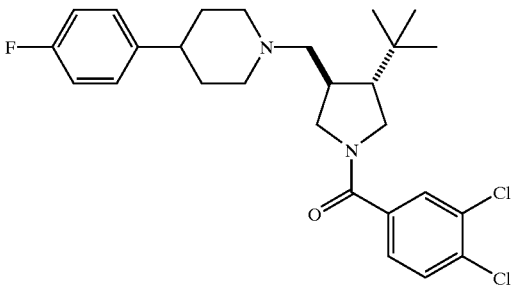

1-(3,4-Dichlorobenzoyl)-3-(RS)-(4-(4-fluorophenyl)piperidinylmethyl)-4-(RS)-(t-butyl)pyrrolidine;

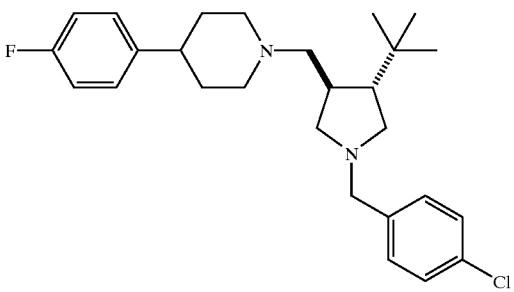

1-(4-Chlorobenzyl)-3-(RS)-(4-(4-fluorophenyl)piperidinylmethyl)-4-(RS)-(t-butyl)pyrrolidine;

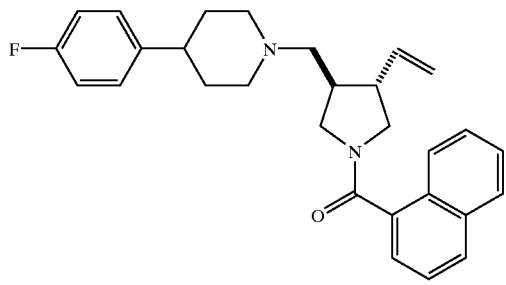

1-(1-Naphthoyl)-3-(RS)-(4-(4-fluorophenyl)
piperidinylmethyl)-4-(SR)-(vinyl)pyrrolidine;

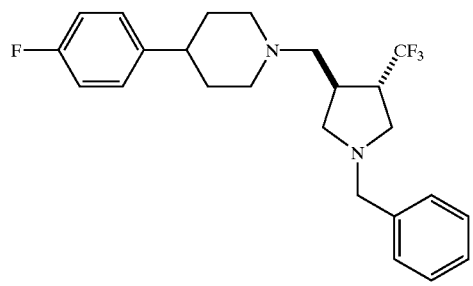

1-Benzyl-3-(RS)-(4-(4-fluorophenyl)piperidinylmethyl)-4-
(SR)-(trifluoromethyl)pyrrolidine;

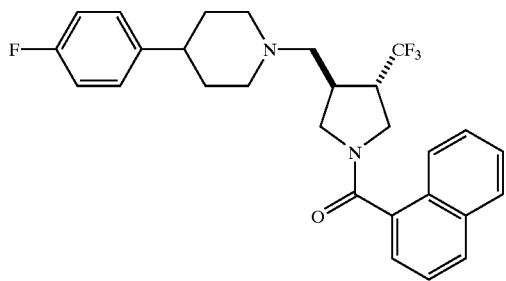

1-(2-Naphthoyl)-3-(RS)-(4-(4-fluorophenyl)
piperidinylmethyl)-4-(SR)-(trifluoromethyl)pyrrolidine;

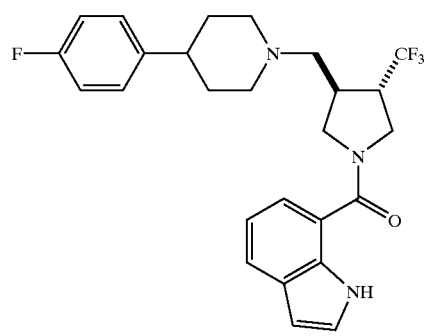

1-(7-Indolecarbonyl)-3-(RS)-(4-(4-fluorophenyl)
piperidinylmethyl)-4-(SR)-(trifluoromethyl)pyrrolidine;

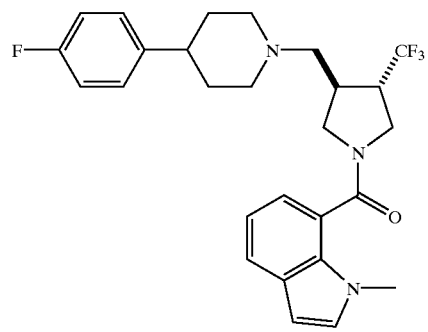

1-(1-Methyl-7-indolecarbonyl)-3-(RS)-(4-(4-fluorophenyl)
piperidinyl-methyl)-4-(SR)-(trifluoromethyl)pyrrolidine;

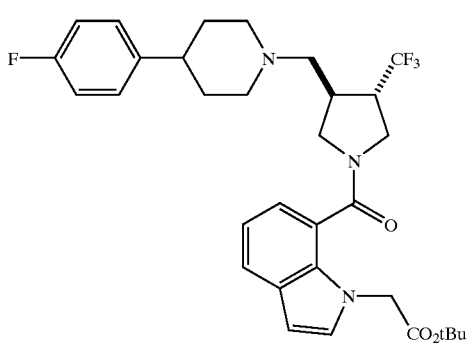

1-(1-t-Butoxycarbonylmethyl)-7-indolecarbonyl)-3-(RS)-
(4-(4-fluorophenyl)piperidinylmethyl)-4-(SR)-
(trifluoromethyl)pyrrolidine;

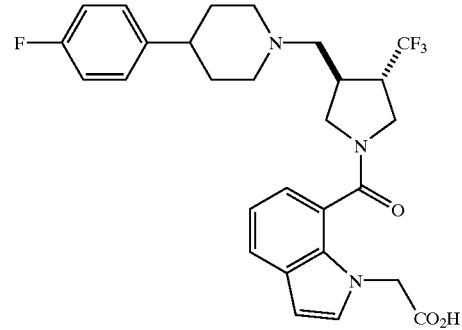

1-(1-Carboxymethyl)-7-indolecarbonyl)-3-(RS)-(4-(4-
fluorophenyl)piperidinylmethyl)-4-(SR)-(trifluoromethyl)
pyrrolidine;

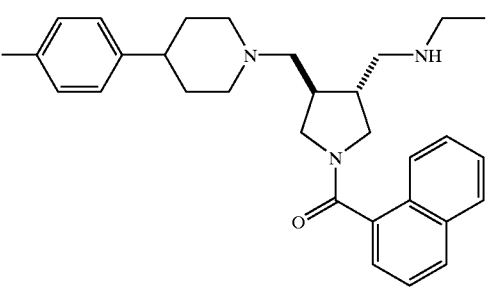

1-(1-Naphthoyl)-3-(RS)-(4-(4-fluorophenyl)
piperidinylmethyl)-4-(RS)-(ethylaminomethyl)pyrrolidine;

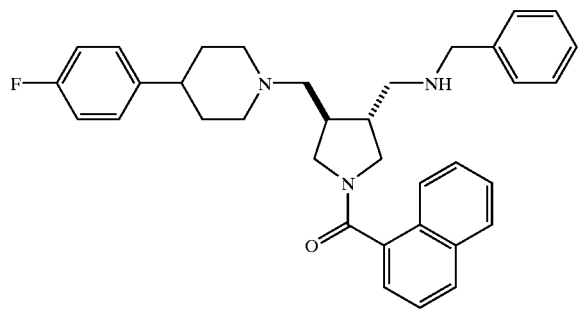

1-(1-Naphthoyl)-3-(RS)-(4-(4-fluorophenyl)piperidinylmethyl)-4-(RS)-(benzylaminomethyl)pyrrolidine;

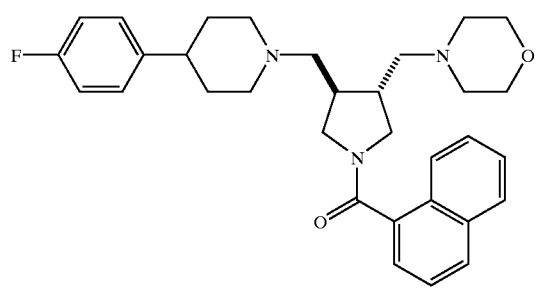

1-(1-Naphthoyl)-3-(RS)-(4-(4-fluorophenyl)piperidinylmethyl)-4-(RS)-(1-morpholinomethyl)pyrrolidine;

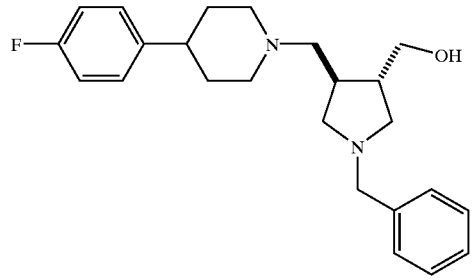

1-Benzyl-3-(RS)-(4-(4-fluorophenyl)piperidinylmethyl)-4-(SR)-hydroxymethylpyrrolidine;

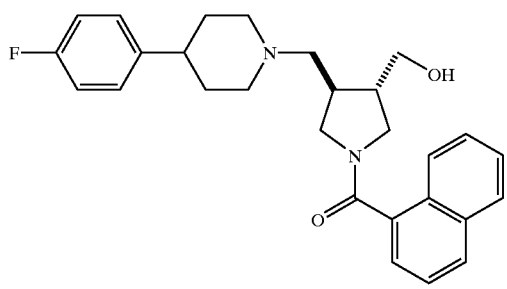

1-(1-Naphthoyl)-3-(RS)-(4-(4-fluorophenyl)piperidinylmethyl)-4-(SR)-hydroxyethylpyrrolidine;

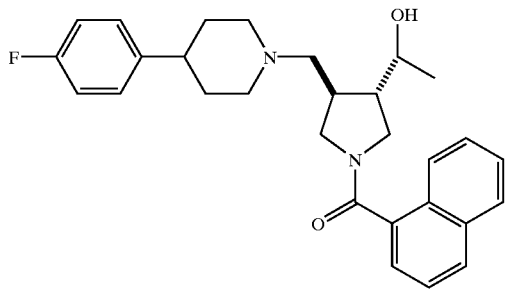

1-(1-Naphthoyl)-3-(RS)-(4-(4-fluorophenyl)piperidinylmethyl)-4-(SR)-(1-hydroxyethyl)pyrrolidine;

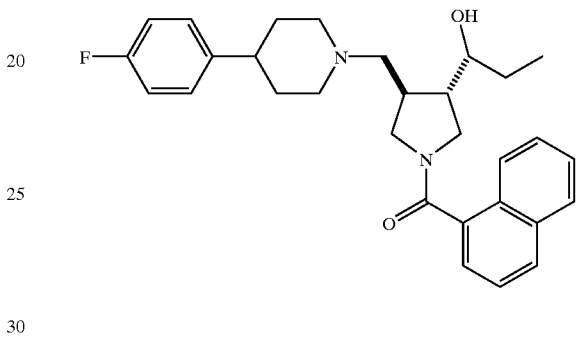

1-(1-Naphthoyl)-3-(RS)-(4-(4-fluorophenyl)piperidinylmethyl)-4-(SR)-(1-hydroxypropyl)pyrrolidine;

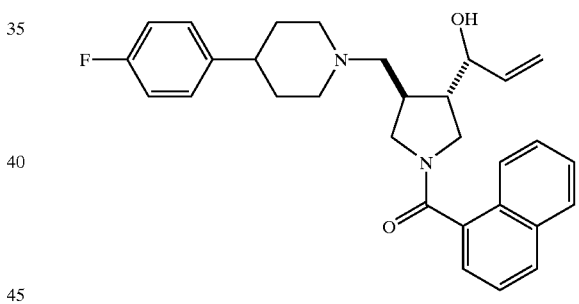

1-(1-Naphthoyl)-3-(RS)-(4-(4-fluorophenyl)piperidinylmethyl)-4-(SR)-(1-hydroxy-2-propenyl)pyrrolidine;

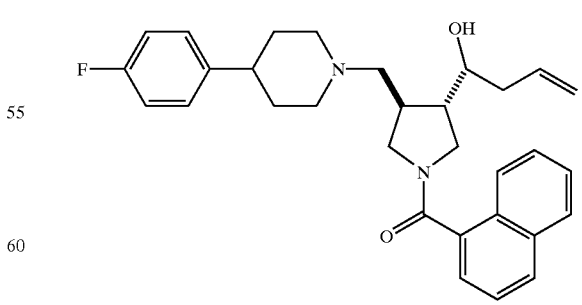

1-(1-Naphthoyl)-3-(RS)-(4-(4-fluorophenyl)piperidinylmethyl)-4-(SR)-(1-hydroxy-3-butenyl)pyrrolidine;

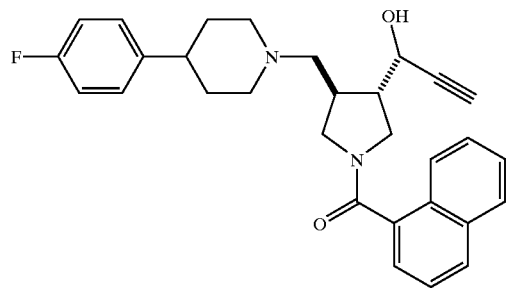

1-(1-Naphthoyl)-3-(RS)-(4-(4-fluorophenyl) piperidinylmethyl)-4-(SR)-(1-hydroxy-2-propynyl) pyrrolidine;

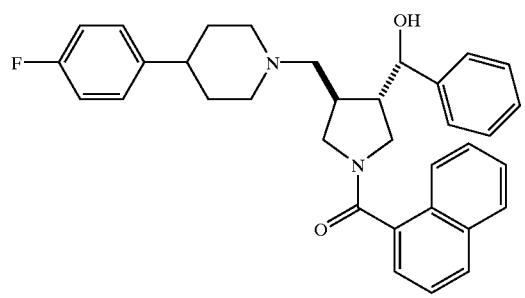

1-(1-Naphthoyl)-3-(RS)-(4-(4-fluorophenyl) piperidinylmethyl)-4-(SR)-(phenylhydroxymethyl) pyrrolidine;

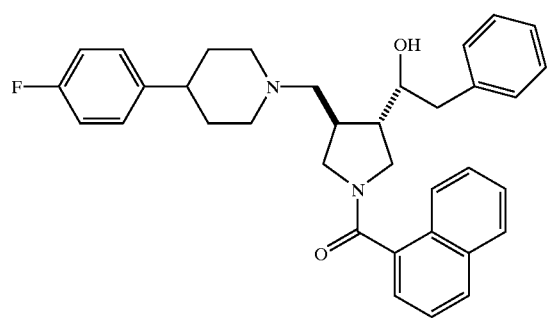

1-(1-Naphthoyl)-3-(RS)-(4-(4-fluorophenyl) piperidinylmethyl)-4-(SR)-(2-phenyl-1-hydroxyethyl) pyrrolidine;

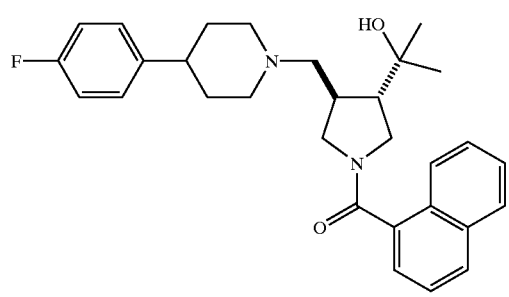

1-(1-Naphthoyl)-3-(RS)-(4-(4-fluorophenyl) piperidinylmethyl)-4-(SR)-(1-hydroxy-1-methylethyl) pyrrolidine;

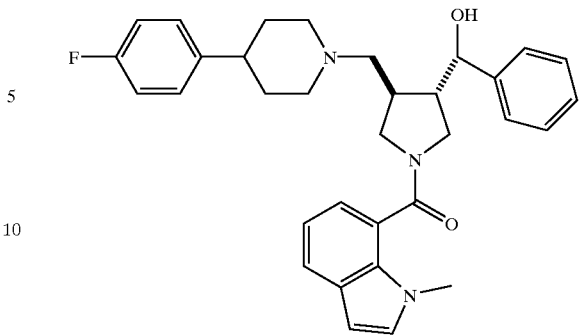

1-(1-Methyl-7-indolecarbonyl)-3-(RS)-(4-(4-fluorophenyl) piperidinyl-methyl)-4-(SR)-(phenylhydroxymethyl) pyrrolidine;

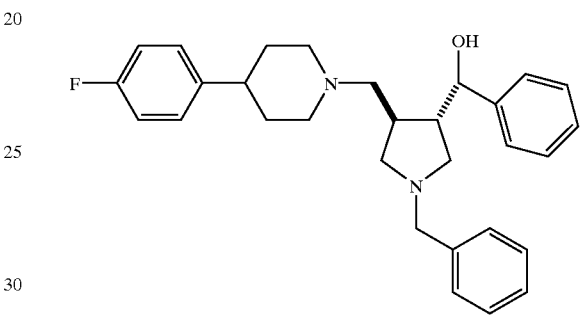

1-Benzyl-3-(RS)-(4-(4-fluorophenyl)piperidinylmethyl)-4-(SR)-(phenylhydroxymethyl)pyrrolidine;

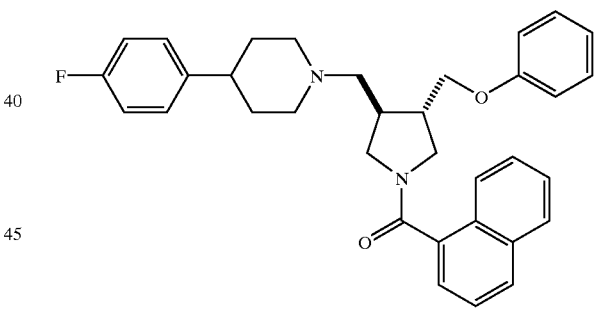

1-(1-Naphthoyl)-3-(RS)-(4-(4-fluorophenyl) piperidinylmethyl)-4-(SR)-(phenoxymethyl)pyrrolidine;

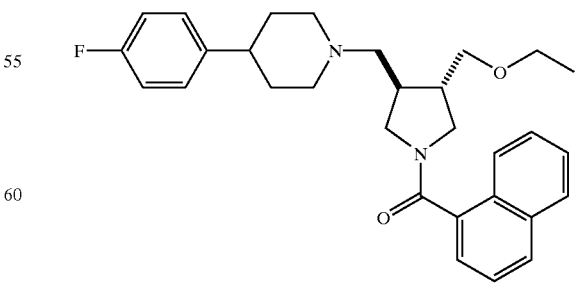

1-(1-Naphthoyl)-3-(RS)-(4-(4-fluorophenyl) piperidinylmethyl)-4-(S,R)-(ethoxymethyl)pyrrolidine;

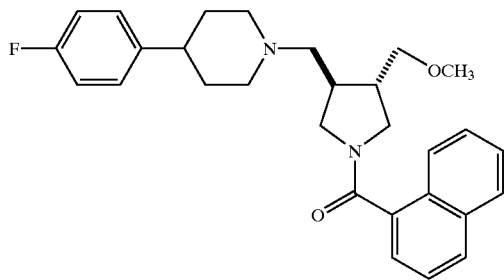

1-(1-Naphthoyl)-3-(RS)-(4-(4-fluorophenyl)piperidinylmethyl)-4-(SR)-(methoxymethyl)pyrrolidine;

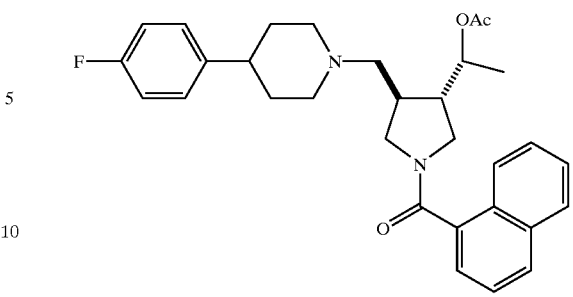

1-(1-Naphthoyl)-3-(RS)-(4-(4-fluorophenyl)piperidinylmethyl)-4-(SR)-1-acetoxyethyl)pyrrolidine;

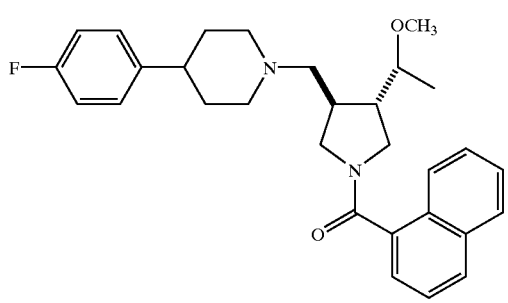

1-(1-Naphthoyl)-3-(RS)-(4-(4-fluorophenyl)piperidinylmethyl)-4-(RS)-(1-methoxyethyl)pyrrolidine;

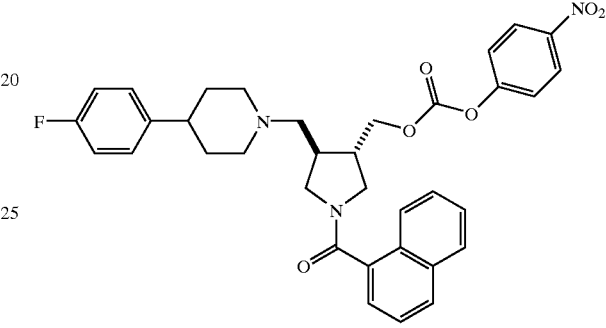

1-(1-Naphthoyl)-3-(RS)-(4-(4-fluorophenyl)piperidinylmethyl)-4-(SR)-(4-nitrophenoxycarbonyloxymethyl)-pyrrolidine;

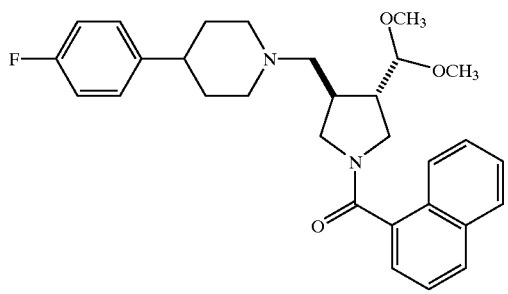

1-(1-Naphthoyl)-3-(RS)-(4-(4-fluorophenyl)piperidinylmethyl)-4-(S,R)-(1,1-dimethoxymethyl)pyrrolidine;

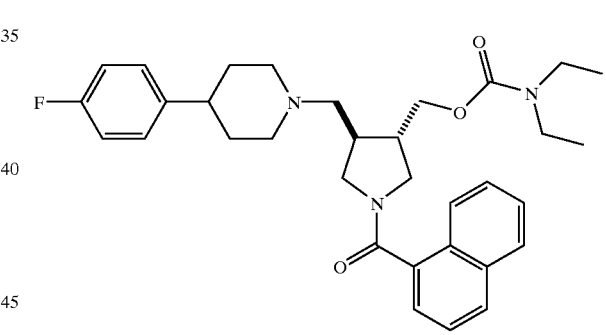

1-(1-Naphthoyl)-3-(RS)-(4-(4-fluorophenyl)piperidinylemthyl)-4-(SR)-(N,N-diethylcarbamoyloxymethyl) pyrrolidine;

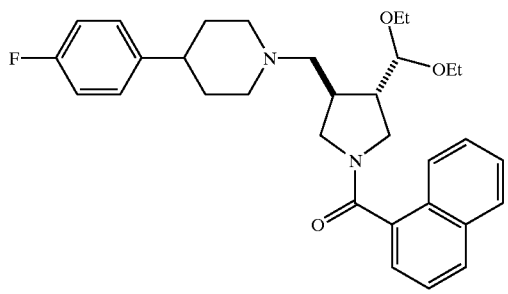

1-(1-Naphthoyl)-3-(RS)-(4-(4-fluorophenyl)piperidinylcarbonyl)-4-(SR)-(1,1-diethoxymethyl)pyrrolidine;

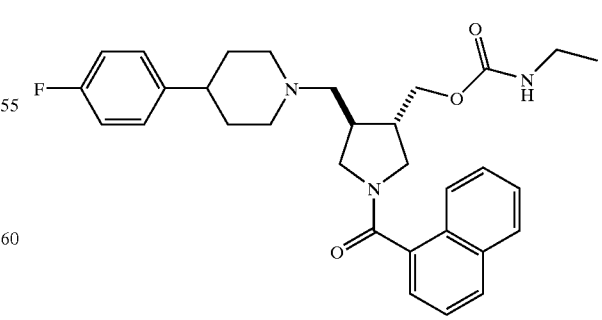

1-(1-Naphthoyl)-3-(RS)-(4-(4-fluorophenyl)piperidinylmethyl)-4-(SR)-(N-ethylcarbamoyloxymethyl)pyrrolidine;

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing spiro-substituted azacycles as modulators of chemokine receptor activity. In particular, these compounds are useful as modulators of the chemokine receptors, including CCR-3 and/or CCR-5.

The utility of the compounds in accordance with the present invention as modulators of chemokine receptor activity may be demonstrated by methodology known in the art, such as the assay for CCR-5 binding as disclosed by Van Riper, et al., *J. Exp. Med.,* 177, 851–856 (1993), and the assay for CCR-3 binding as disclosed by Daugherty, et al., *J. Exp. Med.,* 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md., as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology,* 65(9), 4887–4892 (1991).

In particular, the compounds of the following examples had activity in binding to the CCR-3 or the CCR-5 receptor in the aforementioned assays, generally with an $IC_{50}$ of less than about 1 $\mu$M. Such a result is indicative of the intrinsic activity of the compounds in use as modulators of chemokine receptor activity.

Mammalian chemokine receptors provide target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, pooriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions or humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Stronglyloidiasis, Trichinosis, filariasis); trematodes (flukes) (Schistosomiasis, Clonorchiasis), cestodes (tape worms) (Echinococcosis, *Taeniasis saginata,* Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-3 and/or CCR-5. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-3 and/or CCR-5. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-3 or CCR-5, of a target cell, which comprises contacting the target cell with an amount of the compound which is effective at inhibiting the binding of the chemokine to the chemoline receptor.

The subject treated in the methods above is a mammal, preferably a human being, male or female, in whom modulation of chemokine receptor activity is desired. "Modulation" as used herein is intended to encompass antagonism, agonism, partial antagonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxican, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophredine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atopine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicyclic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (–) 6-Chloro-4(S)-cyclopropylethynyl-4(S)-trifluoro-meth-yl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz, DMP-266 | DuPont-Merck Pharmaceuticals | HIV infection, AIDS, ARC (non-nucleoside reverse transcriptase inhibitor) |

-continued

| Drug Name | Manufacturer | Indication |
|---|---|---|
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |

IMMUNO-MODULATORS

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |

-continued

| Drug Name | Manufacturer | Indication |
|---|---|---|
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleotise inhibitor of HIV reverse transcriptase, such as AZT, 3TC, ddC or ddI. Preferred agents for combination therapy include: Zidovudine, Lamivudine, Stavudine, Efavirenz, Rtionavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2(R)-phenylmethyl-4-phenyl-3-((S)-tetrahydrofuran-3-yloxycarbonylamino-butyl)-N-isobutyl-benzenesulfonamide), N-(2(R)-hydroxy-1(S)-indanyl)-2(R)-phenylmethyl-4-(S)-hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intrapertioneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specific ingredients in the specified amounts.

The pharmaceutical compositions contains the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipient which are suitable for the manufacture of tablets. These excipient may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablet for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipient suitable for the manufacture of aqueous suspensions. Such excipients are suspending agents, for example sodium carboxymethylcellulose, methylcellulose, hydroxy- propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered n single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made from known procedures or as illustrated.

Several methods for preparing the compounds of this invention are illustrated in the following Schemes and Examples.

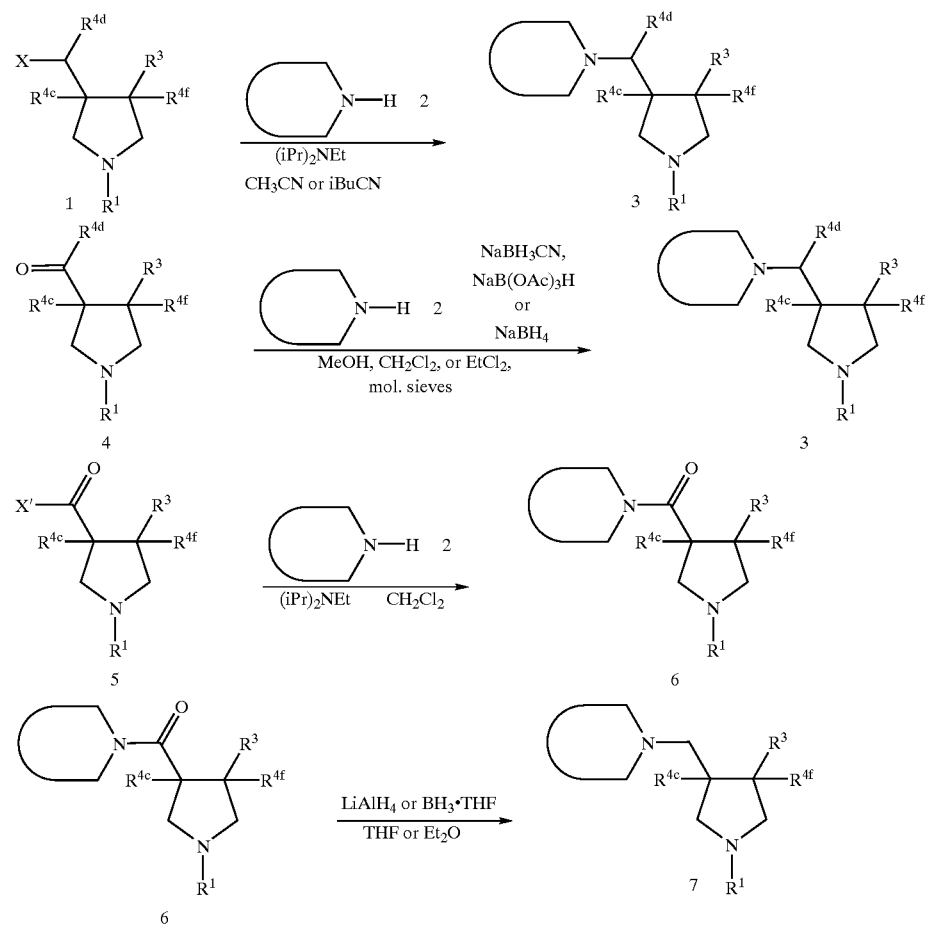

SCHEME 1

In one protocol, the compounds of the present invention are prepared by alkylating heterocycle 1 (wherein X is a leaving group such as, for example, bromide, iodide, methanesulfonate, p-toluenesulfonate, trifluoromethanesulfonate) with cyclic amine 2 under appropriate conditions to provide compound 3. Cyclic amine 2 is available commercially or can be prepared using the methods given below.

Alternatively, heterocyclic 4, bearing a carbonyl group, can be combined with the cyclic amine 2 and the intermediate imine or iminium species is reduced to tertiary amine 3 under homogenous conditions (e.g. using sodium cyanoborohydride, sodium borohydride, or sodium triacetoxyborohydride) or in the presence of hydrogen and a heterogeneous catalyst (e.g. palladium on carbon or Raney nickel).

In an alternative embodiment of the present invention, heterocycle 5, bearing an activated acyl side chain (wherein X', for example, is a chloride or bromide atom, or is a hydroxybenzotriazole residue from activation of the corresponding carboxylic acid with HOBt in the presence of a suitable carbodiimide) is allowed to react with cyclic amine 2 to provide the corresponding tertiary amide 6. Compound 6 can then be treated with a suitable reducing agent (e.g. diborane; borane in THF; borane dimethylsulfide, or lithium aluminum hydride) to provide the desired product 7.

zinc azide bis(pyridine) complex in the presence of triphenylphosphine and diethyl azodicarboxylate, or with diphenylphosphoryl azide, or with hydrazoic acid, provides azide 9. Reductin of 9, for example, with hydrogen and palladium on carbon, affords primary amine 10. This amine can be doubly alkylated with a bis-electrophile such as 13 under basic conditions, to provide the compound 14. Bis-electrophiles can be prepared from substituted glutaric anhydride derivatives such as 11 by reduction to diol 12 followed by double activation, using, for example, p-toluenesulfonyl chloride in pyridine, or triphenylphosphine carbon tetrabromide in acetonitrile, to provide 13 (where X=Br or OTs).

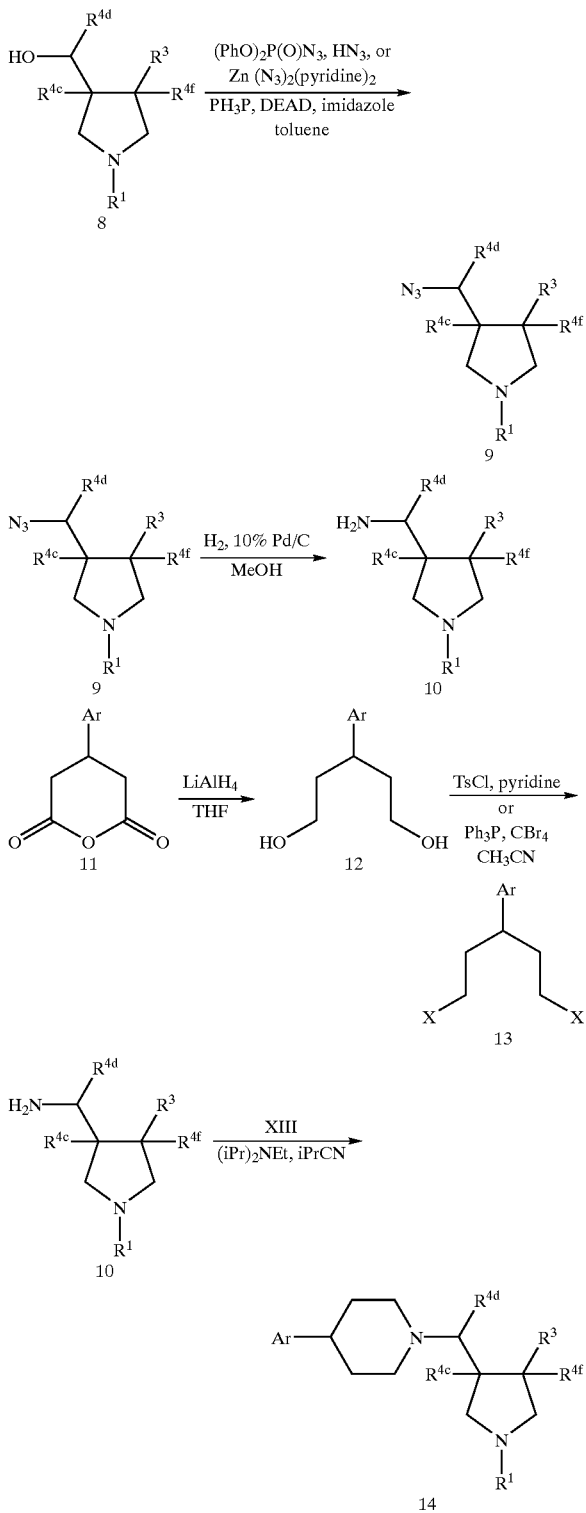

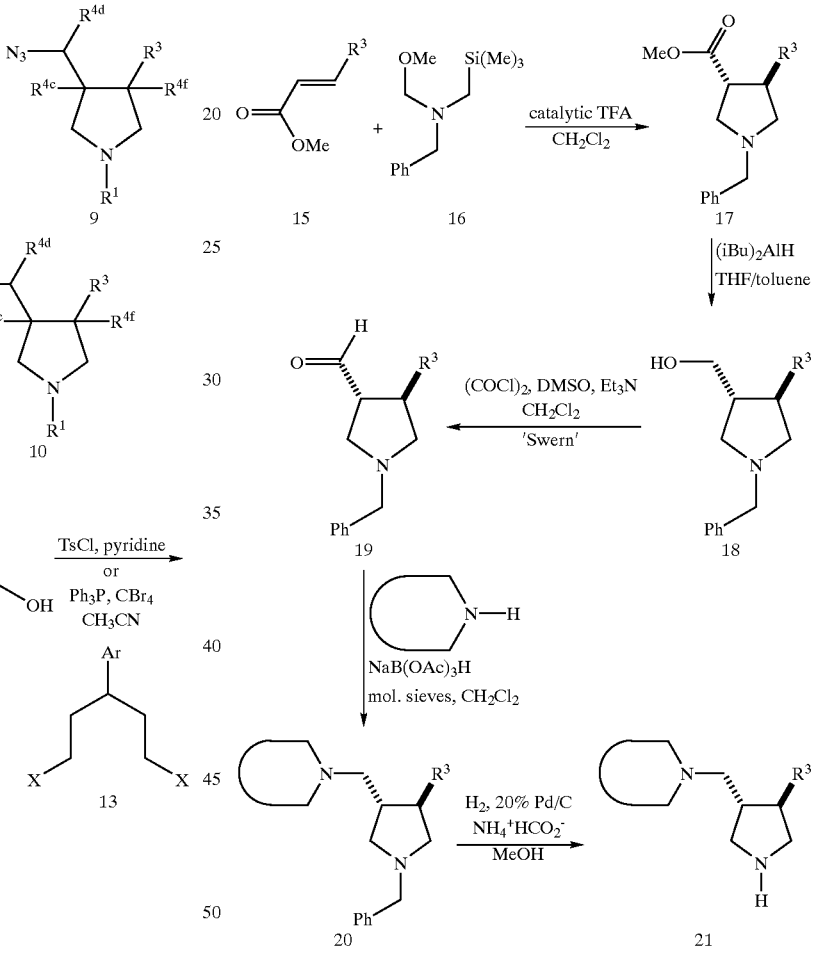

An alternative preparation of the target compounds is carried out as show in Scheme 2. Treatment of alcohol 8 with The preparation of compounds within the scope of the instant invention which bear a 1,3,4-trisubstituted pyrrolidine framework is detailed in Scheme 3. Treatment of a trans-cinnamic ester such as 15 with N-benzyl-N-methoxymethyl-N-(trimethylsilyl)-methylamine (16) in the presence of a catalytic amount of an acid such as TFA, titanium tetrafluoride lithium fluoride or cesium fluoride according to the procedure of Padwa et al (*J. Org. Chem.* 1987, 52, 235) preferentially affords the 3,4-trans pyrrolidine 17. Executing this sequence starting from the cis-cinnamic ester results in preferential formation of the 3,4-cis pyrrolidine. Reduction of ester 17 with diisobutylaluminum hydride, lithium aluminium hydride, or sodium bis(2-methoxyethoxy)aluminum hydride, provides the primary alcohol 18. Oxidation of 18 to the aldehyde 19 can be carried out under numerous conditions, such as with the Swern reaction, with DMSO and oxalyl chloride at low temperature, followed by triethylamine, or with various chromium trioxide-based reagents (see March J. "Advanced Organic Chemistry", 4th ed., John Wiley & Sons, New York, pp. 1167–1171 (1992)). Reductive amination with cyclic amine 2 provides diamine 20. Alternatively, The N-benzyl group is cleaved in a hydrogen atmosphere in the presence of 10% palladium on carbon or with Pearlmans' catalyst [Pd(OH)$_2$/C] to provide the secondary amine 21.

SCHEME 4

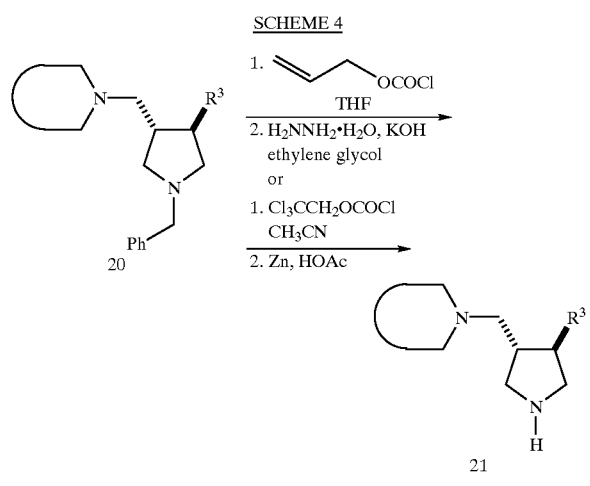

In cases when certain substituents are labile to hydrogenolysis conditions, alternative methods to remove the benzyl group of compound 20 are described in Scheme 4. Compound 20 may be converted to the allyloxycarbamate derivative by stirring with allylchloroformate at rt in a solvent such as THF (T. Shono, Y. Matsumura, J. Org. Chem., 1984, 48, 300) Subsequent reaction with hydrazine hydrate and KOH in ethylene glycol at elevated temperatures provides the amine 21. Compound 20 may also be converted to its 2,2,2-trichloroethyloxycarbamate derivative by stirring with 2,2,2-trichloroethylchloroformate in a solvent such as acetonitrile (V. H. Rawal, R. J. Jones, J. Org. Chem., 1987, 52, 19). This derivative is then converted to amine 21 by reaction with zinc powder in acetic acid a slightly elevated temperatures such as at 40° C.

SCHEME 5

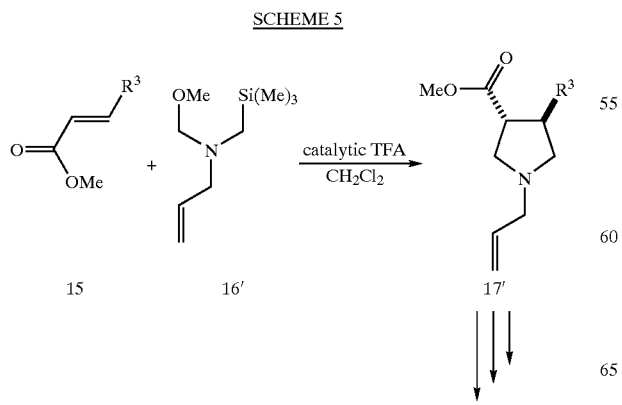

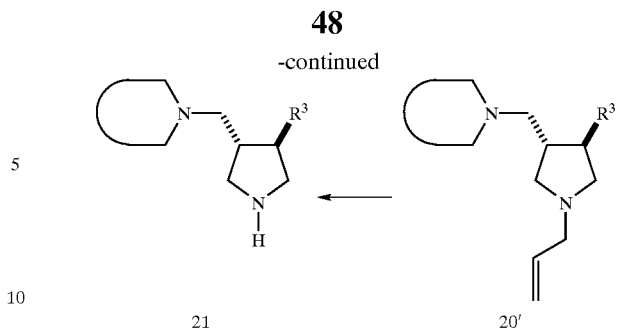

Scheme 5 describes a modification of Scheme 3 when substituents are not compatible with hydrogenolysis of the benzyl group of compound 20. In this variation, treatment of a trans-cinnamic ester 15 with N-allyl-N-methoxymethyl-N-(trimethylsilyl)-methylamine (16') according to procedures described in Scheme 3 provides N-allylpyrrolidine derivative 17'. The reagent N-allyl-N-methoxymethyl-N-(trimethylsilyl)-methylamine is prepared after procedures described by Padwa et al (J. Org. Chem. 1985, 50, 4006 and J. Org. Chem. 1987, 52, 235) Subsequent elaboration as described in Scheme 3 gives compound 20'. The allyl group of compound 20' is removed by heating with Wilkinson's catalyst ([Rh(PPh$_3$)$_3$Cl] in a solvent such as 85% CH$_3$CN in water.

SCHEME 6

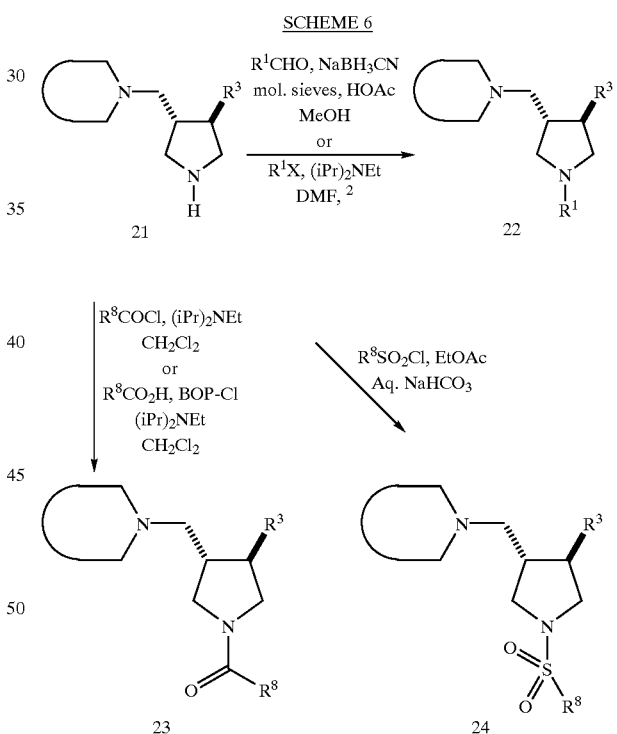

The unsubstituted pyrrolidine 21 may be further functionalized as shown in Scheme 6. Reductive amination with suitable aldehydes under standard conditions provides the tertiary amine 22. The pyrrolidine nitrogen may be alkylated with a suitable halide, methanesulfonate, p-toluenesulfonate, etc. carried out under standard conditions to provide N-alkylated pyrrolidine 22. Alternatively, compound 22 is acylated with, for example, acid chlorides or bromides, or activated esters utilizing a variety of the standard coupling conditions to give amide 23. For example, reaction of compound 22 and a carboxylic acid with BOP—

Cl and triethylamine in a solvent such as methylene chloride is a commonly used procedure. The sulfonamide 24 is prepared under standard conditions by exposing 21 to an alkyl or aryl sulfonyl chloride in the presence of a suitable base to neutralize the formed hydrogen chloride.

SCHEME 7

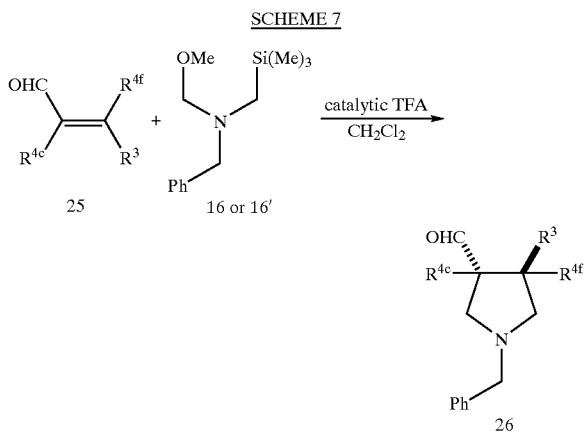

Compounds possessing geminal substituents on positions 3 or 4 (or on both C3 and C4) of the pyrrolidine ring are prepared by the method shown in Scheme 7. Cycloaddition of unsaturated aldehyde 25 with reagent 16 or 16' as described in Schemes 3 or 5 provides pyrrolidine aldehyde 26. Further elaboration of 26 can be achieved as described in the previous Schemes.

SCHEME 8

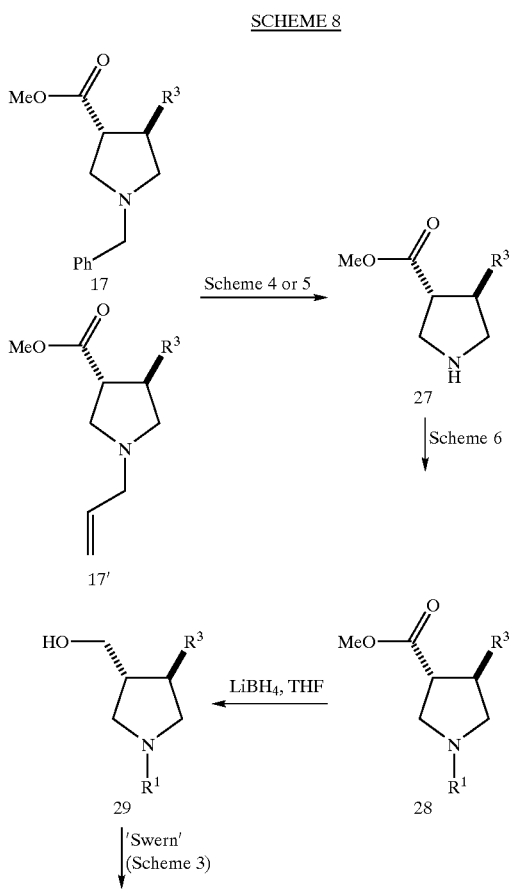

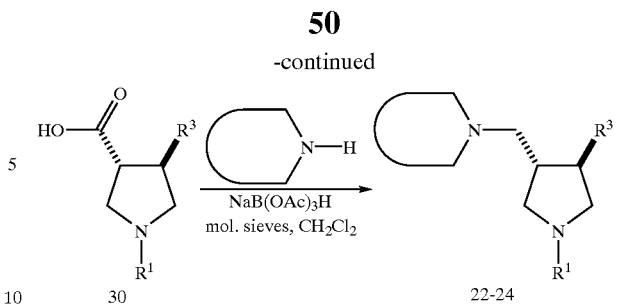

An alternative approach to the synthesis of chemokine modulators is described in Example 8. Ester derivatives 17 (Scheme 3) or 17' (Scheme 5) are first debenzylated or deallylated by procedures described in Schemes 3, 4 or 5 to give secondary amine derivative 27. Compound 27 can then be elaborated as described in Scheme 6 to provide compound 28. The ester group of 28 can be selectively reduced with a reagent such as lithium borohydride in THF to give the alcohol 29 which is then converted to aldehyde 30 under Swern conditions as described in Scheme 3. Aldehyde 39 is then converted to derivative 22 (or 23 or 24) by reductive amination (Scheme 3).

SCHEME 9

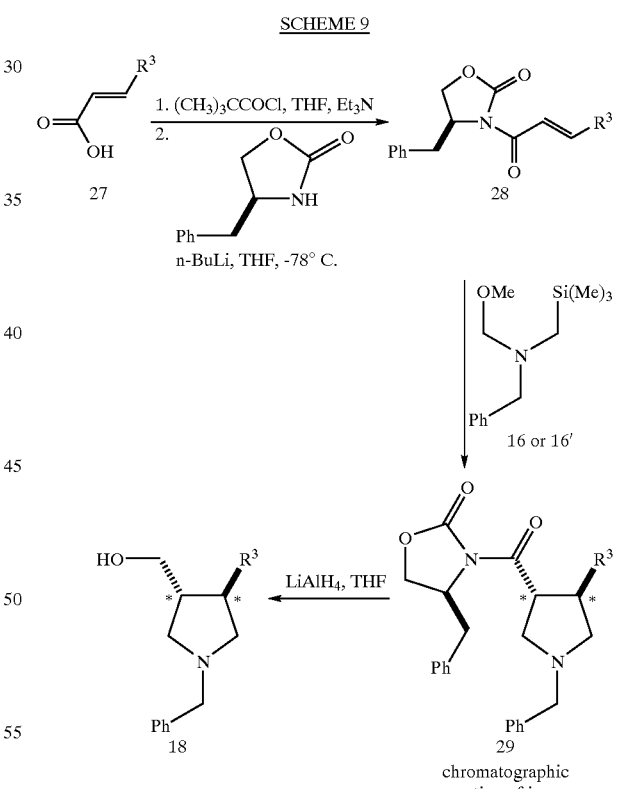

The preparation of optically active compounds described in Scheme 9 follows procedures described by Ma et.al., (*Tetrahedron: Assymmetry* 1997, 8, 883). Reaction of a trans-acrylic acid with oxalyl chloride or pivaloyl chloride and triethylamine in THF provide the mixed anhydride intermediate. This is then treated with the lithium salt of an appropriate chiral auxiliary such as (S)-benzyl-2-oxazolidinone in THF at reduced temperatures, such as −78° C. to give amide 28. This acrylamide is then reacted with N-benzyl-N-methoxymethyl-N-(trimethylsilyl)-methylamine (16) or N-allyl-N-methoxymethyl-N-(trimethylsilyl)-methylamine (16') as described in Schemes 3 and 5, respectively, to give pyrrolidine intermediate 29 or the corresponding N-allyl derivative. Modest diastereoselectivity is achieved in these cyclizations as shown by Ma et al. However, the separate optically active isomers may be easily obtained by simple chromatography on silica gel. Reaction of the selected diastereomer 29 with LiAlH$_4$ in THF at 0° C. provides the optically active version of compound 18 which is further elaborated as described in the previous Schemes The various piperidine derivatives, when not commercially available, are prepared as described in the following Schemes.

SCHEME 10

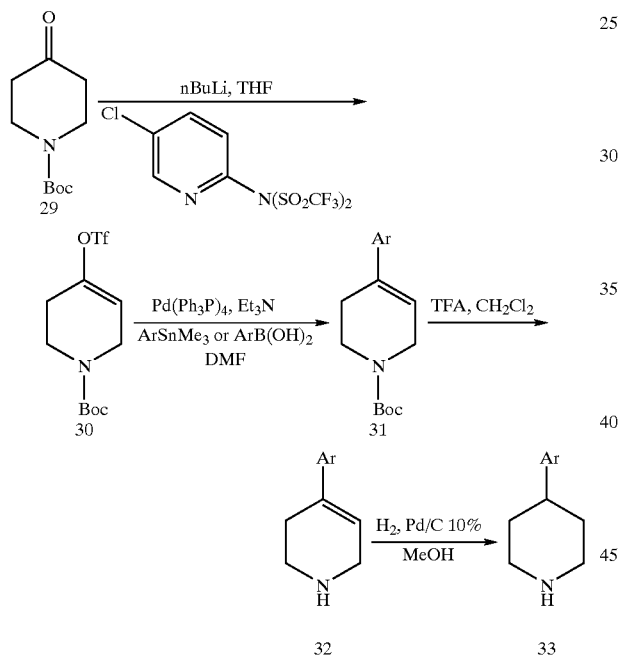

The synthesis of 4-arylpiperidine groups is presented in Scheme 10. Enolate formation of the 4-piperidone derivative 29 followed by formation of the vinyl triflate with either 2-[N,N-bis(trifluoromethyl sulfonyl)amino]-5-chloropyridine or with N-phenyltriflimide provides triflate ether 30. Palladium-mediated coupling with a suitable aryl stannane or aryl boronic acid provides the tetrahydropyridine derivative 31. The Boc protecting group can be removed with TFA to give amine 32 which is then hydrogenated under standard conditions to give piperidine 33. Alternatively, tetrahydropyridine derivative 31 is first hydrogenated and then deprotected. Modification of the aryl group of compound 31 or 33 is achieved using appropriate chemical modification schemes.

SCHEME 11

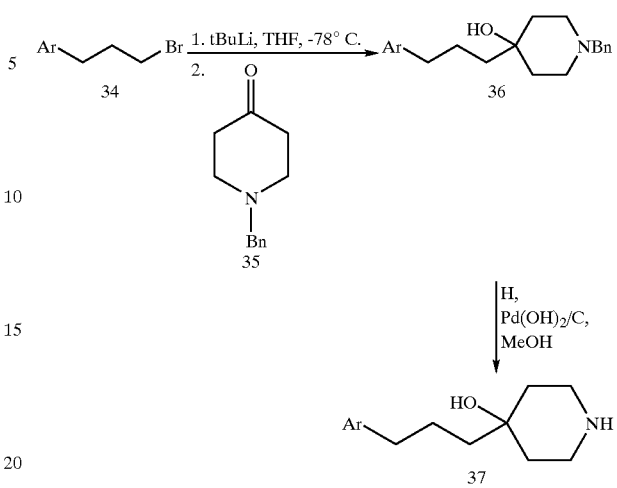

A method of preparing 4-(3-aryl-1-propyl)-4-hydroxypiperidine derivatives is described in Scheme 11. A suitable 3-arylpropyl halide 34 in THF at −78° C. is reacted with a base such as t-butyl lithium. This is then reacted with a protected 4-piperidone derivative such as N-benzyl-4-piperidone 35 to give the arylpropylpiperidine derivative 36. Deprotection by hydrogenation with Pd(OH)$_2$/C (Pearlman's catalyst) gives piperidine derivative 37 which can be reacted with compound 19 as described in Scheme 3.

SCHEME 12

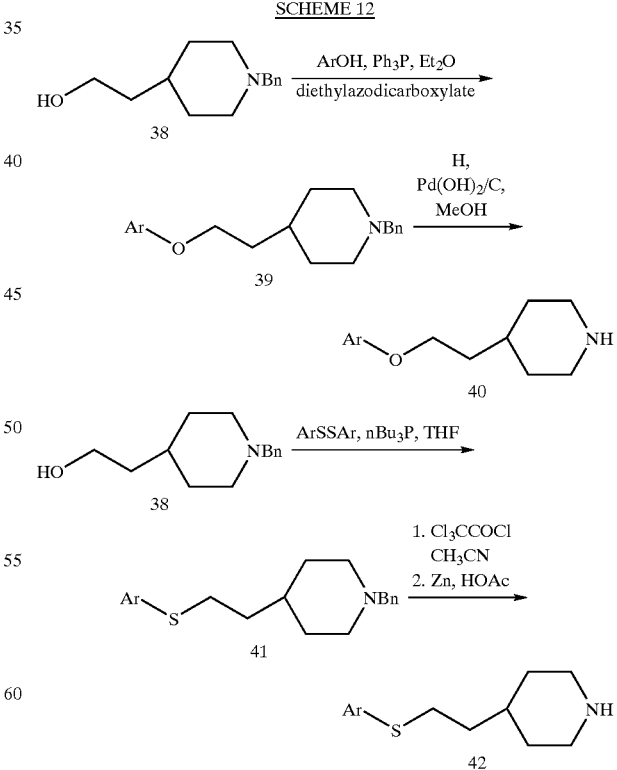

A method of preparing 4-aryloxyethylpiperidine derivatives is described in Scheme 12. Reaction of commercially available N-benzyl-4-hydroxyethylpiperidine with an appropriate aryl alcohol under standard Mitsunobu conditions, followed by deprotection gives the corresponding piperidine derivative. The corresponding mercapto derivative is prepared by reaction of compound 38 with an aryldisulfide and tri-n-butylphosphine in THF with heating at reflux to give compound 41. Compound 41 is then converted to compound 42 as described in Scheme 4.

SCHEME 13

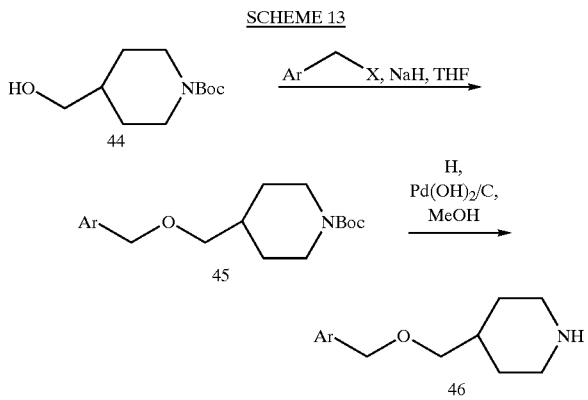

Compound 45 can be prepared prepared (Scheme 13) by alkylation of compound 44 (prepared from isonipecotic acid) with an arylmethylhalide, bromide, iodide, methanesulfonate, p-toluenesulfonate, or trifluoromethane-sulfonate in a solvent such as THF with a base such as sodium hydride. Subsequently, compound 45 is deprotected by reaction with trifluoroacetic acid in a solvent such as methylene chloride to give compound 46.

SCHEME 14

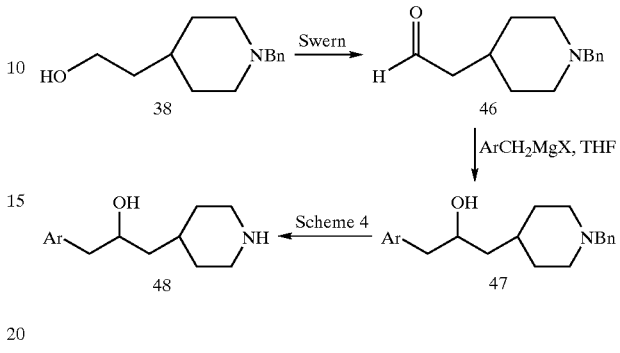

In Scheme 14, the preparation of 4-(3-aryl-2-hydroxypropyl) piperidines is described. Compound 38 is converted to aldehyde 46 by the Swern-type conditions (oxalyl chloride, DMSO, $Et_3N$). Reaction of compound 46 with Grignard reagents or other related nucleophiles gives hydroxy derivative 47. Compound 47 is then converted to piperidine 48 by procedures described in Scheme 4.

SCHEME 15

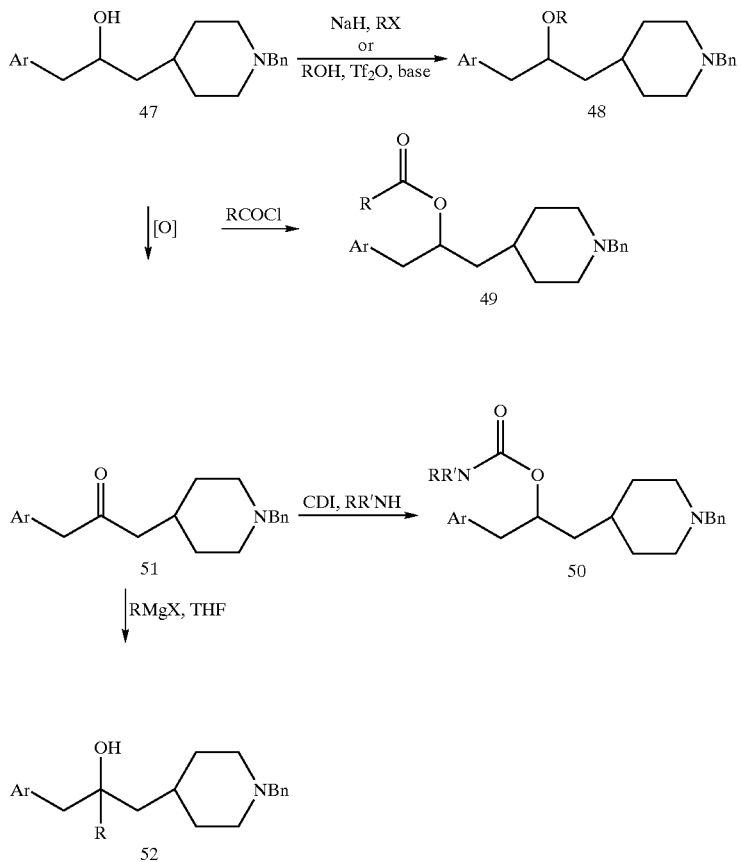

Compound 47 can be further derivatized as depicted in Scheme 15. Ether derivatives 48 can be prepared by reaction with an alkylhalide, tosylate or triflate in the presence of a base such as sodium hydride in an aprotic inert solvent such as THF. Alternatively, an excess of silver oxide ($Ag_2O$) is used in place of the base. In an alternate procedure, reaction of an alcohol with trifluoromethane sulfonic anhydride ($Tf_2O$, triflic anhydride) in dichloromethane at reduced temperature, preferably –78° C. gives the preformed triflate. To this solution is added compound 47, the reaction mixture is warmed to room temperature and stirring is continued until reaction is complete.

Esters (compound 49) can be prepared by reaction of a pre-formed carboxylic acid chloride with compound 47 in a basic solvent such as pyridine or triethylamine. The acid chlorides, when not purchased, are prepared by stirring the carboxylic acids in reagents such as oxalyl chloride or thionyl chloride. C4 sulfonate derivatives are prepared in a similar manner by reaction with sulfonyl chlorides.

C4 carbamate and carbonate derivatives (compound 52) are prepared by first reacting compound 47 with carbonyldiimidazole (CDI) to obtain the imidazolecarbonyl intermediate which is then reacted with an amine ($R^1R^2NH$) or an alcohol to give the corresponding carbonate or carbamate derivatives.

Compound 47 can be oxidized to the corresponding ketone 51 by any number of standard conditions. It can then be reaction with Grignard reagents or related nucleophiles (as in Scheme 14) to give the tertiary hydroxy derivative 52. This alcohol can then be further modified as described in this scheme.

In Scheme 16, the preparation of 4-(3-phenyl-3-hydroxypropyl) piperidines is described. Oxidation of compound 44 under Swern conditions gives aldehyde derivative 53. It is then reacted with diethyl(2-aryl-2-oxoethyl) phosphonate and a base such as KOtBu in a solvent such as THF to give the conjugated ketone derivative 54. Reduction with hydrogen in the presence of Pd/C preferentially at 50 psi gives the hydroxy compound 55 which is converted to piperidine derivative 56 as previously described. Prior to deprotection, compound 55 can be further modified as depicted in Scheme 15.

SCHEME 17

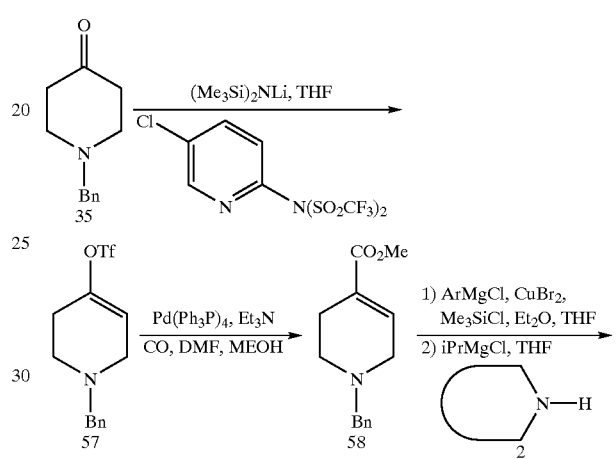

SCHEME 16

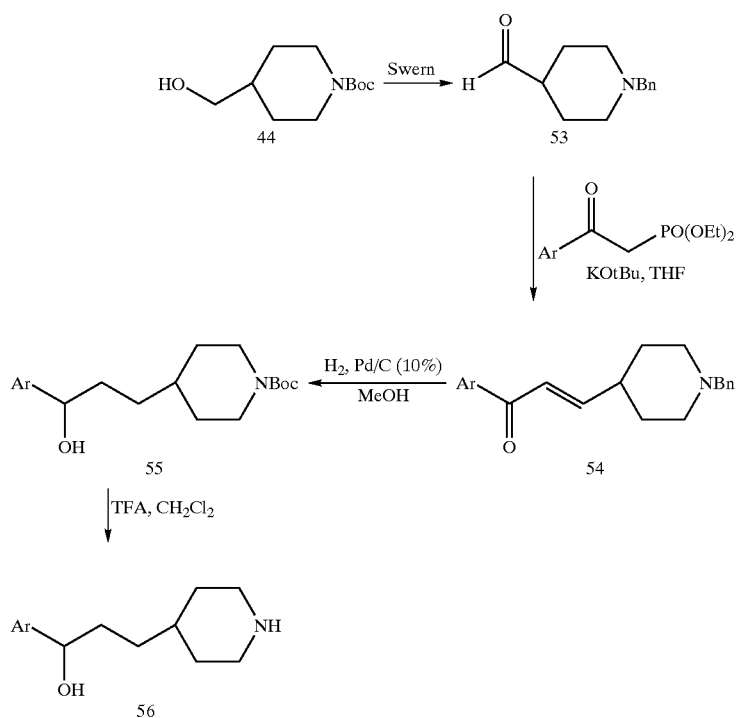

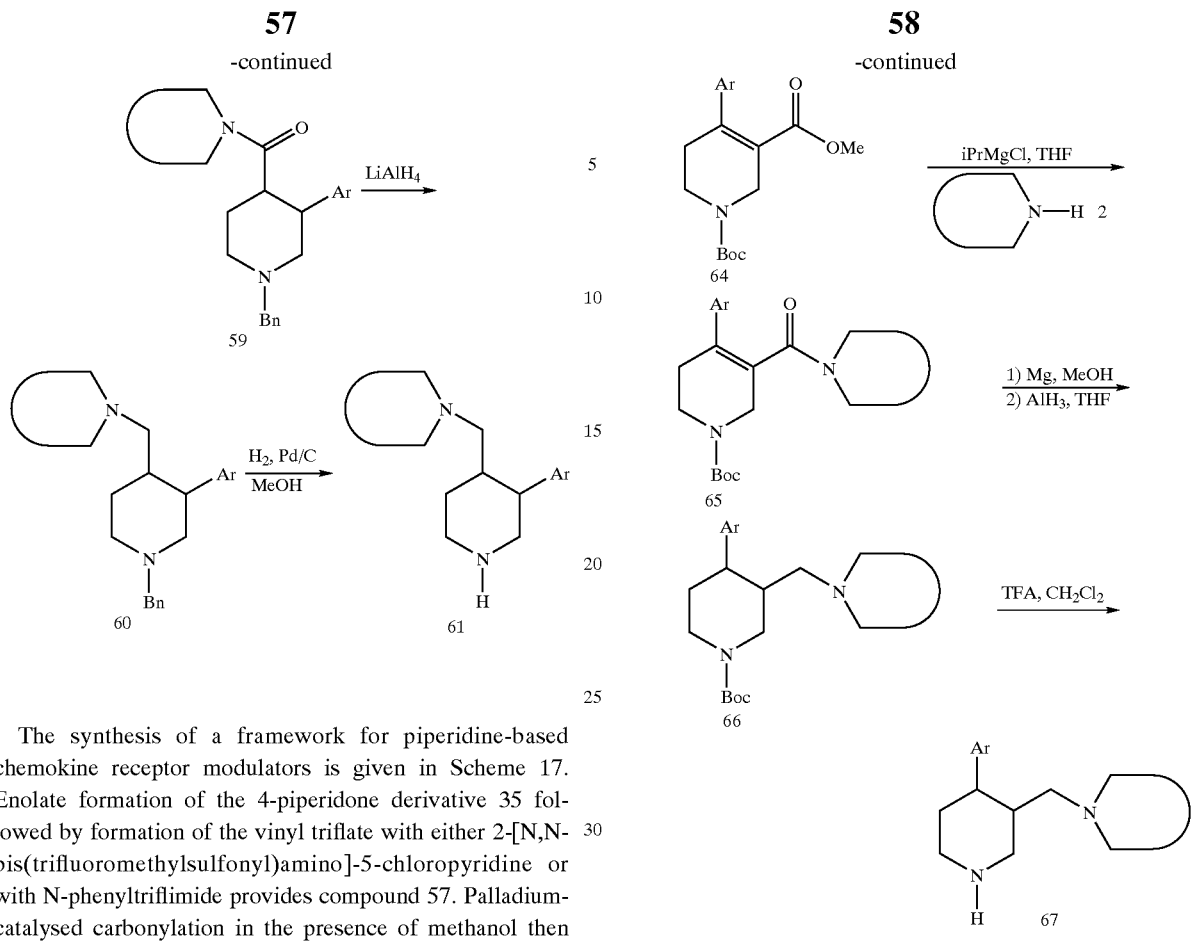

The synthesis of a framework for piperidine-based chemokine receptor modulators is given in Scheme 17. Enolate formation of the 4-piperidone derivative 35 followed by formation of the vinyl triflate with either 2-[N,N-bis(trifluoromethylsulfonyl)amino]-5-chloropyridine or with N-phenyltriflimide provides compound 57. Palladium-catalysed carbonylation in the presence of methanol then affords unsaturated ester 58. Conjugate addition of an aryl magnesium halide reagent in the presence of a copper catalyst and chlorotrimethylsilane to this species, followed by treatment with the magnesium salt of a suitable cyclic amine, then yields amide 59. Reduction with LiAlH$_4$ or borane.THF affords the tertiary amine 60, which is hydrogenated under standard conditions to the secondary piperidine 61. This compound is alkylated, acylated or sulfonated by analogy to the conditions described for compound 21 in Scheme 4.

SCHEME 18

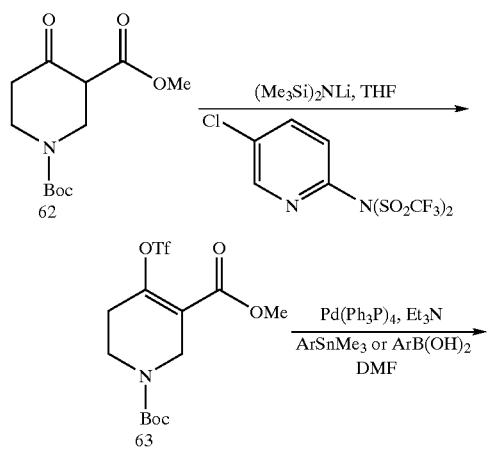

Synthesis of a piperidine derivative with an alternate presentation of the 3- and 4-substituents is given in Scheme 18. Formation of the enolate of ketoester 62 (prepared from commercially available 3-carbomethoxy-4-oxopiperidine and Boc anhydride) followed by addition of either 2-[N,N-bis(trifluoro-methylsulfonyl)amino]-5-chloropyridine or N-phenyltriflimide provides vinyl triflate 63. Palladium-mediated coupling with a suitable aryl stannane or aryl boronic acid provides unsaturated ester 64. Treatment of this compound with the magnesium salt of a suitable cyclic amine then affords amide 65, which can be reduced successively with magnesium metal in methanol followed by alane in THF, to provide the tertiary amine 66. Removal of the Boc group under standard acidic conditions yields secondary amine 67, which can be alkylated, acylated or sulfonated by analogy to the conditions described in Scheme 6.

SCHEME 19

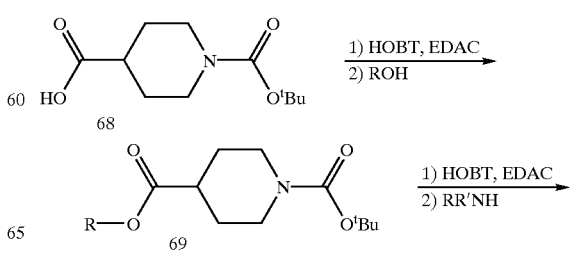

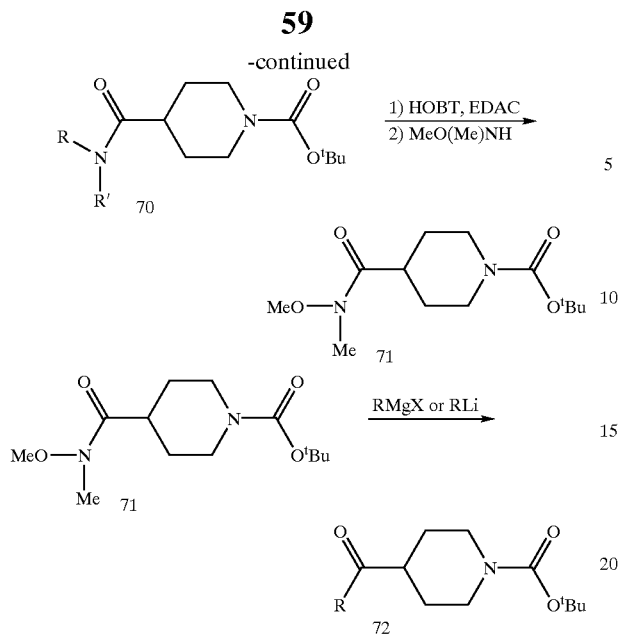

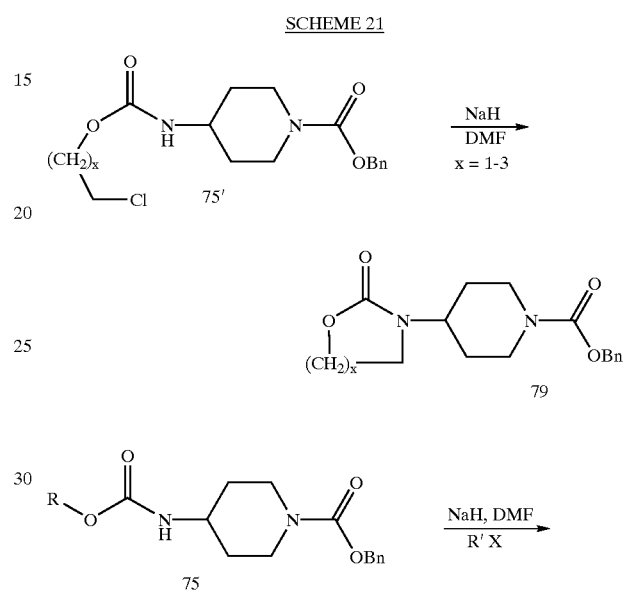

The cyclic amine II employed in the preceding Schemes can be obtained commercially in many cases or is prepared by a number of procedures. For example, as shown in Scheme 19, compound 68, the N-t-butoxycarbonyl protected form of isonipecotic acid (4-piperidine-carboxylic acid) is activated under standard conditions, for example with a carbodiimide, and converted into ester 69 or amide 70. Alternatively, acid 68 is converted into the N-methyl-N-methoxy amide, 71, which upon reaction with organomagnesium and organolithium reagents forms the ketone 72. The Boc group of 69, 70 and 72 is removed under acidic conditions to provide the corresponding secondary amines.

Alternatively, CBZ-protected piperidine 73 is allowed to react with oxalyl chloride and then sodium azide, to provide the corresponding acyl azide, which can then be thermally rearranged to isocyanate 74 (Scheme 20). Compound 74 is treated with an alcohol ROH or an amine RR'NH to form carbamate 75 or urea 76, respectively, each of which is deprotected with hydrogen in the presence of palladium on carbon to secondary amines 77 or 78.

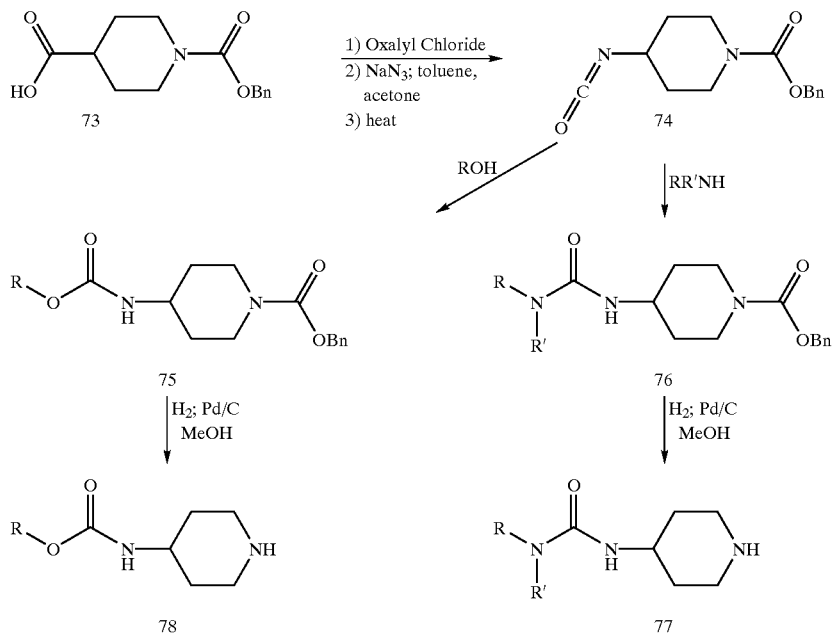

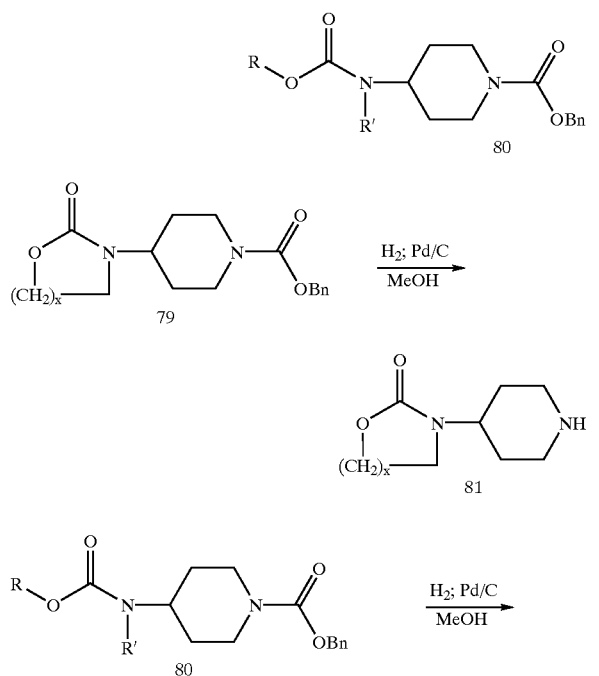

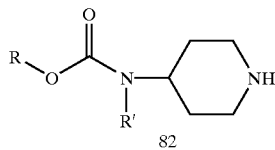

If the carbamate 75 has R=—$(CH_2)_xCH_2Cl$, where x=1–3, then treatment with a suitable base, such as sodium hydride, lithium hexamethyldisilazide or potassium t-butoxide, can induce cyclization to compound 79 (Scheme 21). For other R groups, carbamate 75 is treated with an alkylating agent R'X, where R'=primary or secondary alkyl, allyl, propargyl or benzyl, while X=bromide, iodide, tosylate, mesylate or trifluoromethanesulfonate, in the presence of a suitable base, such as sodium hydride, lithium hexamethyldisilazide or potassium t-butoxide, to give derivative 80; a similar process can be employed for urea 76. In each case, removal of the CBZ protecting group under standard conditions provides the secondary amines 81 and 82.

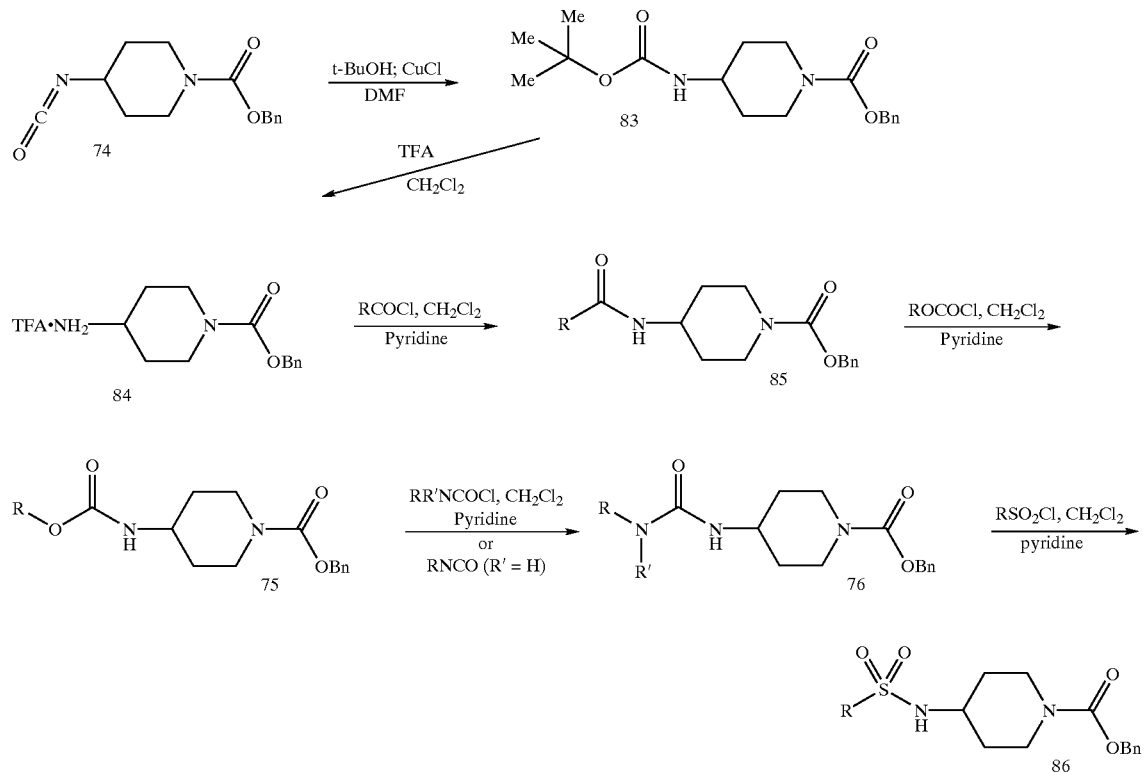

Additional derivatization of a piperidine with nitrogen functionality at C4 is carried out as shown in Scheme 22. For example, if the ring nitrogen is protected with a CBZ group, as with isocyanate 74, treatment with tert-butyl alcohol in the presence of copper(I) chloride, provides Boc derivative 83. This compound is selectively deprotected to the free amine 84. This amine is acylated with an acid chloride, a chloroformate, an isocyanate, or a carbamyl chloride, to provide compounds 85, 75 or 76. Alternatively, amine 84 is sulfonated with an alkyl or arylsulfonyl chloride, to give sulfonamide 86. Compounds 85 and 86 optionally is alkylated under the conditions given above. As shown in Scheme 21, removal of the CBZ group under reductive conditions gives the desired secondary amines.

SCHEME 24

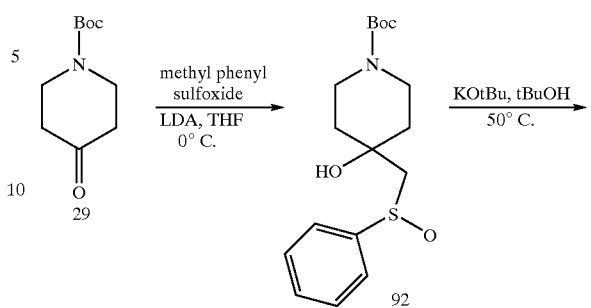

SCHEME 23

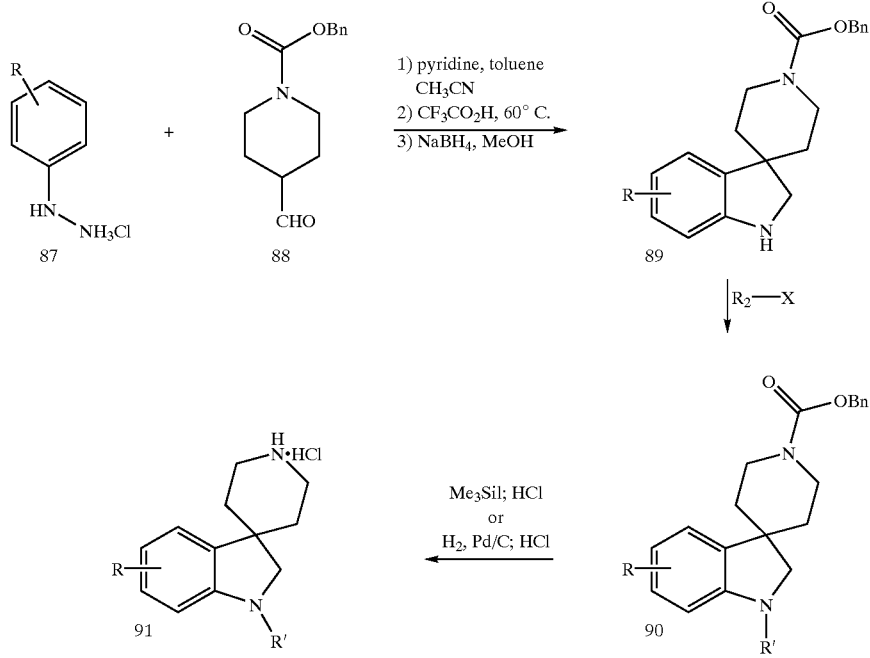

Substituted spiro(indoline-3,4'-piperidine) derivatives can be prepared as shown in Scheme 23 starting from the substituted phenylhydrazine 87 and the aldyhyde 88. Following the Fischer indole reaction and reduction of the intermediate imine with a mild reducing agent such as sodium borohydride, the indoline 89 can be combined with an electrophile such as an acyl chloride or a sulfonyl chloride. The protecting group on compound 90, for example a benzyloxycarbonyl group, can be removed by treatment with hydrogen in the presence of palladium on carbon or by exposure to trimethylsilyl iodide, to give the deprotected substituted spiro(indoline-3,4'-piperidine) 91.

-continued

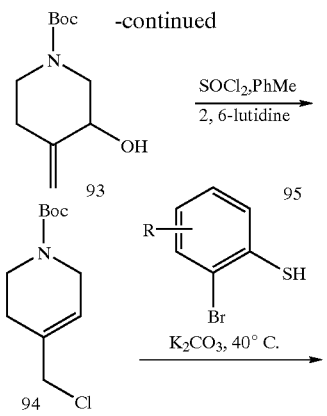

-continued

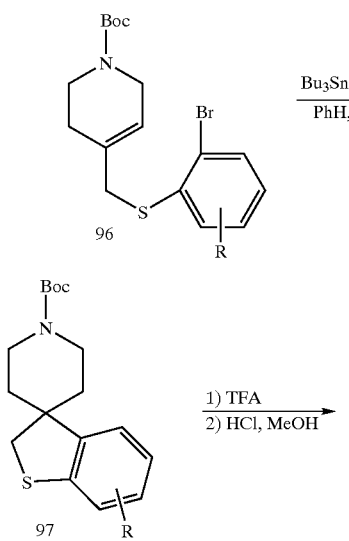

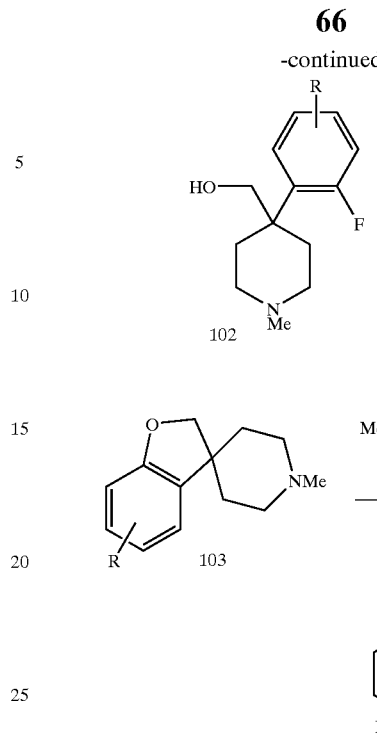

Preparation of spiro(2,3-dihydrobenzothiophene-3,4'-piperidine) derivatives is shown in Scheme 24. Reaction piperidone 29 with the lithium salt of methyl phenyl sulfoxide affords adduct 92. Base-mediated elimination-rearrangement and basic cleavage provides the allylic alcohol 93. The alcohol is converted to rearranged allylic chloride 94 with thionyl chloride in toluene in the presence of 2,6-lutidine as a proton scavenger. Displacement of the chloride with the 2-bromothiophenol 95 provides allylic sulfide 96, which can be cyclized under radical conditions to give spiro(2,3-dihydrobenzothiophene-3,4'-piperidine) 97. Cleavage of the t-butoxycarbonyl group under standard conditions, such as trifluoroacetic acid, then provides the desired spirocycle 98.

Spiro(2,3-dihydrobenzofuran-3,4'-piperidine) derivatives are prepared as illustrated in Scheme 25. Treatment of an appropriately substituted ester of 2-fluorophenylacetate 99 with mechlorethamine hydrochloride 100 under basic conditions provides piperidine 101, which on treatment with a strong reducing agent such as lithium aluminum hydride produces the corresponding 4-(hydroxymethyl) compound 102. Cyclization with base provides benzofuran 103, and cleavage of the N-methyl group is then carried out using 1-chloroethyl chloroformate or other suitable N-demethylating agents, to provide the desired intermediate 104.

SCHEME 25

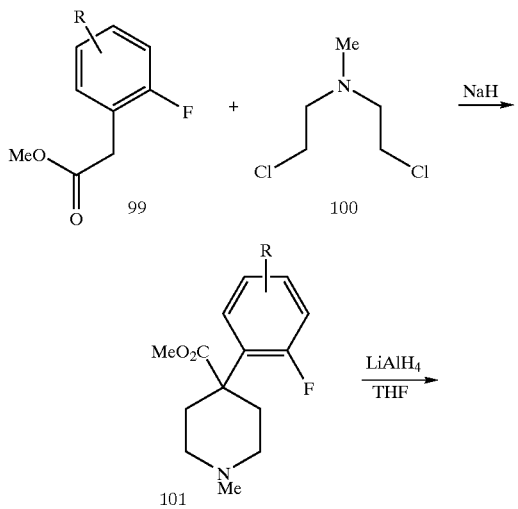

SCHEME 26

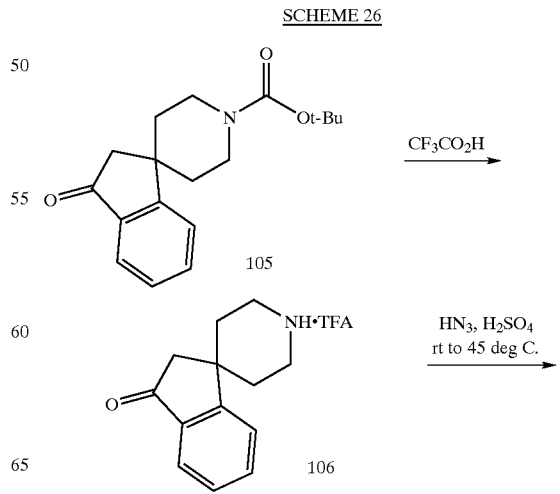

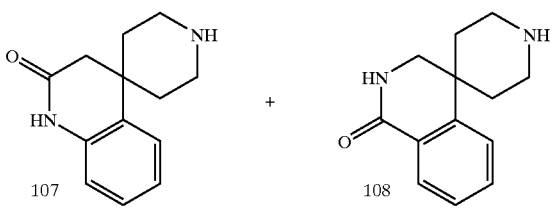

ture; more specifically as described in U.S. Pat. No. 5,057,517; U.S. Pat. No. 4,242,344; *J. Org. Chem*, 1974, 39, 2143 and *J. C. S. Perkin I*, 1980, 506; *J. Org. Chem.* 1963, 28, 1753; *J. Heterocyclic Chem.*, 1982, 19, 1207; *Arch. Int. Pharmacodyn.* 1986, 280, pp302–313; Meurer, L. C. et al., *J. Med. Chem.*, 1992, 35, 3845–3857. None of these published compounds are disclosed to be chemokine receptor modulators. Alternatively, the piperazine substrates is prepared as illustrated in Schemes 27–30.

Spiro(2-oxo-1,2,3,4-tetrahydroquinoline-4,4'-piperidine) and spiro(1-oxo-1,2,3,4-tetrahydroisoquinoline-4,4'-piperidine) are prepared as shown in Scheme 26. Starting from the spiro(2-oxoindane-3,4'-piperidine) LXXXVIII (described in Claremon, D. A. et al, European Patent 0 431 943 943 A2, Evans, B. E. et al., U.S. Pat. No. 5,091,387, Davis, L. et al, U.S. Pat. No. 4,420,485, all of which are incorporated by reference, and Parham et al, *Journal of Organic Chemistry*, 41, 2628 (1976)), deprotection of the piperidine nitrogen is carried out by treatment with acid, for example trifluoroacetic acid, to provide ketone 106. After protection as the trifluoroacetamide, the product is exposed to hydrazoic acid in the presence of sulfuric acid. Heating of this mixture effects a Schmidt rearrangement, to provide both tetrahydroquinoline 107 and the tetrahydroisoquinoline 108. These spiro compounds are then separated and coupled to functionalized aldehydes by the methodology given above.

Cyclic amines (compound 2) which are 4-arylpiperazines functionality are prepared using methods described in the following Schemes. Starting materials are made from known procedures or as illustrated. Substituted purines are prepared as disclosed in U.S. Pat. No. 5,057,517; imidazo(1.2-a)pyrazinyl, as disclosed in U.S. Pat. No. 4,242,344; (1,2,4)-triazolo(1.5-a)pyrazinyl as disclosed in *J. Org. Chem*, 1974, 39, 2143 and *J.C.S. Perkin I*, 1980, 506; 1,7-naphthyridinyl as disclosed in *J. Org. Chem.* 1963, 28, 1753; furo(3.2-c)pyridinyl as disclosed in *J. Heterocyclic Chem.*, 1982, 19, 1207; and substituted 6-H-7,8-dihydro-thiopyrano(3.2-d)pyrimidyl as disclosed in *Arch. Int. Pharmacodyn.* 1986, 280, pp302–312.

Optionally, Compound III formed in the alkylation step is further modified in subsequent reactions. In one illustration of such an approach, the piperazine fragment may contain in nitro group, which is reduced to the amine after the coupling step. The resulting amine is further modified by acylation to provide the desired compounds. The piperazine fragment may also contain a protecting group such as a benzyl ester or a t-butyl ester. After reductive amination the protecting group is removed and the resulting acid is further reacted to provide additional analogs. Alternatively, the aldehyde portion may also contain a protecting group such as a t-butoxycarbonyl for an amino function. After reductive amination, the t-butoxycarbonyl group is removed by treatment with a strong acid such as trifluoroacetic acid, formic acid or hydrochloric acid and the resulting amine may be acylated to provide other analogs.

The piperazine starting materials used in the coupling reaction are prepared using methods described in the litera-

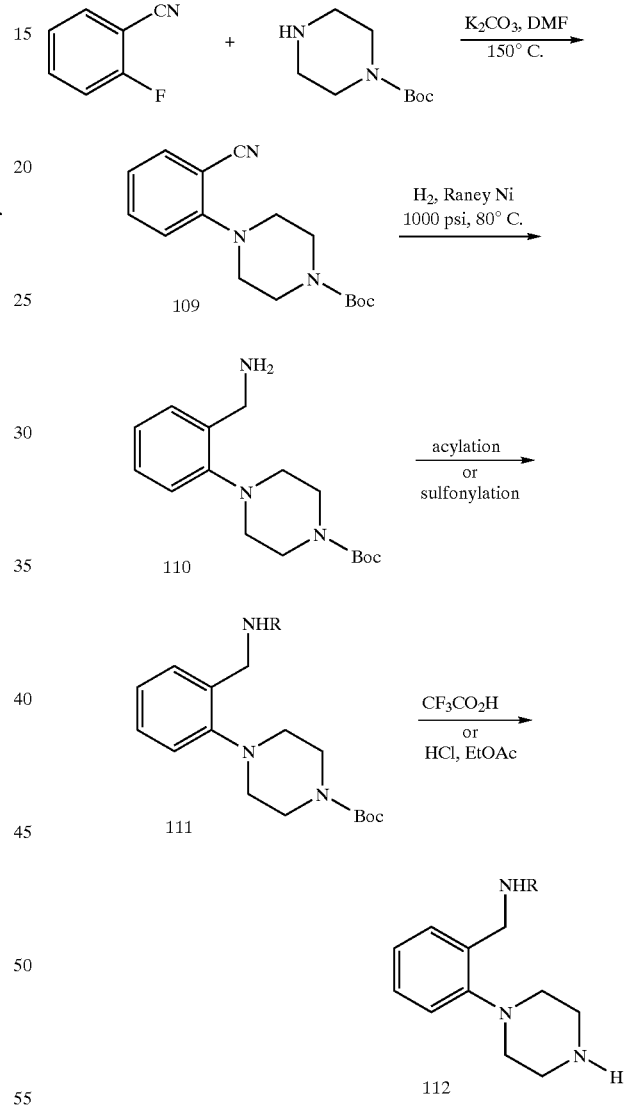

Substituted 4-arylpiperazines are prepared from appropriate fluorobenzene derivative as shown in Scheme 27. Thus, reaction of 2-fluorobenzonitrile with 1-t-butoxycarbonylpiperazine in the presence of a base such as $K_2CO_3$ gives 1-t-butoxycarbonyl-4-(2-cyanophenyl)-piperazine (compound 109. Reduction of the cyano group by the hydrogenation in the presence of Raney nickel or by other known methods gives benzyl amine 110, which is acylated or sulfonylated, to provide piperazine 111. The t-butoxycarbonyl protecting group is removed under acidic conditions, for example by treatment with trifluoroacetic acid or anhydrous HCl to give 1-unsubstituted piperazine 112 which can be used in the reductive amination or alkylation steps described in Scheme 1. Similar reactions using 2-chloro-nitrobenzene in the place of 2-fluorobenzonitrile provides compounds containing a substituted aniline. Analogs containing a benzoic acid or its derivatives are prepared by substituting 2-fluorobenzoic acid in this sequence.

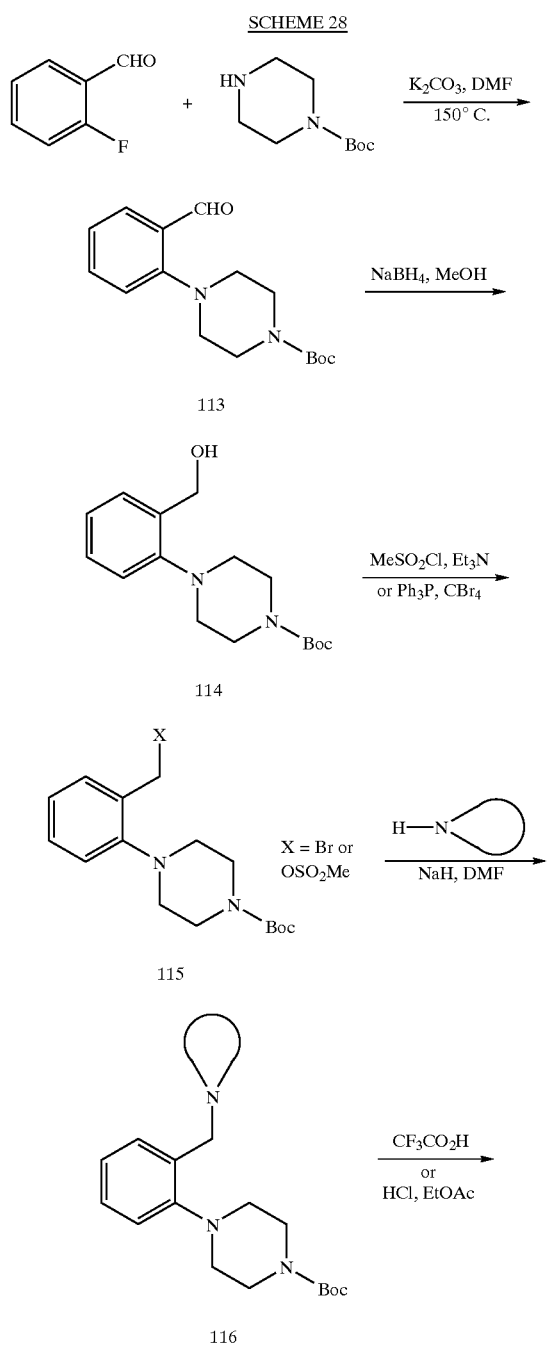

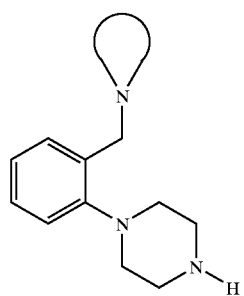

Arylpiperazine derivatives containing heterocyclic substituents are synthesized as shown in Scheme 28. Reaction between 2-fluorobenzaldehyde and 1-t-butoxycarbonylpiperazine gives 1-t-butoxycarbonyl-4-(2-formylphenyl)-piperazine compound 113. Reduction of this aldehyde and treatment of the alcohol 114 with methanesulfonyl chloride gives 115 (X=mesylate), while treatment of 114 with triphenylphosphine and carbon tetrabromide gives 115 (X=bromide). Displacement of the leaving group by a heterocycle such as imidazole in the presence of a base provides piperazine 116. Removal of the t-butoxycarbonyl protecting group under standard anhydrous acidic conditions furnishes compound 117 which is used in the coupling reactions described in Scheme I.

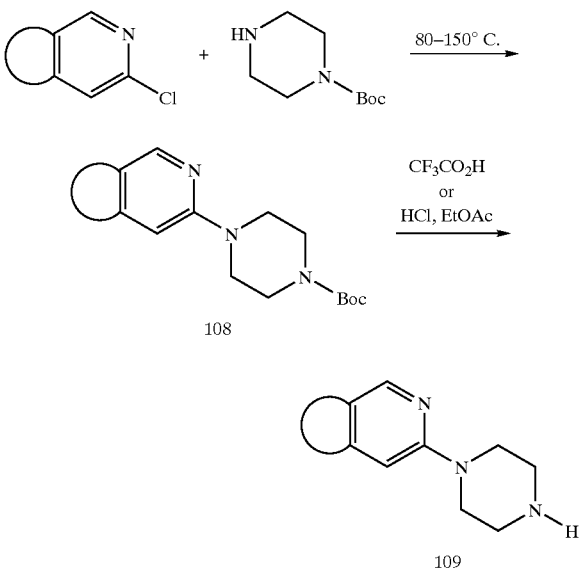

Preparation of piperazines containing a heteroaryl substituent is outlined in Scheme 29. Reaction of 1-t-butoxycarbonyl-piperazine with a chloro substituted heteroaromatic compound such as 8-chloro-1,7-naphthyridine or 8-chloro-(1,2,4)-triazolo(1,5-a)pyrazine gives N-protected piperazine 108. Removal of the t-butoxycarbonyl protecting group under standard conditions by treatment with acid provides piperazine 109 for use in the coupling steps outlined in Scheme 1.

SCHEME 30

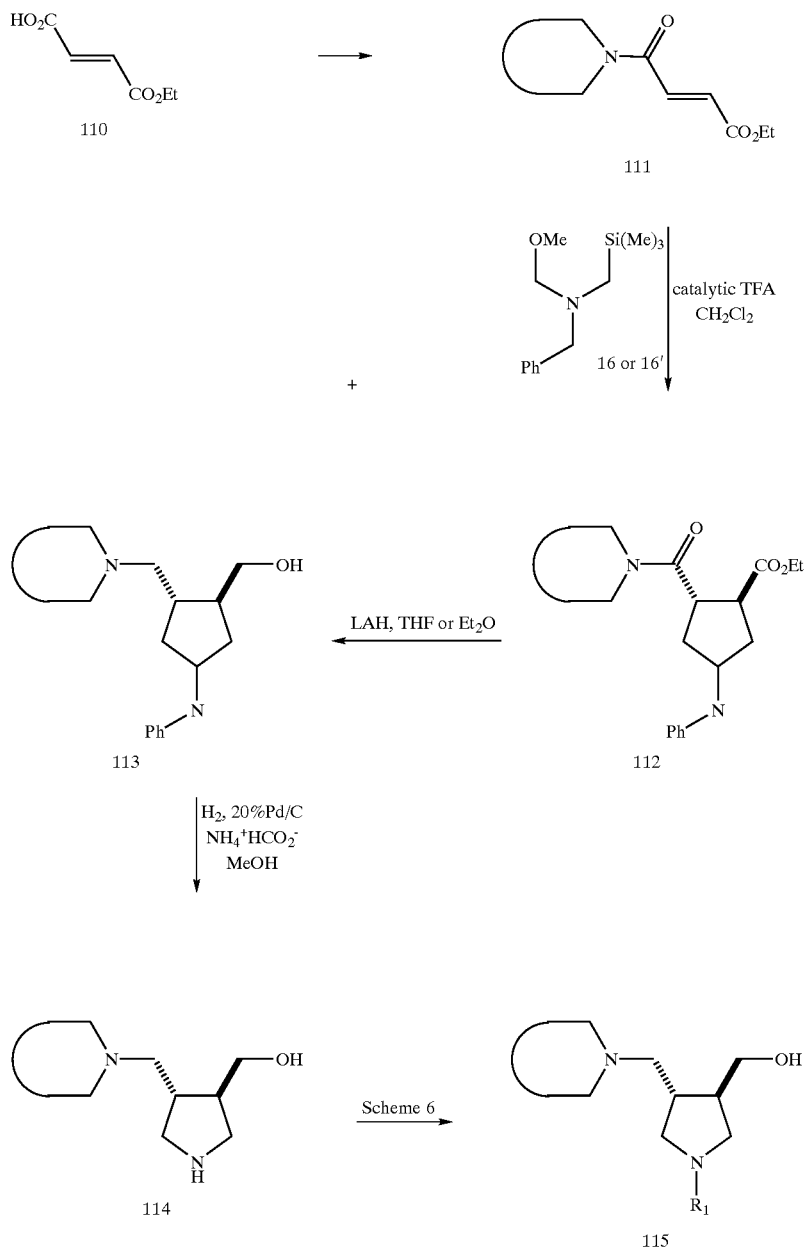

A variation of Reaction Schemes 1 to 9 is described in Reaction Scheme 30. Monoethylsuccinate 110 is coupled with cyclic amine 2 as described in Reaction Scheme 1 to give amide 111. Amide 111 is cyclized with N-benzyl-N-methoxymethyl-N-(trimethylsilyl)-methylamine (16) or N-allyl-N-methoxymethyl-N-(trimethylsilyl)-methylamine (16') as described in Reaction Schemes 3 or 5 to give pyrrolidine derivative 112. Reduction of compound 112 with LAH in THF or ether gives primary alcohol 113. The protecting group on the nitrogen of compound 113 can be removed as described in Reaction Scheme 3 to give compound 114. In the case where the group is allyl, it is removed as described in Reaction Scheme 5. The nitrogen position of compound 114 can be functionalized as described in Reaction Scheme 6, when the conditions are compatible with the primary alcohol. For example, compound 114 is reacted with an acid chloride in a solvent such as methylene chloride. To the reaction mixture is then added methanol or ethanol with added stirring to remove any unintended acylation of the primary alcohol.

SCHEME 31

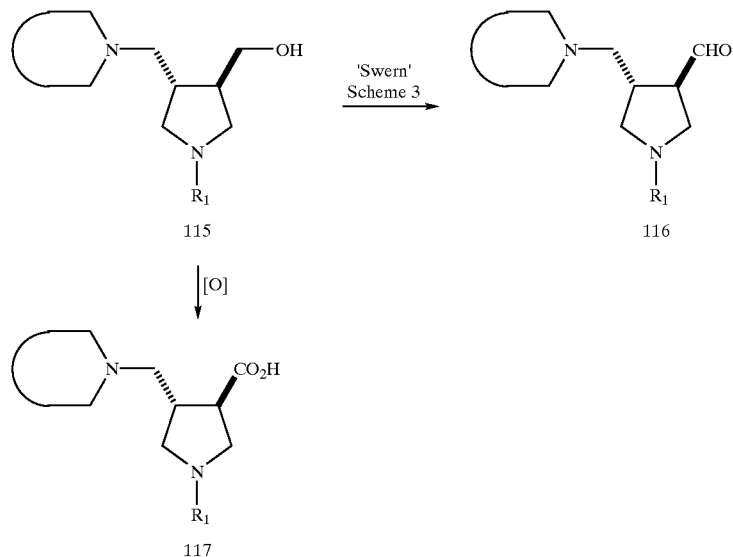

In Reaction Scheme 31, compound 31 is oxidized to aldehyde derivative 116 utilizing Swern-type conditions described in Scheme 3. Compound 115 can also be oxidized to acid derivative 117 utilizing various chromium trioxide-based reagents (see March J. "Advanced Organic Chemistry", 4th ed., John Wiley & Sons, New York, pp. 1167–1171 (1992)).

Primary alcohol 115 may be further modified in numerous ways including conversion to ether 118, ester 119 and carbamate 120 as described in Reaction scheme 15. Alternatively, aryl ethers are prepared using triaryl bismuthine reagents (Sinclair et. al., Bioorg. Med. Chem. Letters 1995, 5, 1035 and references cited therein). Further modifications can be achieved utilizing standard methodologies.

SCHEME 32

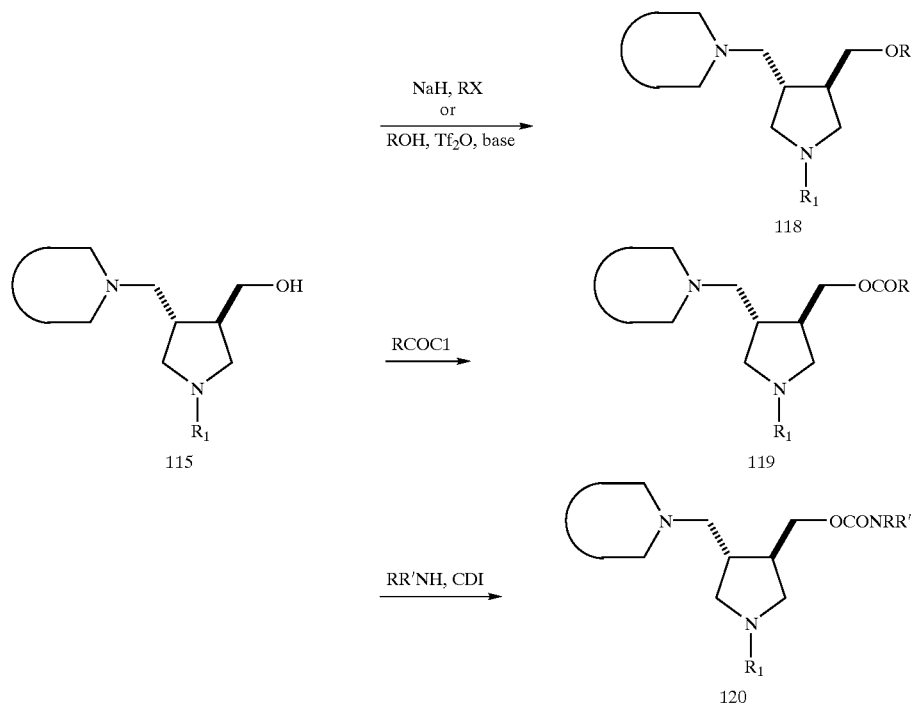

SCHEME 33

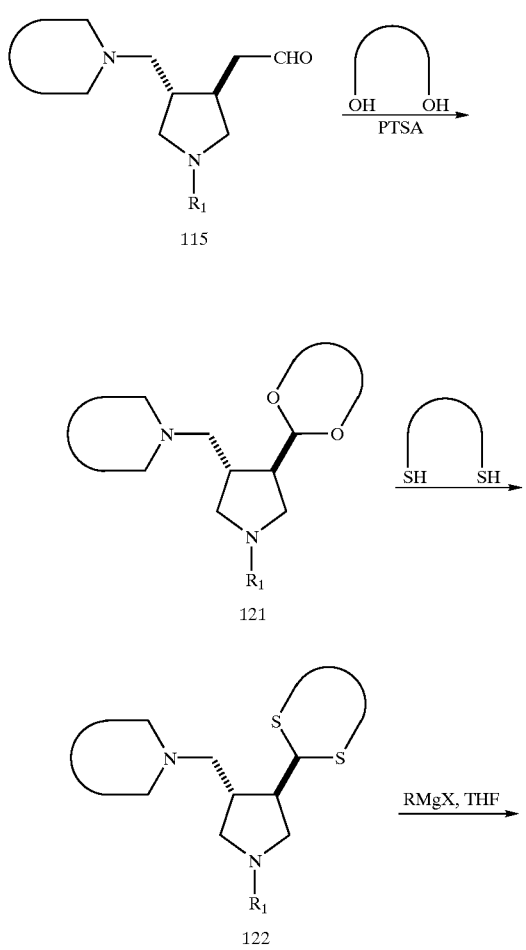

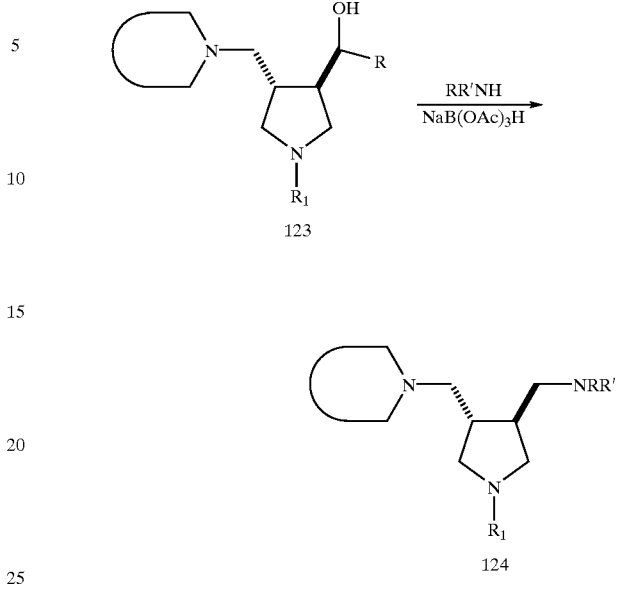

Aldehyde 115 can be converted to acetals as demonstrated in Scheme 33. Heating a solution of 115 with a diol such as ethylene glycol and an acid such as paratoluenesulfonic acid in a solvent such as benzene or toluene gives 1,3-dioxolane derivative 121. Other diols give corresponding acetals. Thioacetal derviatives (122) may be prepared by similar means. Aldehyde 115 may be reacted with nucleophiles such as Grignard reagents to give secondary alcohol derivatives 123. Aldehyde 115 can also be converted to amine 124 as described in Rxn Scheme 1.

SCHEME 34

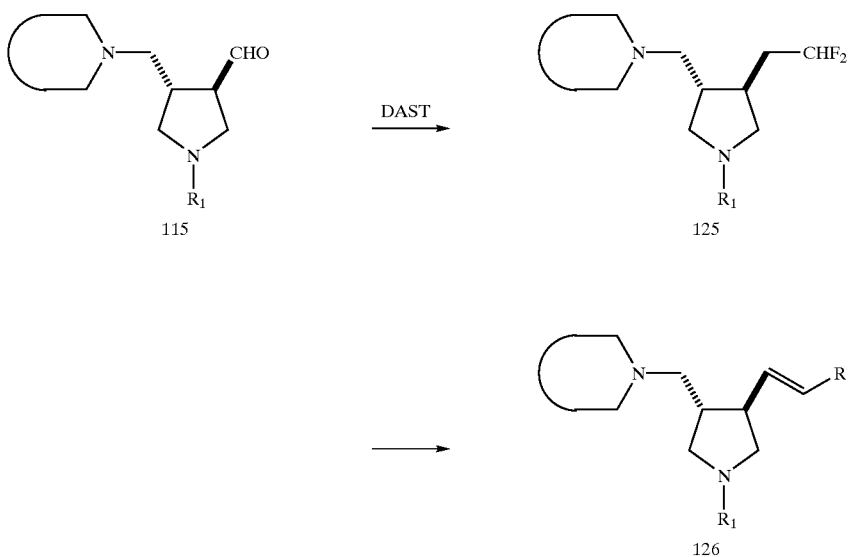

In Scheme 34, aldehyde 115 can be converted to the difluoro derivative 125 using $SF_4$ or the commercially available DAST ($Et_2NSF_3$) (see March J. "Advanced Organic Chemistry", 4th ed., John Wiley & Sons, New York, pp. 908–910 (1992)). Aldehyde 115 can be converted to olefin derivatives (126) by a variety of standard olefination conditions including Wittig, Horner-Emmons-Wadsworth and related reagents (see March J. "Advanced Organic Chemistry", 4th ed., John Wiley & Sons, New York, pp. 956–963 (1992)).

"Advanced Organic Chemistry", 4th ed., John Wiley & Sons, New York, pp. 432 (1992)). It may also be oxidized to ketone 128 with various chromium trioxide-based reagents (see March J. "Advanced Organic Chemistry", 4th ed., John Wiley & Sons, New York, pp. 1167–1171 (1992)). Ketone 128 can be converted to tertiary alcohol 129 by using nucleophiles such as Grignard reagents. Ketone 128 can also be converted to amine 130 as described in Reaction Scheme 1.

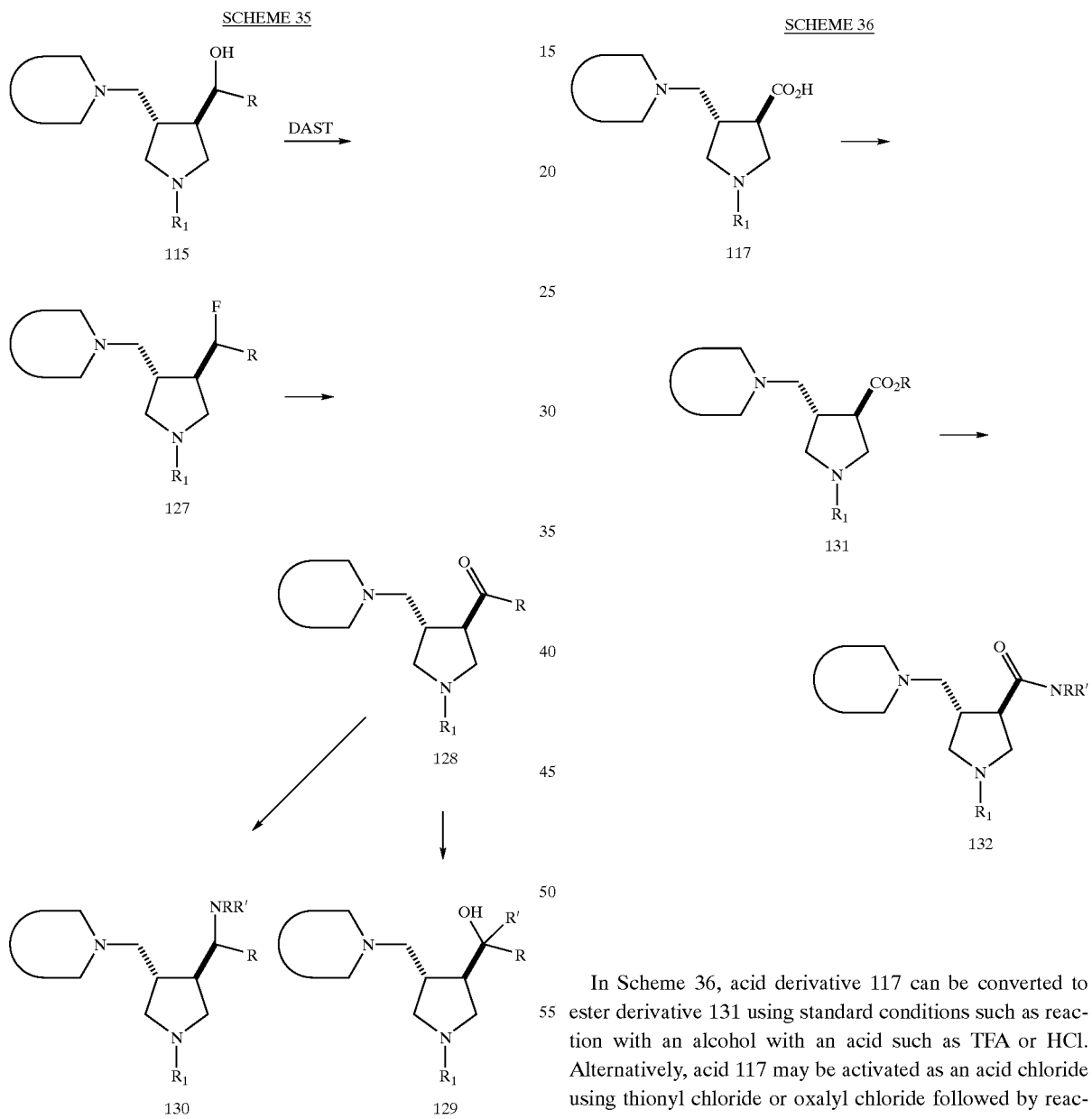

Secondary alcohol 115 can be converted to ether, ester and carbamate derivatives as described in Scheme 32. It may also be converted to the fluoro derivtive 127 using DAST as described in Reaction Scheme 34 and by March J.

In Scheme 36, acid derivative 117 can be converted to ester derivative 131 using standard conditions such as reaction with an alcohol with an acid such as TFA or HCl. Alternatively, acid 117 may be activated as an acid chloride using thionyl chloride or oxalyl chloride followed by reaction with an alcohol. Methyl esters can be prepared with diazomethane. Activation of acid 117 with a reagent such as BOP-Cl [bis(2-oxo-3-oxazolidinyl)phosphinic chloride] and a base such as Et3N in methylene chloride followed by addition of an alcohol or amine gives ester 131 or amide derivative 132. A variety of other standard amide coupling conditions may also be utilized.

SCHEME 37

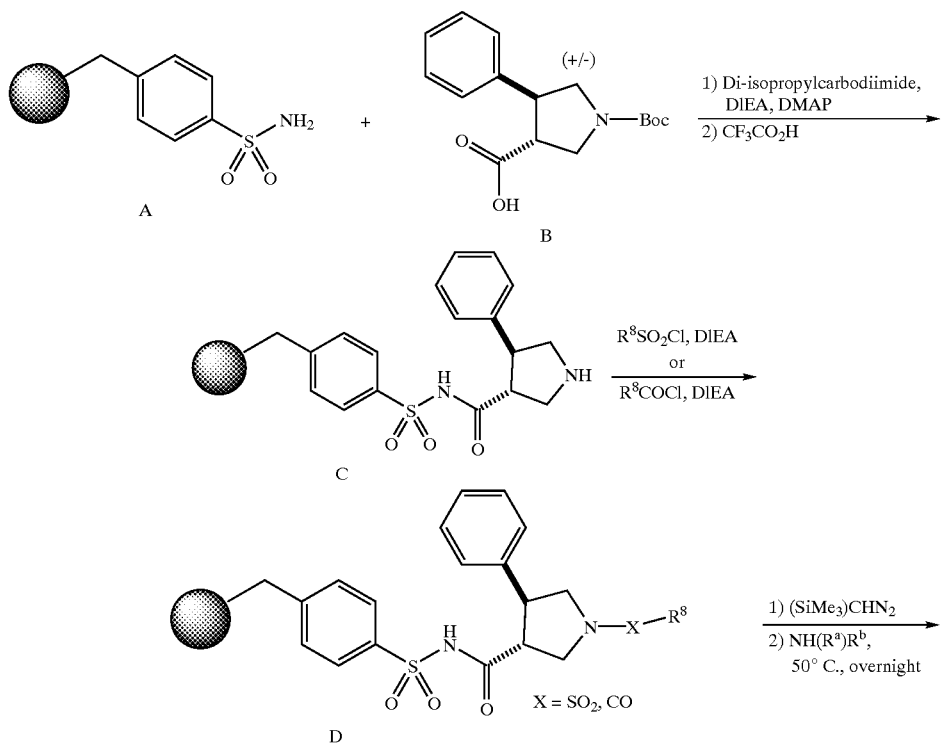

Preparation of target pyrrolidines using solid support technology is outlined in Scheme 22. Coupling of intermediate B to a commercially available 4-sulfamylbenzoyl polystyrene resin A (or a alkyl sulfamyl resin) is carried out with di-isopropylcarbodiimide or with other activating agents, for example dicyclohexylcarbodiimide, EDAC, oxalyl chloride, etc. Agents that result in the formation of the symmetrical anhydride from B (which then serves as the acylating agent) are also suitable for this purpose. Removal of the Boc group is carried out with trifluoroacetic acid or other acidic reagents, to give resin-bound pyrrolidine C. This intermediate is then coupled with sulfonyl chlorides or carbonyl chlorides in the presence of a suitable amine, preferably a hindered tertiary amine such as diisopropylethylamine (DIEA), lutidine, DBU, etc., to provide the N-functionalized pyrrolidine D. Alkylation of the acyl sulfonamide nitrogen can be carried out with trimethylsilyldiazomethane, diazomethane, with bromoacetonitrile in the presence of DBU and DMF, or under Mitsunobu conditions with a pheno such as pentafluorophenol. Reaction of the resulting N-alkylated intermediate with an amine $NH(R^a)R^b$ at a temperature between 0 and 140° C., preferably around 50° C., for 4–24 hr, preferably about 14 hr, then cleaves the pyrrolidine from the resin as amide E. Reduction of the newly formed amide (and other amide functionality, if present) with borane methyl sulfide complex (or other hydride reducing agents, such as borane-pyridine, borane-THF, lithium aluminum hydride, lithium di-(sec) butyl borohydride, etc) followed by hydrolysis with dilute hydrogen chloride in methanol at a temperature between 0° and 140° C., preferably around 50° C., for 4–24 hr, preferably about 14 hr, provides either sulfonamide F or amine G.

Cyclic amines (compound II) from Scheme 1 which are spirocyclic piperidines are prepared using azacyclic starting materials prepared using methods described in the literature; more specifically, as described in Claremon, D. A. et al, European Patent Publication 0 431 943, Evans, B. E. et al, U.S. Pat. No. 5,091,387, Davis, L. et al, U.S. Pat. No. 4,420,485, and Parham et al, *Journal of Organic Chemistry*, 41, 2628 (1976). None of the compounds in the foregoing references are alleged to be chemokine receptor modulators.

In some cases the order of carrying out the foregoing reaction schemes may be varied to facilitate the reaction or to avoid unwanted reaction products. The following examples are provided for the purposes of further illustration only and are not intended to be limitations on the disclosed invention.

EXAMPLE 1

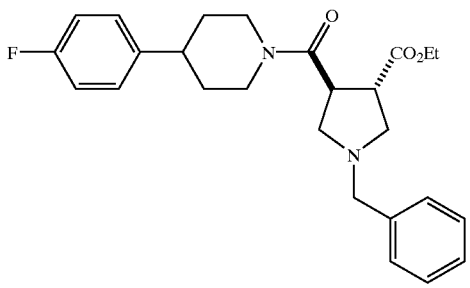

1-Benzyl-3-(RS)-(4-(4-fluorophenyl)piperidinylcarbonyl)-4-(RS)-(ethoxy carbonyl)pyrrolidine Step 1. 4-(4-Fluorophenyl)piperidine A mixture of 10 g (47 mmol) of 4-(4-fluorophenyl) tetrahydro pyridine hydrochloride (Aldrich-Saylor) and 1.18 g of 10% Pd/C in 100 mL of degassed MeOH ($N_2$) was stirred under hydrogen at 45 psi for 18 h. The reaction mixture was then filtered though a thin pad of celite eluting with MeOH. The filtrate was concentrated and the residue was stirred in 75 mL of ether. To it at 0° C. was added 5 g of solid NaOH. The layers were separated and the aqueous layer was extracted with ether. The combined organic fractions were washed with sat'd NaCl solution, dried over $Na_2SO_4$, filtered and the filtrate was concentrated. The residue was crystalized from cold heptane to give 10 g of the title compound.

Step 2. Ethyl-4-(4-(fluorophenyl)piperidinyl)fumarate

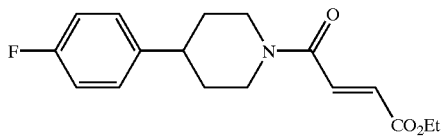

A solution of 2.87 g (20 mmol) of mono-ethylfumarate (Aldrich), 3.24 g (20 mmol of 4-(4-fluorophenyl)piperidine, 2.93 g (24 mmol) of 4-dimethylaminopyridinie, and 7.67 g (40 mmol) of 1-[3-(Dimethylamino)propyl]-3-ethylcarbodiimide hydrochloride in 40 mL of $CH_2Cl_2$ at rt was stirred for 2.5 h. The reaction mixture was diluted with $CH_2Cl_2$, washed with $NaHCO_3$, dried over $Na_2SO_4$, filtered. The filtrate was concentrated and the residue was purified by chromatography (silica, acetone: hexanes, 1:3) to give 4.4 g of the title compound $^1$H NMR ($CDCl_3$) δ 7.44 (d, 1H, J=15.5 Hz), 7.14–7.16 (m, 2H), 7.00 (t, 2H, J=8.5 Hz), 6.77 (d, 1H, J=15.5 Hz), 4.26 (q, 2H, J=7 Hz), 1.33 (t, 3H, J=7 Hz).

Step 2. 1-Benzyl-3-(RS)-(4-(4-fluorophenyl) piperidinylcarbonyl)-4-(RS)-(ethoxycarbonyl)pyrrolidine To a solution of 4.4 g (14.4 mmol) of ethyl-4-(4-(4-fluorophenyl) piperidinyl)fumarate, and 4.1 g (17.3 mmol) of N-(methoxymethyl)-N-trimethylsilyl methyl) benzylamine in 30 mL of $CH_2Cl_2$ at 0° C. was added 0.55 mL (7.2 mmol) of trifluoroacetic acid and the reaction mixture was stirred at 0° C. for 1 h. The reaction mixture was diluted with $CH_2Cl_2$ and washed with sat'd $NaHCO_3$. The combined organic fraction was dried over $Na_2SO_4$, filtered and the filtrate was concentrated. The residue was purified by chromatography (silica, acetone; hexanes, 1:3) to give 6.4 g of the title compound.

$^1$H NMR ($CDCl_3$) δ 7.32–7.33 (m, 4H), 7.24–7.28 (m, 1H), 7.12–7.16 (m, 2H), 7.00 (t, 2H, J=8.2 Hz), 4.81 (d, 1H, J=13 Hz), 4.11–4.19 (m, 3H), 3.59–3.77 (m, 4H), 3.03–3.18 (m, 3H), 2.86 (t, 1H, J=8.0 Hz), 2.50–2.77 (m, 4H), 1.88–1.90 (m, 2H), 1.44–1.65 (m, 2H), 1.26 (t, 3H, J=7.0 Hz), omplete NMR, Spectrum (ESI) m/e=439 (M+1).

EXAMPLE 2

1-Benzyl-3-(RS)-(4-(4-fluorophenyl)piperidinylmethyl)-4-(SR)-hydroxymethylpyrrolidine To a solution of 6.4 g (14.6 mmol) of 1-benzyl)-3-(RS)-(4-(4-fluorophenyl)piperidinylcarbonyl)-4-(RS)-(ethoxycarbonyl)pyrrolidine in 60 mL of THF at 0° C. was added 17.5 mL (17.5 mmol) of a 1M solution of lithium aluminum hydride (LAH) in ether and the reaction was stirred at 0° C. for 30 min. The reaction mixture was quenched with 5N NaOH. The reaction mixture was extracted with ether and the combined organic fractions were washed with 5N NaOH solution. The organic fractions were dried over $Na_2SO_4$, filtered and the filtrate was purified by chromatography [silica, hexanes: ethyl acetate: (2N $NH_3$ in MeOH), 10: 10: 1] to give 4.7 g of the title compound. Spectrum (ESI) m/e=383 (M+1).

$^1$H NMR ($CDCl_3$) δ c7.31–7.33 (m, 4H), 7.26–7.28 (m, 1H), 7.16–7.19 (m, 2H), 6.97 (t, 2H, J=8.5 Hz), 3.63–3.66 (m, 2H), 3.57 (d, 1H, J=13 Hz), 3.43 (t, 1H, J=10 Hz), 3.22 (d, 1H, J=11 Hz), 2.97 (d, 1H, J=11 Hz), 2.80 (d of d, 1H, J=8.5, 7.5 Hz), 2.76 (t, 1H, J=9 Hz), 2.12–2.54 (m, 8H), 2.02 (t of d, 1H, J=2.5, 12 Hz), 1.75–1.85 (m, 5H).

EXAMPLE 3

1-(1-Naphthoyl)-3-(RS)-(4-(4-fluorophenyl) piperidinylmethyl)-4-(SR)-hydroxyethylpyrrolidine Step 1. 3-(RS)-(4-(4-Fluorophenyl)piperidinylmethyl)-4-(SR)-hydroxyethylpyrrolidine A mixture of 0.89 g (2.3 mmol) of 1-benzyl-3-(RS)-(4-(4-fluorophenyl)piperidinylmethyl)-4-(SR)-hydroxyethylpyrrolidine, 2.9 g (17.7 mmol) of ammonium formate and 0.39 g of Pearlman's catalyst [Pd(OH)$_2$/C] in 30 mL of MeOH was stirred at 70° C. for 1 h. The reaction mixture was filtered through a thin pad of Celite and the filtrate was concentrated to give 0.7 g of the title compound.

Step 2. 1-(2-Naphthoyl)-3-(RS)-(4-(4-fluorophenyl) piperidinyl-methyl)-164-(SR)-hydroxyethylpyrrolidine To a solution of 0.63 g (2.15 mmol) of 3-(RS)-(4-(4-fluorophenyl) piperidinylmethyl)-4-(SR)-hydroxyethylpyrrolidine and 0.6 mL (4.3 mmol) of $Et_3N$ in 20 mL of $CH_2Cl_2$ at 0° C. was added 0.32 mL (2.15 mmol) of 2-naphthoyl chloride and the reaction mixture was stirred for 1.2 h. To the reaction mixture was added 0.5 mL of MeOH and the reaction mixture was stirred 18 h at rt. The reaction mixture was concentrated and the residue was purified by chromatography (silica, acetone: hexanes, 1:2 to 1:1) to give 0.63 g of the title compound.

$^1$H NMR ($CDCl_3$) δ 7.85–7.91 (m, 3H), 7.45–7.58 (m, 4H), 7.14–7.20 (m, 2H), 6.96–7.00 (m, 2H);

Mass Spectrum (ESI) m/e=447 (M+1).

EXAMPLE 4

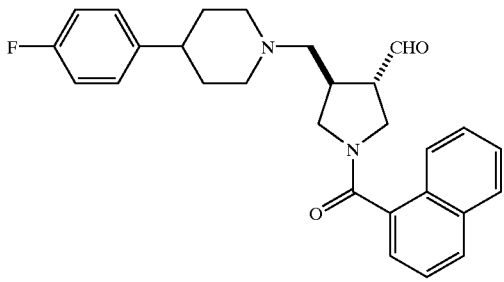

1-(1-Naphthoyl)-3-(RS)-(4-(4-fluorophenyl) piperidinylmethyl)-4-(SR)-formylpyrrolidine To a solution of 0.1 mL (1.2 mmol) of oxalyl chloride in 10 mL of $CH_2Cl_2$ at $-78°$ C. was added 0.17 mL (2.37 mmol) of DMSO and the reaction mixture was stirred for 10 min. To this reaction mixture at $-78°$ C. was added a solution of 0.26 g (0.59 mmol) of 1-(1-naphthoyl)-3-(RS)-(4-(4-fluorophenyl)piperidinylmethyl)-4-(SR)-hydroxymethylpyrrolidine in 10 mL of $CH_2Cl_2$. After stirring for 10 min. at 78° C., 0.41 mL (2.9 mmol) of $Et_3N$ was added and the reaction was allowed to warm to rt. The reaction mixture was poured into ether and washed twice with sat'd $NaHCO_3$ solution and once with sat'd NaCl solution. The organic fraction was dried over $Na_2SO_4$, filtered and the filtrate was concentrated to give 0.29 g of the title compound.

$^1$H NMR ($CDCl_3$) δ 9.85, 9.70 (d, 1H, J=2.0 Hz), 7.86–7.91 (m, 2H), 7.48–7.55 (m, 3H), 7.10–7.18 (m, 2H), 6.94–7.00 (m, 2H);

Mass Spectrum (ESI) m/e=445 M+1).

EXAMPLE 5

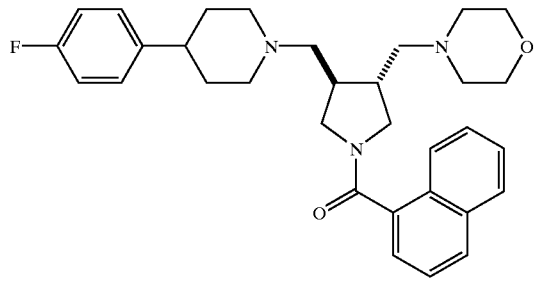

1-(1-Naphthoyl)-3-(RS)-(4-(4-fluorophenyl) piperidinylmethyl)-4-(RS)-(1-morpholinomethyl) pyrrolidine To a solution of 0.03 g (0.073 mmol) of 1-(1-naphthoyl)-3-(RS)-(4-(4-fluorophenyl)piperidinylmethyl)-4-(SR)-formylpyrrolidine and 0.013 mL (0.145 mmol) of morpholine in 2 mL of dichloroethane at rt was added 0.046 g (0.27 mmol) of sodium triacetoxyborohydride. After stirring for 1.5 h at rt, the reaction mixture was partitioned between $CH_2Cl_2$ and sat'd $NaHCO_3$. The organic fraction was dried over $Na_2SO_4$, filtered and the filtrate was concentrated. The residue was purified by chromatography (silica, $CH_2Cl_2$: MeOH, 95:5) to give the title compound.

$^1$H NMR ($CDCl_3$) δ (complete) 7.87–7.90 (m, 3H), 7.45–7.55 (m, 4H), 7.17–7.20, 7.08–7.11 (m, 2H), 7.00, 6.95 (t, 2H, J=9.0 Hz), 4.03–4.09 (m, 1H), 3.72 (t, 2H, <J=4.5 Hz), 3.60–3.64 (m, 1H), 3.56 (t, 2H, J=4.5 Hz), 2.97–3.06 (m, 2H), 2.82–2.88 (m, 1H), 2.43–2.55 (m, 4H), 2.24–2.43 (m, 5H), 2.09–2.19 (m, 3H), 1.49–1.98 (m, 5H;

Mass Spectrum (ESI) m/e=516 (M+1).

EXAMPLE 6

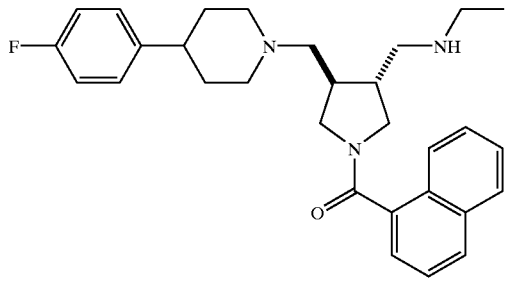

1-(1-Naphthoyl)-3-(RS)-(4-(4-fluorophenyl) piperidinylmethyl)-4-(RS)-(ethylaminomethyl)pyrrolidine The title compound was prepared as described in Example 5.

Mass Spectrum (ESI) m/e=474 (M+1).

EXAMPLE 7

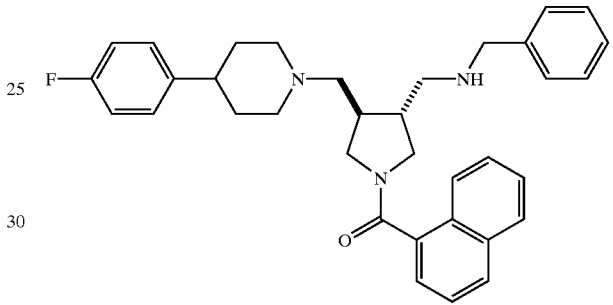

1-(1-Naphthoyl)-3-(RS)-(4-(4-fluorophenyl) piperidinylmethyl)-4-(RS)-(benzylaminomethyl)pyrrolidine The title compound was prepared as described in Example 5.

Mass Spectrum (ESI) m/e=536 (M+1).

EXAMPLE 8

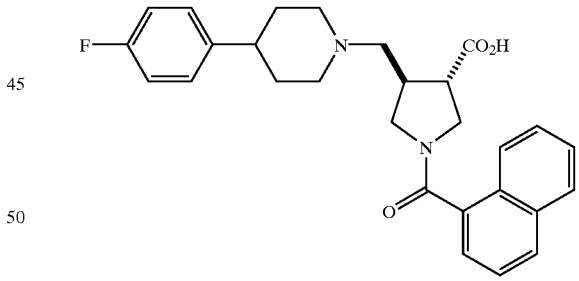

1-(1-Naphthoyl)-3-(RS)-(4-(4-fluorophenyl) piperidinylmethyl)-4-(SR)-carboxypyrrolidine A mixture of 0.126 g (0.28 mmol) of 1-(1-naphthoyl)-3-(RS)-(4-(4-fluorophenyl)piperidinylmethyl)-4-(SR)-hydroxymethyl pyrrolidine, 0.18 g (0.85 mmol) of $NaIO_4$, and 0.0029 g (0.014 mmol) of $RuCl_3 \cdot 3 H_2O$ in 2 mL of $CCl_4$, 3 mL of $H_2O$ and 2 mL of $CH_3CN$ was stirred at rt for 1 H. The reaction mixture was partitioned between $CH_2Cl_2$ and $H_2O$. The organic fraction was dried over $Na_2SO_4$, filtered and the filtrate was concentrated to give the title compound.

$^1$H NMR (key peaks) ($CDCl_3$) δ 7.81–7.88 (m, 3H), 7.43–7.74 (m, 4H), 7.11–7.14 (m, 2H), 6.97 (t, 2H, J=8.0 Hz), Mass Spectrum (ESI) m/e≦461 (M+1).

EXAMPLE 9

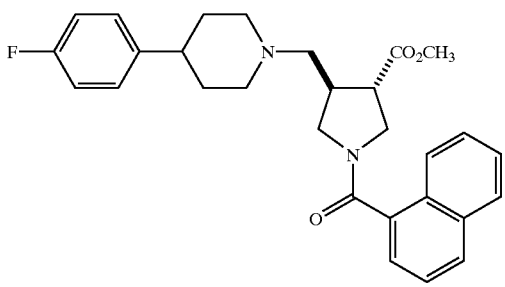

1-(1-Naphthoyl)-3-(RS)-(4-(4-fluorophenyl)piperidinylmethyl)-4-(SR)-methoxycarbonylpyrrolidine To a solution of 0.037 g (0.08 mmol) of 1-(1-naphthoyl)-3-(RS)-(4-(4-fluorophenyl)piperidinylmethyl)-4-(SR)-carboxypyrrolidine in 0.6 mL of MeOH and 1.2 mL of THF at rt was added 0.2 mL (0.4 mmol) of TMSCHN$_2$ (2M in hexanes) and the reaction mixture was stirred for 6 h. The reaction mixture was concentrated and the residue was purified by chromatography (silica, acetone: hexanes, 1:3) to give the title compound.

$^1$H NMR (CDCl$_3$) δ (key peaks) 7.87–7.91 (m, 3H), 7.47–7.56 (m, 4H), 7.15–7.18 and 7.08–7.11 (m, 2H), 6.98 and 6.95 (t, 2H, J=8.5 Hz), 3.79 and 3.62 (s, 3H);

Mass Spectrum (ESI) m/e=475 (M+1).

EXAMPLE 10

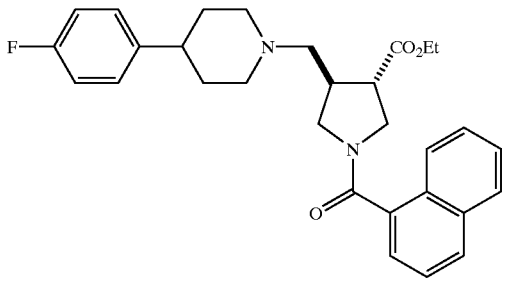

1-(1-Naphthoyl)-3-(RS)-(4-(4-fluorophenyl)piperidinylmethyl)-4-(SR)-ethoxycarbonylpyrrolidine To a solution of 0.026 g (0.057 mmol) of 1-(1-naphthoyl)-3-(RS)-4-(4-fluorophenyl)piperidinylmethyl)-4-(SR)-carboxypyrrolidine, 0.03 g (0.114 mmol) of BOP-Cl and 0.032 mL (0.228 mmol) of Et$_3$N in 2 mL of CH$_2$Cl$_2$ at rt was added 0.013 mL (0.228 mmol) of EtOH and the reaction mixture was stirred for 2 h. The reaction mixture was concentrated and the residue purified by chromatography (silica, acetone: hexanes, 1:2) then by HPLC (silica, Waters RCM 25×100 with (0.1% iPr2NH in methyl butyl ether): hexane=4.5:5.0 to give the title compound.

$^1$H NMR (CDCl$_3$) δ (key peaks) 7.88–7.91 (m, 3H), 7.47–7.57 (m, 4H), 7.16–7.19 and 7.09–7.12 (m, 2H), 6.99 and 6.96 (t, 2H, J=8.5 Hz), 1.34 and 1.21 (t, 3H, J=7.0 Hz);

Mass Spectrum (ESI) m/e=489 (M+1).

EXAMPLE 11

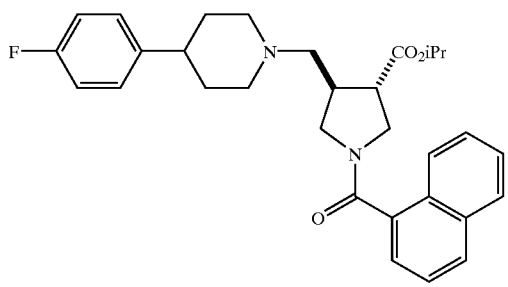

1-(1-Naphthoyl)-3-(RS)-(4-(4-fluorophenyl)piperidinylmethyl)-4-(SR)-isopropyloxycarbonylpyrrolidine The title compound was prepared as described in Example 10.

Mass Spectrum (ESI) m/e=503 (M+1).

EXAMPLE 12

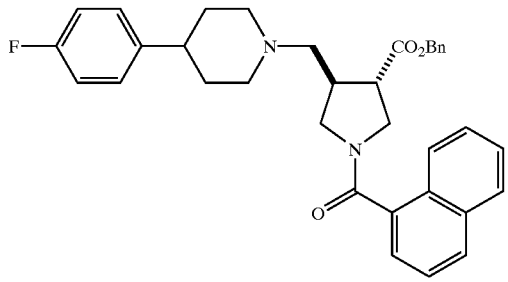

1-(1-Naphthoyl)-3-(RS)-(4-(4-fluorophenyl)piperidinylmethyl)-4-(SR)-benzyloxycarbonylpyrrolidine The title compound was prepared as described in Example 10.

$^1$H NMR (CDCl$_3$) δ (key peaks) 7.88–7.91 (m, 3H), 7.45–7.56 (m, 3H), 7.27–7.41 (m, 5H), 7.08–7.16 (m, 2H), 6.99 and 6.96 (t, 2H, J=9.0 Hz), 5.26 and 5.12 (d, 1H, J=12.5 Hz), 5.22 and 5.06 (d, 1H, J=12.5 Hz);

Mass Spectrum (ESI) m/e=551 (M+1).

EXAMPLE 13

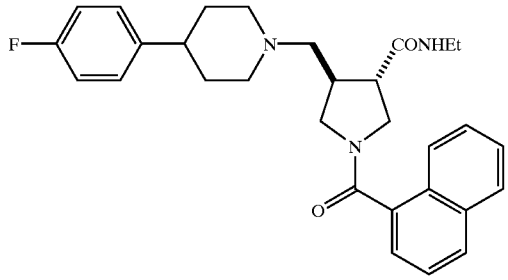

1-(1-Naphthoyl)-3-(RS)-(4-(4-fluorophenyl)piperidinylmethyl)-4-(SR)-N-ethylaminocarbonyl)pyrrolidine To a solution of 0.037 g (0.08 mmol) of 1-(1-naphthoyl)-3-(RS)-(4-(4-fluorophenyl)piperidinylmethyl)-4-(SR)-carboxypyrrolidone and 0.06 mL (0.12 mmol) of ethylamine in 2 mL of CH$_2$Cl$_2$ at rt was added 0.031 g (0.12 mmol) of BOPCl Bis(2-oxo-3-oxazolidinyl)phosphinic chloride, Aldrich) and 0.045 mL Et$_3$N and the reaction mixture was stirred for 18 h. The reAction mixture was concentrated and the residue was purified by chromatography (silica, acetone: hexanes, 1:2) to give the title compound.

¹H NMR (CDCl₃) δ (key peaks) 7.85–7.90 (m, 3H), 7.45–7.56 (m, 4H), 7.09–7.19 (m, 2H), 6.96–7.03 (m, 2H), 3.94–4.49 (m, 4H);

Mass Spectrum (ESI) m/e=488 (M+1).

EXAMPLE 14

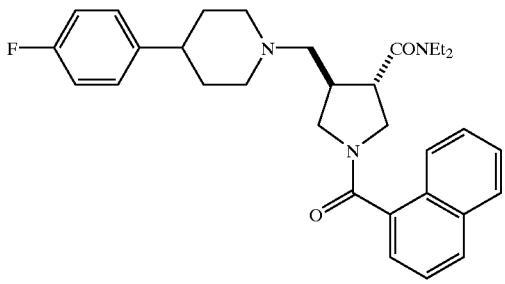

1-(1-Naphthoyl)-3-(RS)-(4-(4-fluorophenyl) piperidinylmethyl)-4-(SR)-(N,N-diethylaminocarbonyl) pyrrolidine The title compound was prepared as described in Example 13.

Mass Spectrum (ESI) m/e=516 (M+1).

EXAMPLE 15

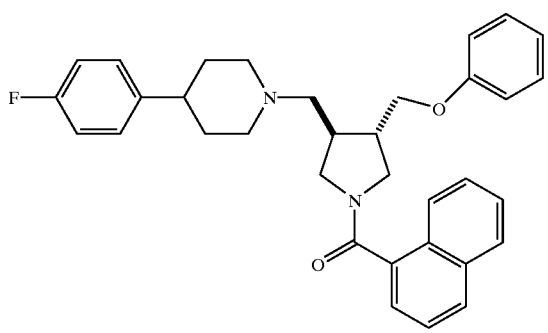

1-(1-Naphthoyl)-3-(RS)-(4-(4-fluorophenyl) piperidinylmethyl)-4-(SR)-(phenoxymethyl)pyrrolidine A solution of 0.062 g (0.14 mmol) of Ph₃Bi (Aldrich in 1 mL of CH₂Cl₂ and 0.65 mL of THF at rt was added 0.027 mL (0.18 mmol) of trifluoroacetic acid and the reaction mixture was stirred for 10 min. This solution was added to a solution of 0.046 g (0.1 mmol) of 1-(1-naphthoyl)-3-(RS)-(4-(4-fluorophenyl)piperidinylmethyl)-4-(SR)-hydroxyethylpyrrolidine in 1 mL of CH₂Cl₂. To this reaction mixture was added 0.0083 g (0.046 mmol) of Cu(OAc)₂ and the reaction mixture was stirred at 40° C. for 72 h. The reaction mixture was filtered through a thin pad of silica (acetone: hexanes, 1:2) and the filtrate was concentrated. The residue was purified by chromatography (silica, Waters RCM 25×100 with (0.1% iPr₂NH in methyl tbutyl ether): hexane=2.25:7.0) to give the title compound.

¹H NMR (CDCl₃) δ (key peaks) 7.88–7.92 (m, 3H), 7.47–7.56 (m, 4H), 7.23–7.34 (m, 2H), 7.07–7.18 (m, 2H), 6.92–7.01 (m, 4H), 6.80 (d, 1H, J=7.5 Hz), 5.12 (S, 2H).

Mass Spectrum (ESI) m/e=523 (M+1).

EXAMPLE 16

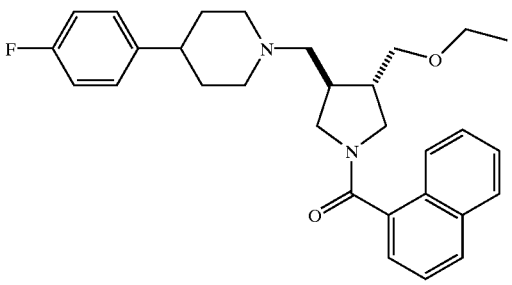

1-(1-Naphthoyl)-3-(RS)-(4-(4-fluorophenyl) piperidinylmethyl)-4-(S,R)-(ethoxymethyl)pyrrolidine To a solution of 0.033 g (0.074 mmol) of 1-(1-naphthoyl)-3-(RS)-(4-(4-fluorophenyl)piperidinylmethyl)-4-(SR)-hydroxymethylpyrrolidine and 0.057 g (0.22 mmol) of AgOTf in 2 mL of CH₂Cl₂ was added 0.058 mL (0.26 mmol) of 2,6-di-t-butylpyridine and 0.019 mL (0.24 mmol) of ethyl iodide and the reaction mixture was stirred at rt for 1.5 h. The reaction mixture was diluted with CH₂Cl₂ and filtered through a thin pad of Celite eluting with acetone; hexanes (1:2). The filtrate was concentrated and the residue was purified by chromatography (silica, acetone, hexanes, 1:3 to 1:2) to give the title compound.

¹H NMR (CDCl₃) δ (key peaks) 7.88–7.91 (M, 3H), 7.47–7.57 (M, 4H), 7.09–7.12 and 7.18–7.21 (M, 2H), 7.01 and 6.96 (t, 2H, J=8.5 Hz), 1.25 and 1.09 (t, 3H, J=7.0 Hz);

Mass Spectrum (ESI) m/e=475 (M+1).

EXAMPLE 17

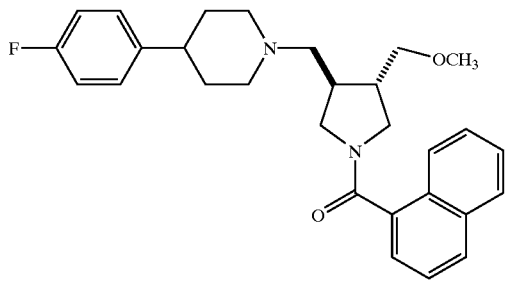

1-(1-Naphthoyl)-3-(RS)-(4-(4-fluorophenyl) piperidinylmethyl)-4-(SR)-(methoxymethyl)pyrrolidine A solution of 0.0025 g (0.057 mmol) of 1-(1-naphthoyl)-3-(RS)-(4-(4-fluorophenyl)piperidinylmethyl)-4-(SR)-hydroxymethylpyrrolidine, 0.013 g (0.23 mmol) of KOH and 0.028 mL (0.46 mmol) of methyl iodide in 2 mL of DMSO was stirred at rt for 1.2 h. The reaction mixture was poured into ether and washed with sat'd NaHCO₃ and NaCl solutions, dried over Na₂O₄ and filtered. The filtrate was concentrated and the residue was purified by chromatography (silica, acetone: hexanes, 1:2) to give the compound.

Mass Spectrum (ESI) m/e=461 (M+1).

EXAMPLE 18

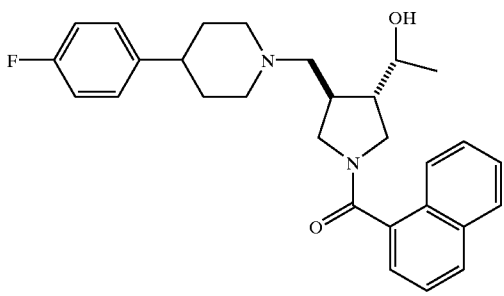

1-(1-Naphthoyl)-3-(RS)-(4-(4-fluorophenyl)piperidinylmethyl)-4-(SR)-(1-hydroxyethyl)pyrrolidine (diasteromers 1 and 2)

To a solution of 0.03 g (0.67 mmol) of 1-(1-naphthoyl)-3-(RS)-4-(4-fluorophenyl)piperidinylmethyl)-4-(SR)-formylpyrrolidine in 6 mL of THF at 0° C. was added 1.34 mL (1.34 mmol) of MeMgBr (1M in THF). The reaction mixture was warmed to rt and stirred for 3 h. The reaction mixture was quenched with sat'd NaHCO$_3$ solution. The organic fraction was filtered through a thin pad of Celite. The filtrate was concentrated and purified by chromatography (silica, hexanes:ethyl acetate:EtOH, 10:10:1) to give 0.05 g of diastereomer #1 and 0.16 g of diastereomer #2.

Diastereomer #1

$^1$H NMR (CDCl$_3$) δ (key peaks) 7.86–7.91 (m, 3H), 7.46–7.58 (m, 4H), 7.13–7.19 (m, 2H), 6.94–7.00 (m, 2H), 1.30 and 0.90 (d, 3H, J=6.0 Hz);

Mass Spectrum (ESI) m/e=461 (M+1).

Diastereomer #2

$^1$H NMR (CDCl$_3$) δ (key peaks) 7.84–7.90 (m, 3H), 7.44–7.56 (m, 4H), 7.12–7.18 (m, 2H), 6.94–6.98 (m, 2H), 1.24 and 1.03 (d, 3H, J=6.5 Hz)

Mass Spectrum (ESI) m/e=461 (M+1).

The following Examples 19 to 24 were prepared from 1-(1-naphthoyl)-3-(RS)-(4-(4-fluorophenyl)piperidinylmethyl)-4-(SR)-formylpyrrolidine and the corresponding Grignard reagent as described in Example 19

EXAMPLE 19

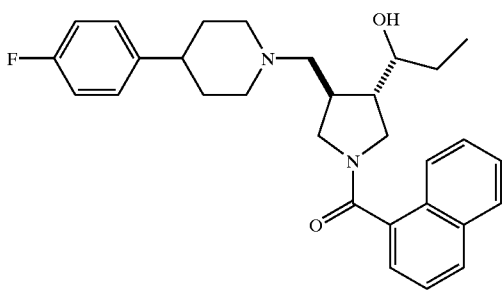

1-(1-Naphthoyl)-3-(RS)-(4-(4-fluorophenyl)piperidinylmethyl)-4-(SR)-(1-hydroxypropyl)pyrrolidine Diastereomer #1

Mass Spectrum (ESI) m/e=475 (M+1).

Diastereomer #2

Mass Spectrum (ESI) m/e=475 (M+1).

EXAMPLE 20

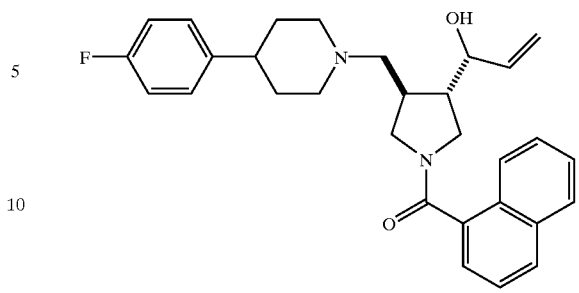

1-(1-Naphthoyl)-3-(RS)-(4-(4-fluorophenyl)piperidinylmethyl)-4-(SR)-(1-hydroxy-2-propenyl)pyrrolidine Diastereomer #1

Mass Spectrum (ESI) m/e=473 (M+1).

Diastereomer #2

Mass Spectrum (ESI) m/e=473 (M+1).

EXAMPLE 21

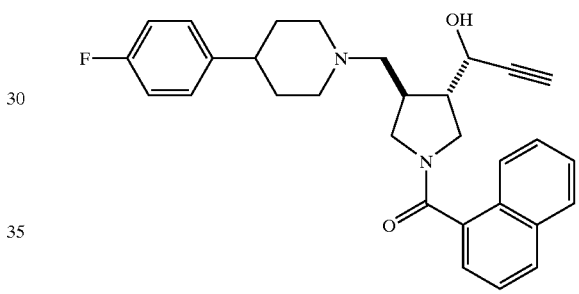

1-(1-Naphthoyl)-3-(RS)-(4-(4-fluorophenyl)piperidinylmethyl)-4-(SR)-(1-hydroxy-2-propynyl)pyrrolidine Mass Spectrum (ESI) m/e=471 (M+1).

EXAMPLE 22

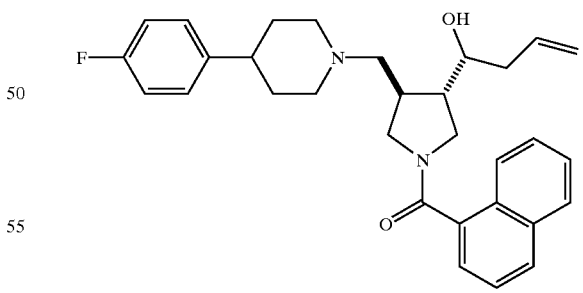

1-(1-Naphthoyl)-3-(RS)-(4-(4-fluorophenyl)piperidinylmethyl)-4-(SR)-(1-hydroxy-3-butenyl)pyrrolidine Diastereomer #1

Mass Spectrum (ESI) m/e=487 (M+1).

Diastereomer #2

Mass Spectrum (ESI) m/e=487 (M+1).

EXAMPLE 23

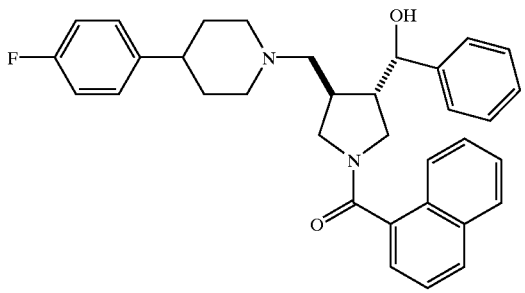

1-(1-Naphthoyl)-3-(RS)-(4-(4-fluorophenyl)
piperidinylmethyl)-4-(SR)-(phenylhydroxymethyl)
pyrrolidine
Diastereomer #1
  Mass Spectrum (ESI) m/e=523 (M+1).
Diastereomer #2
  Mass Spectrum (ESI) m/e=523 (M+1).

EXAMPLE 24

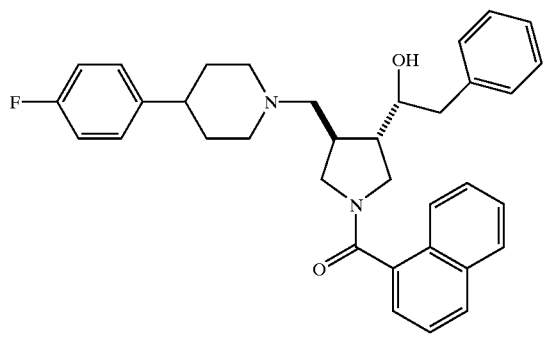

1-(1-Naphthoyl)-3-(RS)-(4-(4-fluorophenyl)
piperidinylmethyl)-4-(SR)-(2-phenyl-1-hydroxyethyl)
pyrrolidine
  Mass Spectrum (ESI) m/e=537 (M+1).

EXAMPLE 25

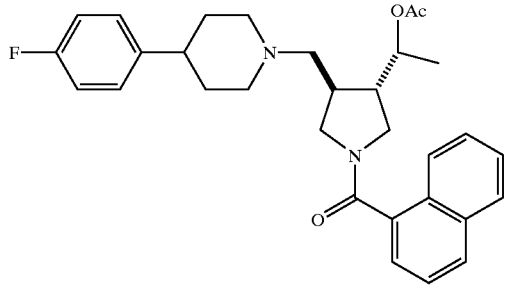

1-(1-Naphthoyl)-3-(RS)-(4-(4-fluorophenyl)
piperidinylmethyl)-4-(SR)-(1-acetoxyethyl)pyrrolidine A solution of 0.026 g (0.057 mmol) of 1-(1-naphthoyl)-
3-(RS)-(4-(4-fluorophenyl)piperidinylmethyl)-4-(SR)-(1-
hydroxyethyl)pyrrolidine (diastereomer 2, Example 18),
0.027 mL (0.28 mmol) of acetic anhydride, 0.046 mL of
pyridine and 3.4 mg of DMAP in 2 mL of THF was stirred
at rt for 18 h. The reaction mixture was concentrated and
purified by chromatography (silica, hexanes:ethylacetate:
(2N $NH_3$ in MeOH), 15:15:1) to give the title compound as
white solid.

$^1$H NMR (CDCl$_3$) δ (key peaks) 7.89–7.90 (m, 3H),
7.47–7.54 (m, 4H), 7.19 and 7.09 (d of d, 2H, J=6.0, 8.5 Hz),
6.99 and 6.94 (t, 2H, J=8.5 Hz), 5.04–5.20 (m, 1H), 1.34 and
1.09 (d, 3H, J=6.5 Hz),
  Mass Spectrum (ESI) m/e=503 (M+1).

EXAMPLE 26

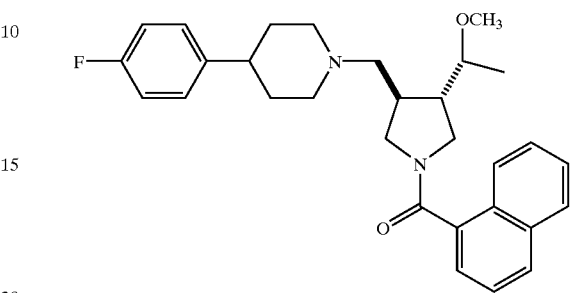

1-(1-Naphthoyl)-3-(RS)-(4-(4-fluorophenyl)
piperidinylmethyl)-4-(SR)-(1-methoxyethyl)pyrrolidine A solution of 0.026 g (0.057 mmol) of 1-naphthoyl)-3-
(RS)-(4-(4-fluorophenyl)piperidinylmethyl)-4-(SR)-(1-
hydroxyethyl)pyrrolidine (diastereomer 2), 0.012 mg (0.23
mmol) of KOH and 0.0042 mL (0.068 mmol) of methylio-
dide in 1 mL of DMSO was stirred at rt for 30 min. The
reaction mixture was diluted with ether and washed with
sat'd NaHCO$_3$ and NaCl solutions. The organic fraction was
dried over Na$_2$SO$_4$, filtered and the filtrate was concentrated
and purified by chromatography (silica,
hexanes:ethylacetate:(2N NH$_3$ in MeOH), 10:10:1) to give
the title compound.

$^1$H NMR (CDCl$_3$) δ (key peaks) 7.88–7.91 (m, 3H),
7.45–7.55 (m, 4H), 7.20 and 7.10 (d of d, 2H, J=5.5, 8.5 Hz),
7.00 and 6.95 (t, 2H, J=9.0 Hz), 3.40 and 3.24 (s, 3H) 1.25
and 1.02 (d, 3H, J=6.5 Hz),
  Mass Spectrum (ESI) m/e=475 (M+1).

EXAMPLE 27

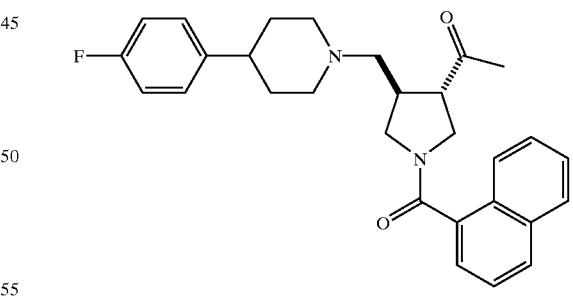

1-(1-Naphthoyl)-3-(RS)-(4-(4-fluorophenyl)
piperidinylmethyl)-4-(SR)-acetylpyrrolidine The title compound was prepared from 1-(1-naphthoyl)-
3-(RS)-(4-(4-fluorophenyl)piperidinylmethyl)-4-(SR)-(1-
hydroxyethyl)pyrrolidine according to procedures described
in Example 4.

$^1$H NMR (CDCl$_3$) δ (key peaks) 7.86–7.91 (m, 3H),
7.44–7.57 (m, 4H), 7.08–7.16 (m, 2H), 6.93–6.99 (m, 2H),
2.34 and 2.17 (s, 3H);
  Mass Spectrum (ESI) m/e=459 (M+1).

EXAMPLE 28

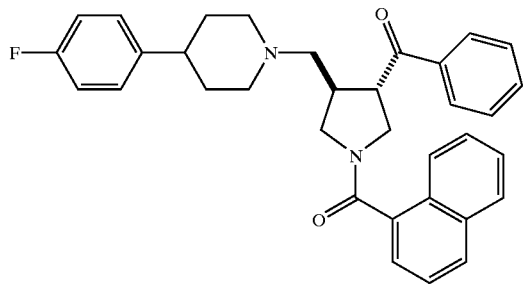

1-(1-Naphthoyl)-3-(RS)-(4-(4-fluorophenyl)piperidinylmethyl)-4-(SR)-benzoylpyrrolidine The title compound was prepared from 1-(1-naphthoyl)-3-(RS)-(4-(4-fluorophenyl)piperidinylmethyl)-4-(SR)-(phenylhydroxymethyl) pyrrolidine according to procedures described in Example 4.

$^1$H NMR (CDCl$_3$) δ (key peaks) 8.14 (d, 1H, J=7.5 Hz), 7.97–8.01 (m, 2H), 7.42–7.63 (7H), 6.93–7.01 (m, 4H), Mass Spectrum (ESI) m/e=521 (M+1).

EXAMPLE 29

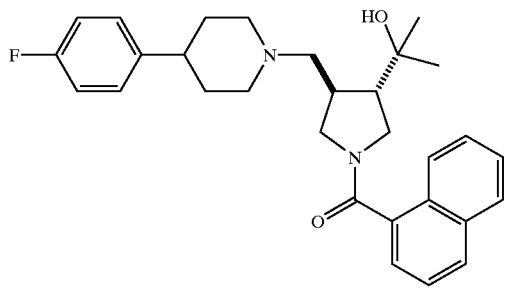

1-(1-Naphthoyl)-3-(RS)-(4-(4-fluorophenyl)piperidinylmethyl)-4-(SR)-(1-hydroxy-1-methylethyl)pyrrolidine To a solution of 0.03 g (0.065 mmol) of 1-(1-naphthoyl)-3-(RS)-(4-(4-fluorophenyl)piperidinylmethyl)-4-(SR)-acetylpyrrolidine in 20 mL of THF at rt was added 0.19 mL (0.195 mmol) of MeMgBr (1M in THF) and the reaction mixture was stirred for 30 min. The reaction mixture was partitioned between CH$_2$Cl$_2$ and NaHCO$_3$. The organic fraction was filtered through a thin pad of Celite and the filtrate was concentrated. The residue was purified by chromatography (silica, MeOH:CH$_2$Cl$_2$, 2:98) to give the title compound.

$^1$H NMR (CDCl$_3$) δ (key peaks) 7.88–7.89 (m, 3H), 7.45–7.57 (m, 4H), 7.13–7.19 (m, 2H), 6.94–6.99 (m, 2H), 1.31 and 1.08 (s, 3H), 1.25 and 0.91 (s, 3H);

Mass Spectrum (ESI) m/e=475 (M+1).

EXAMPLE 30

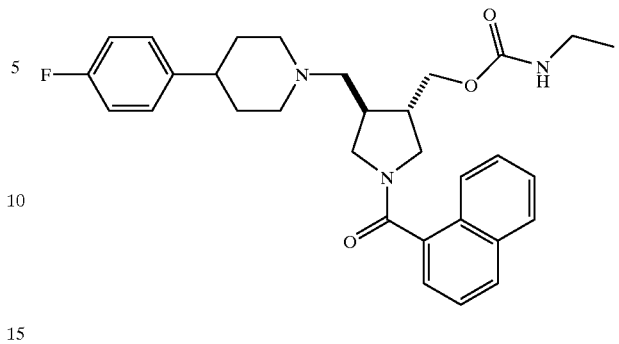

1-(1-Naphthoyl)-3-(RS)-(4-(4-fluorophenyl)piperidinylmethyl)-4-(SR)-(N-ethylcarbamoyloxymethyl)pyrrolidine Step 1. 1-(1-Naphthoyl)-3-(RS)-(4-(4-fluorophenyl)piperidinyl-methyl)-4-(SR)-(4-nitrophenoxycarbonyloxymethyl)-pyrrolidine

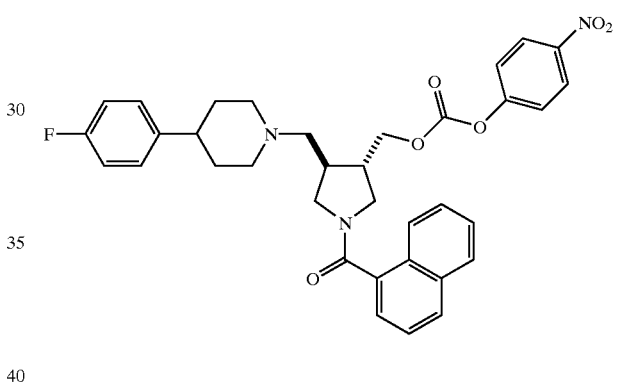

A solution of 0.1 g (0.225 mmol) of 1-(1-naphthoyl)-3-(RS)-(4-(4-fluorophenyl)piperidinylmethyl)-4-(SR)-4-(nitrophenoxycarbonyl oxymethyl)pyrrolidine, 0.055 g (0.45 mmol) of DMAP, 0.094 mL (0.68 mmol) of Et$_3$N and 0.082 g (0.41 mmol) of 4-nitrophenylchloroformate in 4 mL of CH$_2$Cl$_2$ was stirred at rt for 16 h. The reaction mixture was concentrated and the title compound was used without further purification.

Step 2. A solution of 0.045 g (0.075 mmol) of 1-(1-Naphthoyl)-3-(RS)-(4-(4-fluorophenyl)piperidinylmethyl)-4-(SR)-(N-ethylcarbamoyl oxymethyl)pyrrolidine and 0.23 mL (0.45 mmol) of ethylamine in 2 mL of CH$_2$Cl$_2$ was stirred at rt for 2 h. The reaction mixture was diluted with ether and washed twice with 2N NaOH solution. The organic fraction was dried over Na$_2$SO$_4$, filtered and the filtrate was concentrated. The residue was purified by chromatography (silica, acetone:hexanes, 1:3) to give the title compound.

$^1$H NMR (CDCl$_3$) δ (key peaks) 7.85–7.91 (m, 3H), 7.45–7.56 (m, 4H), 7.08–7.20 (m, 2H), 6.93–7.01 (m, 2H), 1.17 (t, 3H, J=7.0 hz);

Mass Spectrum (ESI) m/e=518 (M+1).

EXAMPLE 31

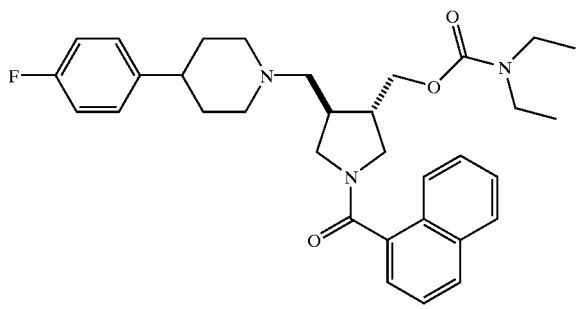

1-(1-Naphthoyl)-3-(RS)-(4-(4-fluorophenyl)piperidinylmethyl)-4-(SR)-(N,N-diethylcarbamoyloxymethyl)pyrrolidine The title compound was prepared as described in Example 30, using diethylamine.

Mass Spectrum (ESI) m/e=546 (M+1).

EXAMPLE 32

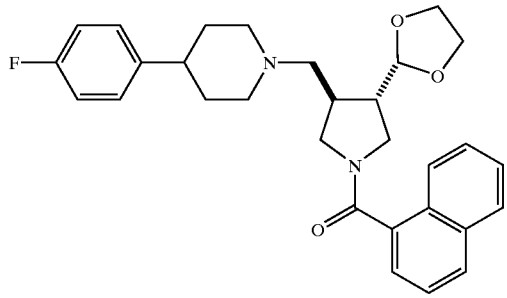

1-(1-Naphthoyl)-3-(RS)-(4-(4-fluorophenyl)piperidinylmethyl)-4-(SR)-(1,3-dioxolan-2-yl)pyrrolidine Step 1. 1-Benzyl-3-(RS)-(4-(4-fluorophenyl)piperidinylmethyl)-4-(SR)-formylpyrrolidine

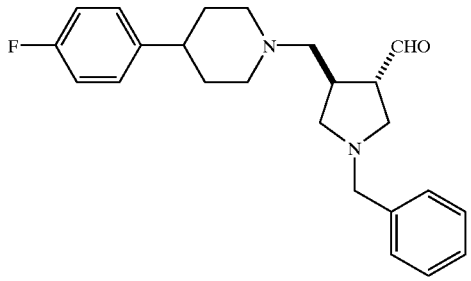

The title compound was prepared from 1-benzyl-3-(RS)-(4-(4-fluorophenyl)piperidinylmethyl)-4-(SR)-hydroxymethylpyrrolidine according to procedures described in Example 4.

Step 2. 1-(Benzyl)-3-(RS)-(4-(4-fluorophenyl)piperidinylcarbonyl)-4-(SR)-(1,3-dioxolan-2-yl)pyrrolidine A solution of 0.046 g (0.104 mmol) of 1-benzyl-3-(RS)-(4-(4-fluorophenyl)piperidinylmethyl)-4-(SR)-formylpyrrolidine, 0.058 mL (1.04 mmol) of ethyleneglycol and 0.047 g (0.25 mmol) of TsOH.H$_2$O in 5 mL of benzene was heated at reflux for 2 h. The reaction mixture was cooled to rt and diluted with ether. The reaction mixture was washed twice with sat'd NaHCO$_3$ solution, dried over Na$_2$SO$_4$, filtered and the filtrate was concentrated. The residue was purified by chromatography (silica, MeOH:CH$_2$Cl$_2$, 5:95) to give the title compound.

Step 3. 3-(RS)-(4-(4-Fluorophenyl)piperidinylmethyl)-4-(SR)-((1,3-dioxolan-2-yl)pyrrolidine The title compound was prepared as described in Example 3, Step 1.

Step 4. 1-(2-Naphthoyl)-3-(RS)-(4-(4-fluorophenyl)piperidinylmethyl)-4-(SR)-(1,3-dioxolan-2-yl)pyrrolidine The title compound was prepared from 3-(RS)-(4-(4-fluorophenyl)piperidinylmethyl)-4-(S,R)-(1,3-dioxolan-2-yl)pyrrolidine and 2-naphthoylchloride as described in Example 3, Step 2.

$^1$H NMR (CDCl$_3$) δ (key peaks) 7.87–7.93 (m, 3H), 7.46–7.55 (m, 4H), 7.19 and 7.09 (d of d, 2H, J=5.5, 8.5 Hz), 7.00 and 6.95 (t, 2H, J=8.5 Hz), 5.03 and 4.85 (d, 1H, J=3.5 Hz);

Mass Spectrum (ESI) m/e=489 (M+1).

The following Examples 34 to 36 were prepared from 1-(1-naphthoyl)-3-(RS)-(4-(4-fluorophenyl)piperidinylmethyl)-4-(SR)-formylpyrrolidine and the corresponding diol according to procedures described in Example 33.

EXAMPLE 34

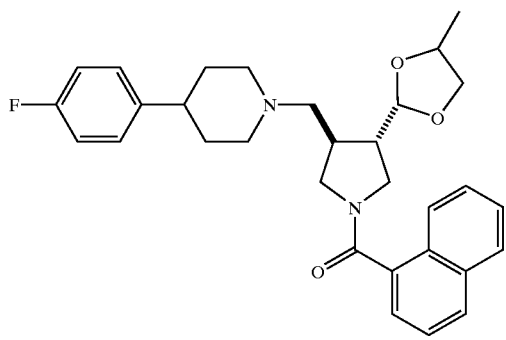

1-(2-Naphthoyl)-3-(RS)-(4-(4-fluorophenyl)
piperidinylmethyl)-4-(SR)-(4-methyl-1,3-dioxolan-2-yl)
pyrrolidine Mass Spectrum (ESI) m/e=504 (M+1).

EXAMPLE 35

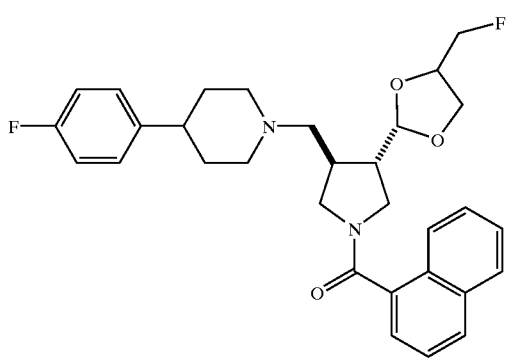

1-(2-Naphthoyl)-3-(RS)-(4-(4-fluorophenyl)
piperidinylmethyl)-4-(SR)-(4-fluoromethyl-1,3-dioxolan-2-yl)pyrrolidine Mass Spectrum (ESI) m/e=522 (M+1).

EXAMPLE 35

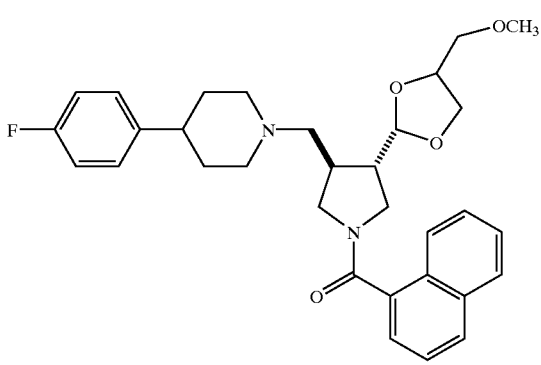

1-(2-Naphthoyl)-3-(RS)-(4-(4-fluorophenyl)
piperidinylmethyl)-4-(SR)-(4-methoxymethyl-1,3-dioxolan-2-yl)pyrrolidine Mass Spectrum (ESI) m/e=534 (M+1).

EXAMPLE 36

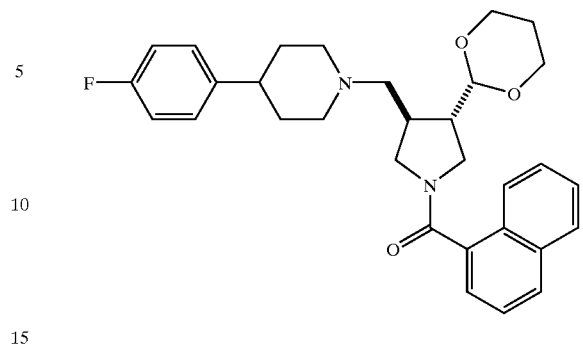

1-(1-Naphthoyl)-3-(RS)-(4-(4-fluorophenyl)
piperidinylmethyl)-4-(SR)-(1,3-dioxan-2-yl)pyrrolidine Mass Spectrum (ESI) m/e=503 (M+1).

EXAMPLE 37

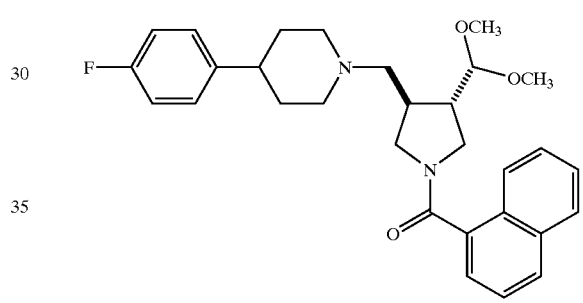

1-(1-Naphthoyl-3-(RS)-(4-(4-fluorophenyl)
piperidinylmethyl)-4-(S,R)-(1,1-dimethoxymethyl)
pyrrolidine A solution of 0.035 g (0.078 mmol) of 1-(2-naphthoyl)-3-(RS)-(4-(4-fluorophenyl)piperidinylcarbonyl)-4-(SR)-formylpyrrolidine, 0.085 mL (0.78 mmol) of trimethylorthoformate and 0.018 g (0.094 mmol) of TsOH.H$_2$O in 2 mL of MeOH was heated at reflux for 2 h. The reaction mixture was diluted with ether and washed twice with sat'd NaHCO$_3$ solution and NaCl solution. The organic fraction was dried over Na$_2$SO$_4$, filtered and the filtrate was concentrated. The residue was purified by chromatography [silica, ethyl acetate:hexanes:(2N NH$_3$ in MeOH), 10:10:1] to give the title compound.

$^1$H NMR (CDCl$_3$) δ (key peaks) 7.87–7.91 (m, 3H), 7.45–7.55 (m, 4H), 7.19 and 7.09 (d of d, 2H, J=5.5, 9.0 Hz), 7.00 and 6.95 (t, 2H, J=8.5 Hz), 4.38 and 4.27 (d, 1H, J=6.0 Hz);

Mass Spectrum (ESI) m/e=491 (M+1).

EXAMPLE 38

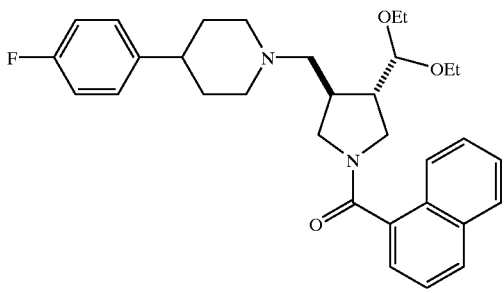

1-(1-Naphthoyl)-3-(RS)-(4-(4-fluorophenyl)piperidinylcarbonyl)-4-(SR)-(1,1-diethoxymethyl)pyrrolidine The title compound was prepared as described in Example 39 using triethylorthoformate.

Mass Spectrum (ESI) m/e=519 (M+1).

EXAMPLE 40

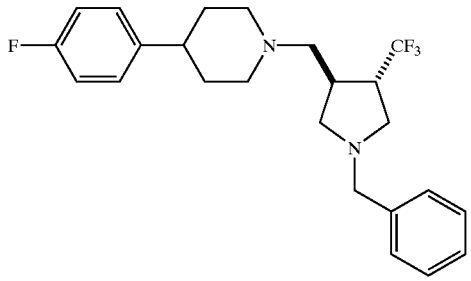

1-Benzyl-3-(RS)-(4-(4-fluorophenyl)piperidinylmethyl)-4-(SR)-(trifluoromethyl)pyrrolidine Step 1. 1-Benzyl-3-(RS)-carboethoxy-4-(RS)-trifluoromethylpyrrolidine

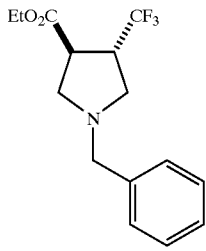

The title compound (1.8 g) was prepared from ethyl-3-trifluoromethyl acrylate, and N-(methoxymethyl)-N-trimethylsilyl methyl)benzylamine as described in Example 1, Step 2.

$^1$H NMR (CDCl$_3$) δ (complete) 7.27–7.42 (m, 5H), 4.20 (q, 2H, J=7.0 Hz), 3.67 (d, 1H, J=13 Hz), 3.61 (d, 1H, J=13 Hz), 3.37–3.43 (m, 1H), 3.12–3.15 (m, 1H), 2.81–2.93 (m, 3H), 2.71 (d of d, 1H, J=6, 10 Hz).

Step 2: 1-Benzyl-3-(RS)-hydroxymethyl-4-(RS)-trifluoromethyl pyrrolidine

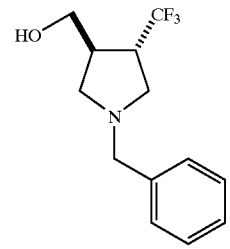

To a solution of 1.8 g (6 mmol) of 1-benzyl-3-(RS)-carboethoxy-4-(RS)-trifluoromethylpyrrolidine in 20 mL of THF at 0° C. was added 4.8 mL (4.8 mmol) of a 1M solution of LAH in THF and the reaction was stirred at rt for 30 min. The reaction mixture was quenched with 5N NaOH solution and extracted with ether. The combined organic fractions were washed with 2N NaOH solution and sat'd NaCl solution, dried over Na$_2$SO$_4$, filtered and the filtrate was concentrated. The residue was purified by chromatography (silica, acetone:hexanes, 1:8) to give 1.5 g of the title compound.

$^1$H NMR (CDCl$_3$) δ (key peaks) 7.28–7.37 (m, 5H), 3.76 (d of d, 1H, J=3.5, 10.5 Hz), 3.63 (s, 2H), 3.62 (d of d, 1H, J=5.0, 10.5 Hz), 3.11 (t, 1H, J=9.0 Hz), 2.60 (t, 1H, J=7.0 Hz), 2.45–2.49 (m, 1H), 2.42 (d of d, 1H, J=7.5, 9.5 Hz).

Step 3: 1-Benzyl-3-(RS)-formyl-4-(RS)-trifluoromethylpyrrolidine

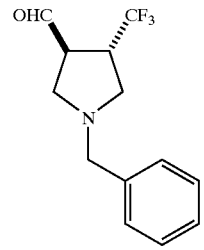

To a solution of 0.98 mL (11.2 mmol) of oxalyl chloride in 30 mL of CH$_2$Cl$_2$ at –78° C. was added 1.6 mL (22.4 mmol) of DMSO and the reaction mixture was stirred for 10 min. To this reaction mixture at –78° C. was added a solution of 1.46 g (5.6 mmol) of 1-benzyl-3-(RS)-hydroxymethyl-4-(RS)-trifluoromethylpyrrolidine in 10 mL of CH$_2$Cl$_2$. After stirring for 10 min. at –78° C., 3.9 mL (28 mmol) of Et$_3$N was added and the reaction was allowed to warm to rt. The reaction mixture was poured into ether and extracted twice with sat'd NaHCO$_3$ solution and once with sat'd NaCl solution. The organic fraction was dried over Na$_2$SO$_4$, filtered and the filtrate was concentrated to give 1.46 g of the title compound.

Step 4: 1-Benzyl-3-(RS)-(4-(4-fluorophenyl)piperidinylmethyl)-4-(SR)-(trifluoromethyl)pyrrolidine To a solution of 1.46 g (5.6 mmol) of 1-benzyl-3-(RS)-formyl-4-(RS)-trifluoromethylpyrrolidine and 0.13 g (0.67 mmol) of 4-(4-fluorophenyl)piperidine (Example 1, Step 1) in 30 mL of dichloroethane at rt was added 2.37 g (11.2 mmol) of sodium triacetoxyborohydride. After stirring for 18 h at rt, the reaction mixture was partitioned between CH$_2$Cl$_2$ and sat'd NaHCO$_3$. The organic fraction was dried over Na$_2$SO$_4$, filtered and the filtrate was concentrated. The residue was purified by chomatography (silica, acetone:hexanes, 1:8) to give 1.98 g of the title compound.

¹H NMR (key peaks) (CDCl₃) δ 7.28–7.37 (m, 5H), 7.19–7.22 (m, 2H), 7.01 (t, 2H, J=8.5 Hz);
Mass Spectrum (ESI) m/e=421 (M+1).

EXAMPLE 41

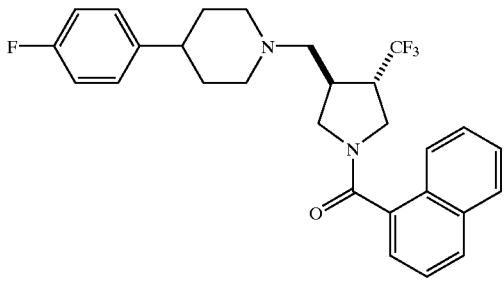

1-(2-Naphthoyl)-3-(RS)-(4-(4-fluorophenyl) piperidinylmethyl)-4-(SR)-(trifluoromethyl)pyrrolidine
Step 1. 3-(RS)-(4-(4-Fluorophenyl)piperidinylmethyl)-4-(RS)-(trifluoromethyl)pyrrolidine

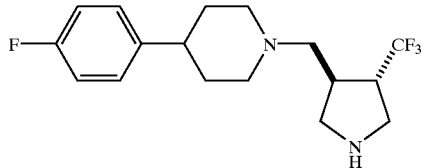

The title compound was prepared from 1-benzyl-3-(RS)-(4-(4-fluorophenyl)piperidinylmethyl)-4-(SR)-(trifluoromethyl)pyrrolidine according to procedures described in Example 3.
Step 2. 1-(1-Naphthoyl)-3-(RS)-(4-(4-fluorophenyl) piperidinylmethyl)-4-(SR)-(trifluoromethyl)pyrrolidine The title compound was prepared from 3-(RS)-(4-(4-fluorophenyl)piperidinylmethyl)-4-(RS)-(trifluoromethyl) pyrrolidine according to procedures described in Example 3, Step 2.
¹H NMR (key peaks) (CDCl₃) d 7.17–7.20 (m, 2H), 6.99 (t, 2H, J=8.5 Hz),
Mass Spectrum (ESI) m/e=331 (M+1).

EXAMPLE 42

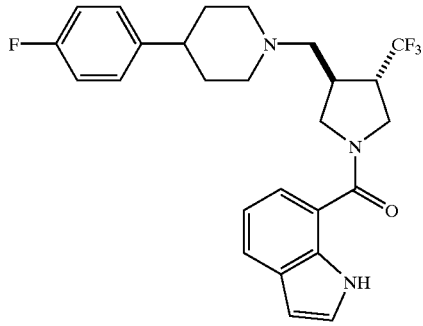

1-(7-Indolecarbonyl)-3-(RS)-(4-(4-fluorophenyl) piperidinylmethyl)-4-(SR)-(trifluoromethyl)pyrrolidine
A solution of 0.12 g (0.36 mmol) of 3-(RS)-(4-(4-fluorophenyl)piperidinylmethyl)-4-(RS)-(trifluoromethyl) pyrrolidine, 0.069 g (0.43 mmol) of indole-7-carboxylic acid, 0.088 g (0.72 mmol) of DMAP and 0.097 g (0.5 mmol) of 1-[3-(Dimethylamino)propyl]-3-ethylcarbodiimide hydrochloride (Aldrich) in 10 mL of CH₂Cl₂ was stirred at rt for 4 h. The reaction mixture was concentrated and the residue was purified by chromatography (silica, acetone:hexanes, 1:5) to give the title compound.
¹H NMR (key peaks) (CDCl₃) δ 9.96 (s, 1H), 7.82 (d, 1H, J=8.0 Hz), 7.44 (d, 1H, J=7.5 Hz), 7.32 (t, 1H, J=3.0 Hz), 7.17–7.21 (m, 3H), 7.03 (t, t, 2H, J=8.5 Hz), 6.62–6.63 (m, 1H);
Mass Spectrum (ESI) m/e=474 (M+1).

EXAMPLE 43

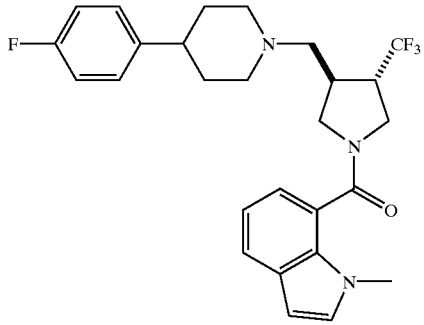

1-(1-Methyl-7-indolecarbonyl)-3-(RS)-(4-(4-fluorophenyl) piperidinylmethyl)-4-(SR)-(trifluoromethyl)pyrrolidine
To a solution of 0.033 g (0.07 mmol) of 1-(7-indolecarbonyl)-3-(RS)-(4-(4-fluorophenyl) piperidinylmethyl)-4-(SR)-(trifluoromethyl)pyrrolidine and 0.022 g (0.084 mmol) of 18-Crown-6 ether in 2 mL of ether at rt was added 0.084 mL of KOt-Bu (1M in t-BuOH). After stirring for 5 min, 0.006 mL (0.098 mmol) of MeI was added and the reaction was stirred for 1 h. The reaction mixture was concentrated and the residue was purified by chromatography (silica, acetone:hexanes, 1:3) to give the title compound.
¹H NMR (CDCl₃) δ (key peaks) 7.68–7.70 (m, 1H), 7.10–7.21 (m, 4H), 7.06 (t, 1H, J=3.0 Hz), 6.97–7.03 (m, 2H), 6.55 (d, 1H, J=3.0 hz);
Mass Spectrum (ESI) m/e=488 (M+1).

EXAMPLE 44

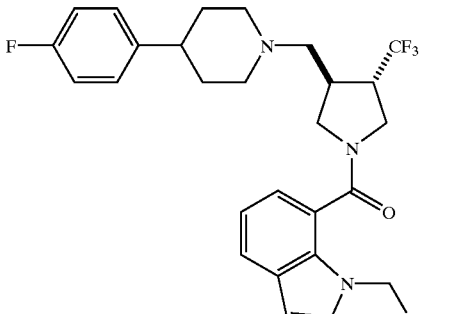

1-(1-t-Butoxycarbonylmethyl)-7-indolecarbonyl)-3-(RS)-(4-(4-fluorophenyl)piperidinylmethyl)-4-(SR)-(trifluoromethyl)pyrrolidine
The title compound was prepared as described in Example 40 using t-butylbromoacetate.
Mass Spectrum (ESI) m/e=588 (M+1).

EXAMPLE 45

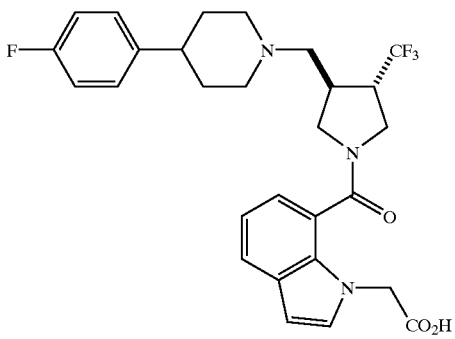

1-(1-Carboxymethyl)-7-indolecarbonyl)-3-(RS)-(4-(4-fluorophenyl)piperidinylmethyl)-4-(SR)-(trifluoromethyl)pyrrolidine A solution of 0.036 g of 1-(1-t-butoxycarbonylmethyl)-7-indolecarbonyl)-3-(RS)-(4-(4-fluorophenyl)piperidinylmethyl)-4-(SR)-(trifluoromethyl)pyrrolidine and 0.05 mL of H$_2$O in 2 mL of TFA was stirred at rt for 40 min. The reaction mixture was concentrated and the residue was purified by chromatography (silica, CH$_2$Cl$_2$, MeOH, NH$_3$, 100:10:3) to give the title compound.

Mass Spectrum (ESI) m/e=532 (M+1).

EXAMPLE 46

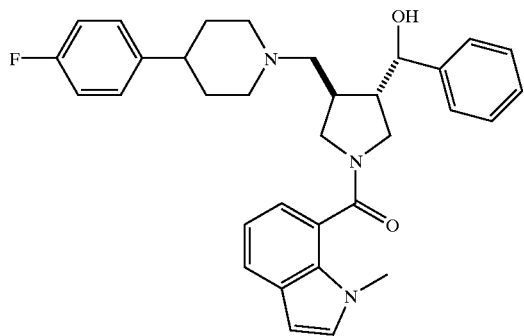

1-(1-Methyl-7-indolecarbonyl)-3-(RS)-(4-(4-fluorophenyl)piperidinylmethyl)-4-(SR)-(phenylhydroxymethyl)pyrrolidine (diastereomers 1 and 2)

Step 1. 1-Benzyl-3-(RS)-(4-(4-fluorophenyl)piperidinylmethyl)-4-(SR)-(phenylhydroxymethyl)pyrrolidine

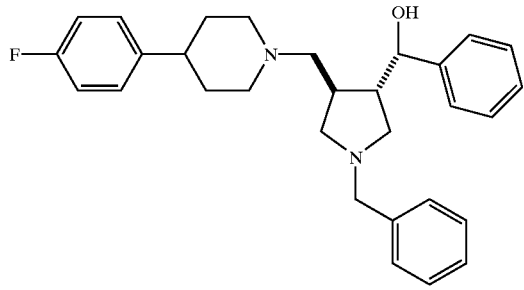

The title compound was prepared from 1-benzyl-3-(RS)-(4-(4-fluorophenyl)piperidinylmethyl)-4-(SR)-formylpyrrolidine according to procedures described in Example 18.

Step 2. 3-(RS)-(4-(4-Fluorophenyl)piperidinylmethyl)-4-(RS)-(phenylhydroxymethyl)pyrrolidine

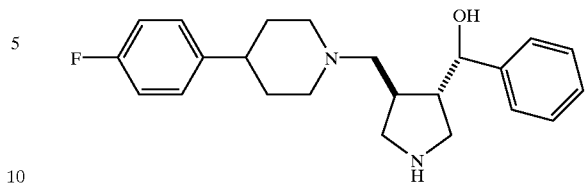

The title compound was prepared from 1-benzyl-3-(RS)-(4-(4-fluorophenyl)piperidinylmethyl)-4-(SR)-(phenylhydroxymethyl)pyrrolidine as described in Example 3.

Step 3. 1-Methylindole-7-carboxylic acid
Step 3A. Benzylindole-7-carboxylate

A solution of 0.68 g (4.2 mmol) of indole-7-carboxylic acid, 0.9 g (8.4 mmol) of benzylalcohol 1.03 g (8.4 mmol) of DMAP and 1.6 g (8.4 mmol) of 1-[3-(Dimethylamino)propyl]-3-ethylcarbodiimide hydrochloride (Aldrich) in 30 mL of CH$_2$Cl$_2$ was stirred at rt for 18 h. The reaction mixture was concentrated and the residue was purified by chromatography (silica, hexanes:ethyl acetate 30:1) to give 0.88 g of the title compound.

Step 3B. Benzyl-1-methyl-7-indolecarboxylate

The title compound (0.15 g) was prepared from benzyl-7-indolecarboxylate according to procedures described in Example 40.

Step 3C. 1-Methyl-7-indolecarboxylic acid

The title compound (0.102 g) was prepared from benzyl-1-methyl-7-indolecarboxylate according to procedures described in Example 3.

Step 4. 1-(1-Methyl-7-indolecarbonyl)-3-(RS)-(4-(4-fluorophenyl)piperidinylmethyl)-4-(SR)-(phenylhydroxymethyl)pyrrolidine The title compound was prepared from 3-(RS)-(4-(4-fluorophenyl)piperidinylmethyl)-4-(RS)-(phenylhydroxymethyl)pyrrolidine and 1-methyl-7-indolecarboxylic acid according to procedures described in Example 39. The crude product was purified by chromatography (silica, acetone:hexane=1:2) to give the separate diastereomers of the title compound.

Diastereomer #1
Mass Spectrum (ESI) m/e=526 (M+1).
Diastereomer #2
Mass Spectrum (ESI) m/e=526 (M+1).

EXAMPLE 47

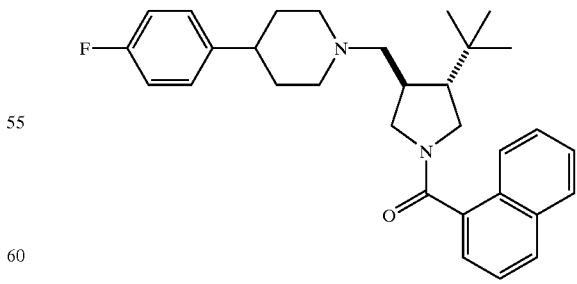

1-(1-Naphthoyl)-3-(RS)-(4-(4-fluorophenyl)piperidinylmethyl)-4-(RS)-(t-butyl)pyrrolidine
Step 1. methyl-3-t-butylacrylate To a solution of 22.8 g (125 mmol) of trimethylphosphonoacetate in 25 mL of THF at −20° C. was added 125 mL (125 mmol) of a solution of sodium bis(trimethylsilyl)amide (1 M) in THF. After stirring for 20 min, 7.7 g (aoo mmol) of trimethylacwetaldehyde and the reaction mixture was stirred at −20° C. for 2 h. The reaction mixture was partitioned between H₂O and ether. The organic fractrion was washed with H₂O, and sat'd NaCl solution, dried over MgSO₄, and filtered. The filtrate was concentrated to give the title compound which was used without further purification.

Step 2. N-allyl-N-(trimethylsilylmethyl)amine

To 118 mL (1.57 mol) of allylamine warmed at 40° C. in an inert atmosphere was very slowly added 100 mL (0.72 mol) of chloromethyl trimethylsilane (approximate rate of 1 mL/min). The reaction mixture was slowly warmed to 70° C. and stirred for 24 h. The reaction mixture was cooled to 0° C. and to it was added water to break up the gel and then 300 mL of 2N NaOH solution. The reaction mixture was extracted with ether. The combined organic fractions were washed with 500 mL of sat'd NaCl solution, dried over Na₂SO₄, filtered and the filtrate was concentrated. The residue was purified by distillation (bp 80–84° C.@100 torr) to give 75 g of the title compound.

Step 3. N-Allyl-N-(methoxymethyl)-N-trimethylsilylmethyl)amine

To 75 g (0.57 mol) of N-allyl-N-(trimethylsilylmethyl) amine at 0° C. was slowly added 67 mL (0.88 mol) of aqueous formaldehyde (37% w/w). After stirring for 5 min, 65 mL (1.6 mol) of methanol was added followed by the addition of 94 g (0.68 mol) of K₂CO₃. The reaction mixture was warmed to rt and stirred for 12 h. The reaction mixture was partitioned between 300 mL of water and 300 mL of ether. The organic fraction was washed with water and sat. NaCl solution. The combined aqueous fractions were extracted with ether. The combined organic fractions were dried over Na₂SO₄, filtered and the filtrate was concentrated to give 89 g of the title compound which was used without further purification.

Step 4. 1-Allyl-3-(SR)-carbomethoxy-4-(RS)-t-butylpyrrolidine

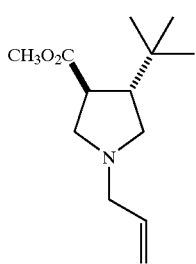

To a solution of 7.1 g (50 mmol) of methyl-3-t-butylacrylate, 18.7 g (100 mmol) of N-allyl-N-(methoxymethyl)-N-trimethyl silylmethyl)amine in 150 mL of CH₂Cl₂ at 0° C. was added 0.8 mL (10 mmol) of trifluoroacetic acid and the reaction mixture was stirred for 4 h while warming to rt. The reaction mixture was diluted with sat'd NaHCO₃ and extracted twice with 100 mL of ether. The combined organic fractions were washed with sat'd NaHCO₃ and NaCl solutions, dried over Na₂SO₄, filtered and the filtrate was concentrated. The residue was filtered through a thin pad of silica, eluting with acetone: hexanes (3:7) to give 6.7 g of the title compound.

Mass Spectrum (ESI) m/e=226 (M+1).

Step 5. 1-Allyl-3-(RS)-(4-(4-fluorophenyl) piperidinylmethyl)-4-(RS)-t-butylpyrrolidine

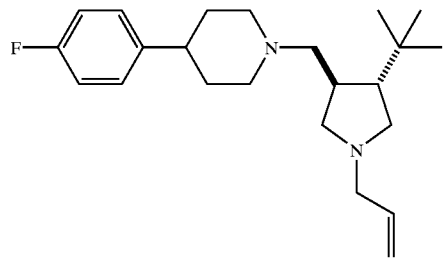

The title compound was prepared as described in Example 37.

¹H NMR (CDCl₃) δ 7.19 (m, 2H), 6.98 (t, 8.7 Hz, 2H), 5.94 (m, 1H), 5.21 (d of d, 1.8 Hz, 7.2 Hz, 1H), 5.11 (d of d, 0.9Hz, 10Hz, 1H), 3.14 (m, 2H), 2.97 (m, 2H), 2.79 (m, 2H), 2.48 (m, 2H), 2.29 (m, 2H), 2.22 (m, 1H), 2.19–2.05 (m, 3H), 1.92 (m, 1H), 1.82–1.64 (m, 4H), 1.55 (m, 1H), 0.90 (s, 9H);

Mass Spectrum (ESI) m/e=359 (M+1).

Step 6. 3-(SR)-(4-(4-Fluorophenyl)piperidinylmethyl)-4-(RS)-t-butylpyrrolidine

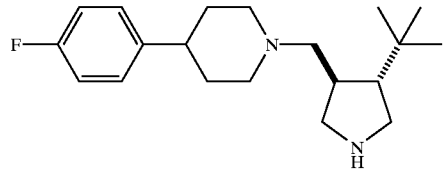

A mixture of 1 g (2.7 mmol) of 1-allyl-3-(RS)-(4-(4-fluorophenyl)piperidinylmethyl)-4-(RS)-t-butylpyrrolidine and 0.13 g (0.14 mmol) of Wilkinson's catalyst [Rh(PPh₃)₃Cl] in 40 mL of an 85% solution of CH₃CN and water was heated to 90° C. and stirred for 3 h. The reaction mixture was cooled to rt and concentrated. The residue was partitioned between EtOAc and water. The organic fraction was washed with sat. NaHCO₃, dried over Na₂SO₄, filtered and the filtrate was concentrated. The residue was purified by chromatography (silica, CHCl₃:MeOH:NH₃, 90:10:1) to give 0.75 g of the title compound.

Step 6. 1-(1-Naphthoyl)-3-(RS)-(4-(4-fluorophenyl) piperidinyl-methyl)-4-(RS)-(t-butyl)pyrrolidine The title compound was prepared from 3-(SR)-(4-(4-fluorophenyl)piperidinylmethyl)-4-(RS)-t-butylpyrrolidine according to procedures described in Example 3, Step 2.

¹H NMR (CDCl₃) (key peaks) δ 7.89 (m, 3H), 7.58–7.43 (m, 4H), 7.21, 7.08 (m, 2H), 7.01, 6.95 (m, 2H), 0.82, 0.99 (s, 9H);

Mass Spectrum (ESI) m/e=473 (M+1).

EXAMPLE 48

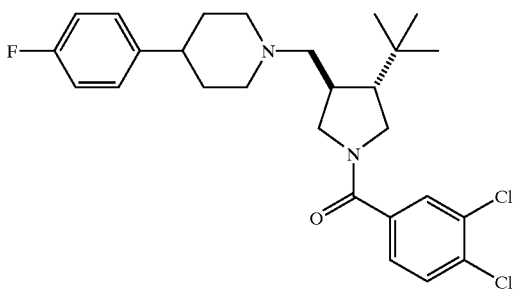

1-(3,4-Dichlorobenzoyl)-3-(RS)-(4-(4-fluorophenyl) piperidinylmethyl)-4-(RS)-(t-butyl)pyrrolidine The title compound was prepared from 3-(SR)-(4-(4-fluorophenyl)piperidinylmethyl)-4-(RS)-t-butylpyrrolidine according to procedures described in Example 3, Step 2.

Mass Spectrum (ESI) m/e=491 (M+1 35Cl, 35Cl) 493 (M+1 37Cl, 37Cl)

EXAMPLE 49

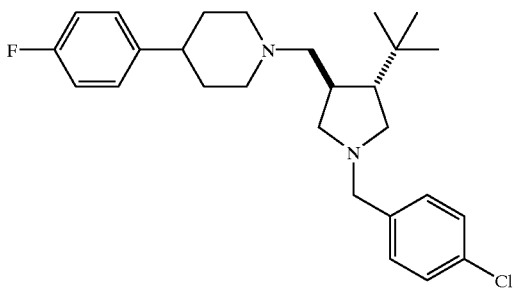

1-(4-Chlorobenzyl)-3-(RS)-(4-(4-fluorophenyl) piperidinylmethyl)-4-(RS)-(t-butyl)pyrrolidine A solution of 0.025 g (0.08 mmol) of 3-(SR)-(4-(4-fluoro phenyl)piperidnylmethyl)-4-(RS)-t-butylpyrrolidine, 0.022 g (0.16 mmol) of 4-chlorobenzaldehyde and 0.043 g (0.2 mmol) of sodium triacetoxy borohydride in 5 mL of 1,2-dichloroethane was stirred for 2 h at rt. The reaction mixture was partitioned between ether and sat'd $K_2CO_3$ solution. The aqueous layer was extracted with ethyl acetate and the combined organic fractions were dried over $Na_2SO_4$, filtered and the filtrate was concentrated. The residue was purified by chromatography (silica, acetone: hexanes, 1:3) to give the title compound.

Mass Spectrum (ESI) m/e=457 (M+1 35Cl) 459 (M+1 37Cl).

EXAMPLE 50

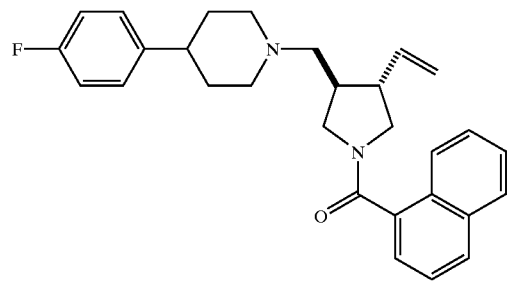

1-(1-Naphthoyl)-3-(RS)-(4-(4-fluorophenyl) piperidinylmethyl)-4-(SR)-(vinyl)pyrrolidine To a suspension of 0.08 g (0.22 mmol) of methyltriphenyl phosphonium bromide ($Ph_3PCH_3Br$) in 4 mL of THF at rt was added 0.36 mL of potassium bis(trimethylsily)amide and the reaction mixture was stirred for 30 min. The reaction mixture was cooled to 0° C. and to it was added a solution of 0.04 g (0.089 mmol) of 1-(1-naphthoyl)-3-(RS)-(4-(4-fluorophenyl)piperidinylmethyl)-4-(SR)-(formylpyrrolidine in 2 mL of THF. The reaction mixture was warmed to rt and stirred for 1.2 h. The reaction mixture was filtered through a thin pad of silica eluting with acetone: hexanes, 1:2, then concentrated. The residue was purified by chromatography (silica, acteone: hexanes, 1:2) to give the title compound.

Mass Spectrum (ESI) m/e=444 (M+1).

EXAMPLE 51

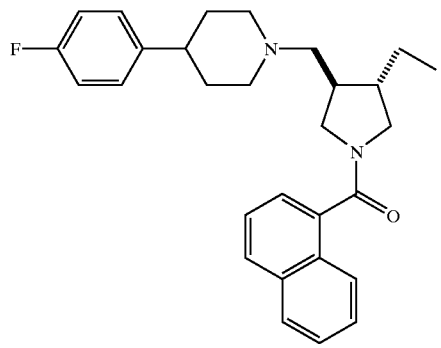

1-(1-Naphthoyl)-3-(RS)-4-(4-fluorophenyl) piperidinylmethyl)-4-(SR)-(ethyl)pyrrolidine A mixture of 0.023 g (5 mmol) of 1-(1-Naphthoyl)-3-(RS)-4-(4-fluorophenyl)piperidinylmethyl)-4-(SR)-(vinyl) pyrrolidine and 0.025 g of Pd/C (10%) in 8 mL of $CH_3OH$ was hydrogenated under $H_2$ (50 psi) for 72 h. The reaction mixture was filtered and concentrated to give the title compound.

Mass Spectrum (CI) m/e 444 (M+1).

EXAMPLE 52

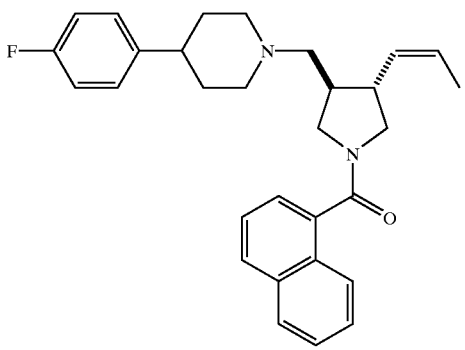

1-(1-Naphthoyl)-3-(RS)-4-(4-fluorophenyl) piperidinylmethyl)-4-(SR)-(prop-1-enyl)pyrrolidine The title compound was prepared according to procedures described in Example 50.

Mass Spectrum (CI) m/e 457 (M+1).

EXAMPLE 53

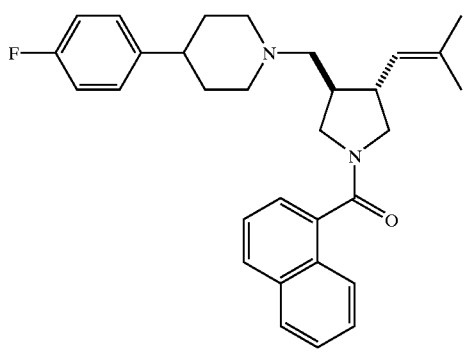

1-(1-Naphthoyl)-3-(RS)-4-(4-fluorophenyl)piperidinylmethyl)-4-(SR)-(2-methylprop1-enyl)pyrrolidine The title compound was prepared according to procedures described in Example 50.

Mass Spectrum (CI) m/e 471 (M+1).

EXAMPLE 54

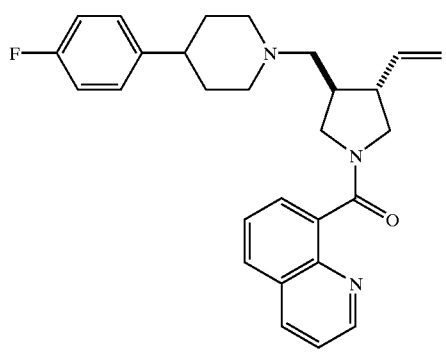

1-(8-Quinolinecarbonyl)-3-(RS)-4-(4-fluorophenyl)piperidinylmethyl)-4-(SR)-(vinyl)pyrrolidine The title compound was prepared from 3-(RS)-4-(4-fluorophenyl)piperidinylmethyl)-4-(SR)-(vinyl)pyrrolidine and 8-quinolinecarboxylic acid as described in Example 43.

Mass Spectrum (CI) m/e 444 (M+1).

Preparation of 3-(RS)-4-(4-fluorophenyl)piperidinylmethyl)-4-(SR)-(vinyl)pyrrolidine Step 1. 1-Benzyl-3-(RS)-(4-fluorophenyl)piperidinylmethyl)-4-(SR)-(formyl)pyrrolidine

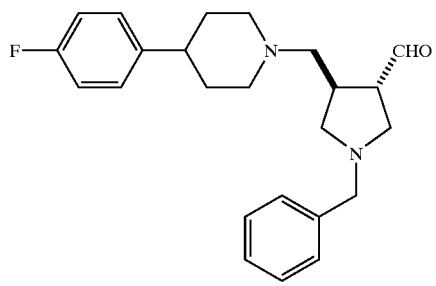

The title compound was prepared from 1-benzyl-3-(RS)-(4-fluorophenyl)piperidinylmethyl)-4-(SR)-(hydroxymethyl)pyrrolidine (Example 2) according to procedures described in Example 4.

Step 2. 1-Benzyl-3-(RS)-(4-fluorophenyl)piperidinylmethyl)-4-(SR)-(vinyl)pyrrolidine

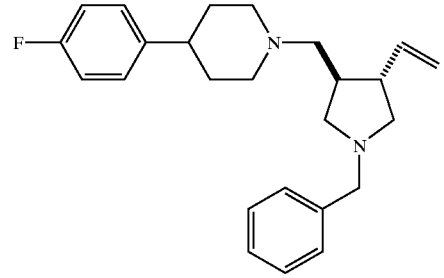

The title compound was prepared from 1-benzyl-3-(RS)-(4-fluorophenyl)piperidinylmethyl)-4-(SR)-(formyl)pyrrolidine according to procedures described in Example 50.

Step 3. 1-(2,2,2-Trichloroethoxycarbonyl)-3-(RS)-(4-Fluorophenyl)piperidinylmethyl)-4-(SR)-(vinyl)pyrrolidine

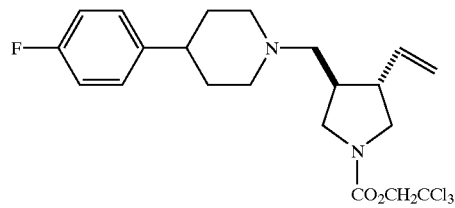

To a solution of 0.625 g (1.4 mmol) of 1-benzyl-3-(RS)-(4-fluorophenyl)piperidinylmethyl)-4-(SR)-(vinyl)pyrrolidine in 5 mL of THF at rt was added 0.21 mL (1.55 mmol) of 2,2,2-Trichloroethylchloroformate and the reation mixture was stirred for 1 h. The reaction mixture was diluted with ether and was washed with sat'd NaHCO$_3$ and NaCl solutions, dried over Na$_2$SO$_4$, filtered and the filtrate was concentrated. The residue was purified by chromatography (silica, hexanes: EtOAc, 4:1) to give 0.76 g of the title compound.

Step 4. 3-(RS)-(4-Fluorophenyl)piperidinylmethyl)-4-(SR)-(vinyl)pyrrolidine

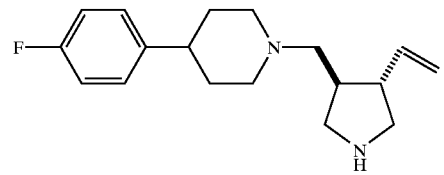

A mixture of 0.76 g (1.4 mmol) of 1-(2,2,2-trichloroethoxy carbonyl)-3-(RS)-(4-Fluorophenyl)piperidinylmethyl)-4-(SR)-(vinyl)pyrrolidine and 0.45 g (7 mol) of Mg in 4 mL of HOAc was heated at 40° C. for 40 min. The reaction mixture was filtered through a thin pad of Celite and the filtrate was concentrated. The residue was dissolved in ether and the solution was washed with sat'd NaHCO$_3$ and NaCl solutions, dried over Na$_2$SO$_4$, filtered and the filtrate was concentrated to give 0.28 g of the title compound.

EXAMPLE 55

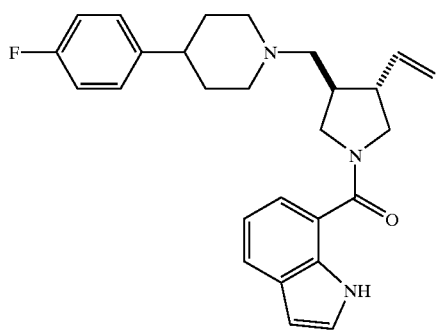

1-(7-Indolecarbonyl)-3-(RS)-4-(4-fluorophenyl)piperidinylmethyl)-4-(SR)-(vinyl)pyrrolidine The title compound was prepared from 3-(RS)-4-(4-fluorophenyl)piperidinylmethyl)-4-(SR)-(vinyl)pyrrolidine (Example 54) and 7 indolecarboxylic acid as described in Example 43.

Mass Spectrum (CI) m/e 432 (M+1).

EXAMPLE 56

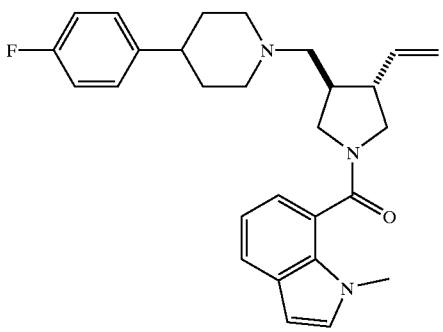

1-(1-Methyl-7-indolecarbonyl)-3-(RS)-4-(4-fluorophenyl)piperidinylmethyl)-4-(SR)-(vinyl)pyrrolidine The title compound was prepared from 1-(7-indolecarbonyl)-3-(RS)-4-(4-fluorophenyl)piperidinylmethyl)-4-(SR)-(vinyl)pyrrolidine according to procedures described in Example 43.

Mass Spectrum (CI) m/e 446 (M+1).

EXAMPLE 57

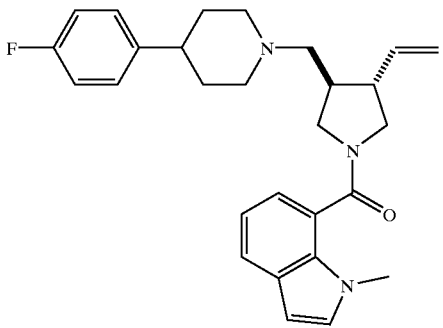

1-(1-Methyl-7-indolecarbonyl)-3-(RS)-4-(4-fluorophenyl)piperidinylmethyl)-4-(S)-(vinyl)pyrrolidine Step 1. N-trans-3-(Ethoxycarbonyl)acryloyl-4-(S)-benzyl-2-oxazolidinone

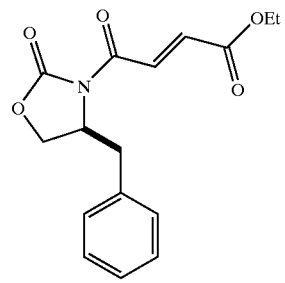

To a solution of 14.4 g (100 mmol) of monoethyl fumarate and 16.7 mL (120 mmol) of triethylamine in 350 mL of THF at 0° C. was added 12.7 g (105 mmol) of pivaloyl chloride. The reaction mixture was allowed to warm to rt and was stirred for 2 h, then was cooled to −78° C.

Meanwhile, to a solution of 18.6 g (105 mmol) of (S)-benzyl-2-oxazolidinone in 200 mL of THF at −78° C. under nitrogen, was added 75 mL of n-butyllithium (1.6M, 120 mmol) and the solution was stirred for 30 min at −78° C. This was added via cannula to the first solution. After addition was complete, the solution was allowed to warm to room temperature for 2 h.

The reaction was quenched by addition of saturated aqueous $NH_4Cl$ and the mixture was extracted with ethyl acetate. The organic layer was washed with brine, dried over $MgSO_4$, and filtered. The solution was concentrated followed by silica gel chromatography (25% ethyl acetate/hexane) to afford 21.4 g the title compound;

$^1$H NMR ($CDCl_3$) δ 8.15 (d, 1H, J=16 Hz), 6.98 (d, 1H, J=16 Hz), 4.65–4.80 (m, 1H), 4.10–4.33 (m, 5H), 3.28 (d of d, 1H, J=13.5, 3.2 Hz), 2.81 (d of d, 1H, J=13.3, 9.4 Hz), 1.21–1.35 (m, 3H);

Mass spectrum (ESI) m/e=304 (M+1).

Step 2. (S)-N-[(1-Benzyl)-4-(S)-(ethoxycarbonyl)-3-(R)-pyrolidinylcarbonyl]-4-benzyl-2-oxazolidinone and (S)-N-[(1-Benzyl)-4-(R)-(ethoxycarbonyl)-3-(S)-pyrolidinylcarbonyl]-4-benzyl-2-oxazolidinone

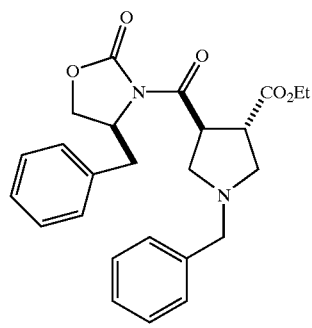

To a solution of 20 g (66 mmol) of N-trans-3-(ethoxycarbonyl) acryloyl-4-(S)-benzyl-2-oxazolidinone (Step 1) in 200 mL of $CH_2Cl_2$ at 0° C. was added 16.6 g (70 mmol) of N-methoxymethyl-N-trimethylsilylmethylbenzylamine, and 1 mL (13.4 mmol) of trifluoroacetic acid and the solution was stirred at 0° C. for 2 h under nitrogen. The solution was poured into sat'd $NaHCO_3$ solution and the layers were separated. The aqueous layer was washed with $CH_2Cl_2$ and the combined organic fractions were washed with sat'd NaCl solution, dried over $MgSO_4$, filtered, and the filtrate was concentrated. The residue was purified by silica gel chromatography (ethyl acetate: hexanes, 1:4) to afford 10.1 g of the title compound (S)-N-[(1-Benzyl)-4-(S)-(ethoxycarbonyl)-3-(R)-pyrrolidinylcarbonyl]-4-benzyl-2-oxazolidinone.

$^1$H NMR (CDCl$_3$) δ 7.18–7.37 (m, 10H), 4.33–4.38 (m, 1H), 4.48–4.44 (m, 1H), 3.71 (d, 1H, J=13.1 Hz), 3.61 (d, 1H, J=13.1Hz), 1.26 (t, 7.1Hz);

Mass spectrum (ESI) m/e=437 (M+1).

Further elution afforded the title compond (S)-N-[(1-Benzyl)-4-(R)-(ethoxycarbonyl)-3-(S)-pyrrolidinylcarbonyl]-4-benzyl-2-oxazolidinone;

$^1$H NMR (CDCl$_3$) δ 7.22–7.36 (m, 10H), 4.67–4.71 (m, 1H), 4.44–4.48 (m, 1H), 3.61 (d, 1H, J=13.1 Hz), 3.67 (d, 1H, J=13.1Hz), 1.28 (t, 7.1Hz);

Mass spectrum (ESI) m/e=437 (M+1).

Step 3. 1-Benzyl-3-(S)-(n-propanethiocarbonyl)4-(S)-(ethoxycarbonyl)pyrrolidine

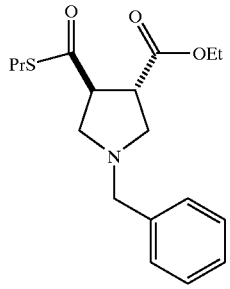

To a cooled (−78° C.) solution of 5.7 g (75.0 mmol) of propanethiol in 250 mL THF was added 34.4 mL n-butyllithium (1.6M, 55.0 mmol) and the solution was stirred for 45 min at −78° C. under nitrogen and then warmed to −10° C. To the resulting white suspension was added a solution of 9.6 g (22.0 mmol) of (S)-N-[(1-Benzyl)-4-(R)-(ethoxycarbonyl)-3-(S)-pyrrolidinylcarbonyl]-4-benzyl-2-oxazolidinone in 250 mL THF. The reaction was stirred for 30 min and then removed from the bath and allowed to warm to rt over 1 h. The clear solution was partitioned between 1.5 L of ether and 500 mL of 1M NaOH and the layers were separated. The aqueous layer was washed with ether and the combined organic fractions were washed with sat'd NCl solution, dried over MgSO$_4$, filtered, and the filtrate was concentrated. The residue was purified by silica gel chromatography (acetone: hexanes, 1:4) to afford 6.6 g of the title compound;

Mass spectrum (ESI) m/e=336 (M+1).

Step 4. 1-Benzyl-3-(S)-(formyl)-4-(S)-(ethoxycarbonyl)pyrrolidine

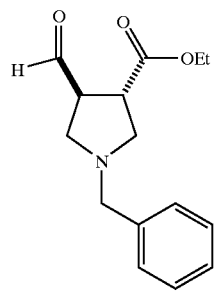

To a mixture of 0.375 g of 10% Pd/C and 6.5 g (19.4 mmol) of 1-benzyl-3-(S)-(n-propanethiocarbonyl)-4-(S)-(ethoxycarbonyl)pyrrolidine in 30 mL acetone was added dropwise 7.5 mL (47.0 mmol) of triethylsilane over 15 min. The mixture was allowed to stir for 45 min after addition was complete. The reaction mixture was filtered through a thin pad of celite and the filtrate was concentrated. The residue was purified by chromatography (silica, acetone:hexanes, 1:4) to give 4.2 g of title compound;

$^1$H NMR (CDCl$_3$) δ 9.69 (s, 1H), 7.25–7.33 (m, 5H), 4.18 (q, 2H, J=7.1Hz), 4.44–4.48 (m, 1H), 3.61 (d, 1H, J=13.5 Hz), 3.64 (d, 1H, J=13.5Hz), 3.32 (m, 1H), 3.46 (m,1H), 1.27 (t, 7.1Hz);

Mass spectrum (ESI) m/e=262 (M+1).

Step 5. 1-Benzyl-3-(R)-4-(4-fluorophenyl)piperidinylmethyl)-4-(S)-(ethoxycarbonyl)pyrrolidine

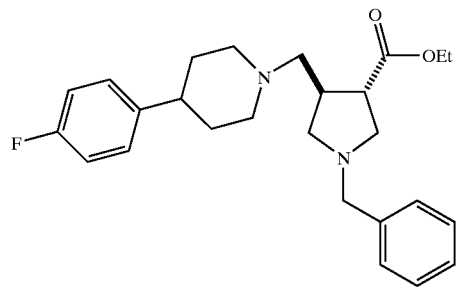

To a solution of 40 g (15.3 mmol) of 1-benzyl-3-(S)-(formyl)-4-(S)-(ethoxycarbonyl)pyrrolidine in 50 mL of dichloroethane at 0° C. was added 3.3 g (18.4 mmol) of 4-fluorophenyl-4-piperidine and the reaction mixture was allowed to stir for 15 min. To the reaction mixture was added 6.7 g (32.0 mmol) of sodium triacetoxyborohydride and the solution was stirred for 30 min then it was warmed to rt. The reaction mixture was quenched with 15 mL saturated KHCO$_3$ solution, partitioned between 300 mL of ether and 10 mL of water and the layers were separated. The aqueous layer was washed with 10 mL of ethyl acetate and the combined organic fractions were washed with sat'd NaCl solution, dried over MgSO$_4$, filtered, and the filtrate was concentrated. The residue was purified by chromatography (silica, acetone: hexanes, 1:4) to afford 5.32 g of the title compound;

$^1$H NMR (CDCl$_3$) δ 7.18–7.33 (m, 7H), 6.95–7.00 (m, 2H), 4.15 (q, 2H, J=7.0 Hz), 4.44–4.48 (m, 1H), 3.65 (d, 1H, J=12.6 Hz), 3.56 (d, 1H, J=12.6 Hz), 3.40 (m, 1H), 3.03 (m,2H), 2.45 (m, 2H), 2.07 (m, 2H), 1.6–1.8 (m, 4H), 1.23 (t, 7.0 Hz);

Mass spectrum (ESI) m/e=425 (M+1).

Step 6. 1-Benzyl-3-(R)-4-(4-fluorophenyl)piperidinylmethyl)-4-(S)-(formyl)pyrrolidine

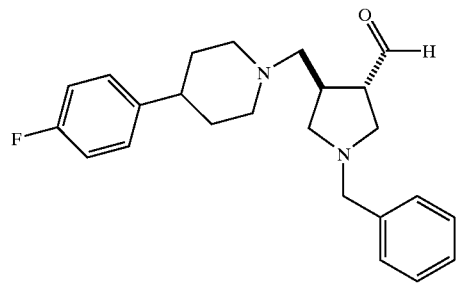

To a cooled (−65° C.) solution of 2.1 g (50.0 mmol) of 1-benzyl-3-(R)-4-(4-fluorophenyl)piperidinylmethyl)-4-(S)-(ethoxycarbonyl)pyrrolidine in 100 mL toluene was added 43.5 mL of diisobutylaluminum hydride (DIBAL-H) (1.5 M in toluene, 65.0 mmol) dropwise over 30 min and the solution was stirred for 2 h at −60–65° C. under nitrogen. The reaction was quenched with 1 mL MeOH and removed from bath and allowed to stir at rt for 10 min. To the solution was added 200 mL of saturated Rochelles salt solution and 100 mL ethyl acetate and the mixture was stirred until the solution cleared. The layers were separated and the organic fraction was washed with sat'd NaCl solution, dried over MgSO$_4$, filtered, and the filtrate was concentrated. The residue was purified by chromatography (silica, acetone: hexanes, 1:4) to afford 1.49 g of the title compound;

Mass spectrum (ESI) m/e=381 (M+1).

Step 7. 1-Benzyl-3-(R)-4-(4-fluorophenyl) piperidinylmethyl)-4-(S)-(vinyl)pyrrolidine

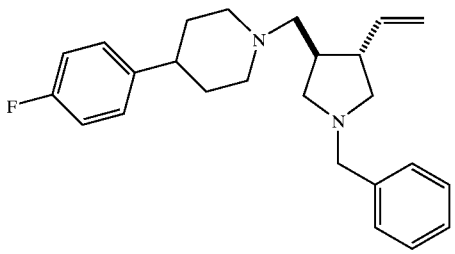

To a mixture of 1.65 g (4.62 mmol) methyl triphenylphosponium bromide in 10 mL THF at −78° C. was added 8.6 mL of potassium bis(trimethylsilyl)amide (KHMDS, 0.5M in toluene, 4.3 mmol) and the solution was stirred for 30 min at −78° C. under nitrogen. To this mixture was added a solution of 1.25 g (3.3 mmol) of 1-benzyl-3-(R)-4-(4-fluorophenyl)piperidinylmethyl)-4-(S)-(formyl) pyrrolidine in 5 mL THF. The reaction was warmed to rt over 2 h. The reaction was partitioned between ethyl acetate and water. The organic fraction was washed with sat'd NaCl solution, dried over MgSO$_4$, filtered, and the filtrate was concentrated. The residue was purified by chromatography (silica, acetone: hexanes, 1:4) to afford 0.98 g of the title compound;

Mass sptectrum (ESI) m/e=379 (M+1).

Step 8. 3(R)-4-(4-fluorophenyl)piperidinylmethyl)-4-(S)-(vinyl) pyrrolidine

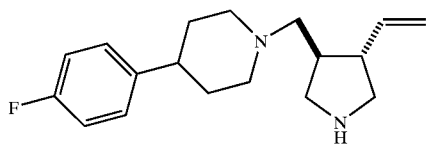

To a solution of 0.9 g (2.38 mmol) of 1-benzyl-3-(R)-4-(4-fluorophenyl)piperidinylmethyl)-4-(S)-(vinyl)pyrrolidine in 20 mL THF at at 0° C. was added 0.69 mg (2.65 mmol) of 9-fluorenylmethoxycarbonylchloride (FMOC-Cl) and the solution was stirred for 1 h. The reaction was partitioned between ethyl acetate and sat'd NaHCO$_3$ solution and the layers were separated. The aqueous layer was washed with ethyl acetate and the combined organic fractions were washed with sat'd NaCl solution, dried over MgSO$_4$, filtered, and the filtrate was concentrated. The residue was filtered through a pad of silica with 30% ethyl acetate/hexane and concentrated. The residue was dissolved in 5 mL DMF and 1 mL of diethylamine was added and the solution was stirred for 2 h at rt under nitrogen. An additional 0.5 mL diethylamine was added and allowed to stir 1 hr. The reaction was concentrated and the residue dissolved in dichloromethane and filtered through a pad of silica with 30% ethyl acetate/hexane to remove impurities and then the pad of silica was washed with CHCL$_3$/MeOH/NH$_{3(aq)}$ (90:10:1) and concentrated to collect 0.512 g of the title compound;

Mass spectrum (ESI) m/e=289 (M+1).

Step 9. 1-(1-Methyl-7-indolecarbonyl)-3-(R)-4-(4-fluorophenyl)piperidinylmethyl)4-(S)-(vinyl)pyrrolidine The title compound was prepared from 3-(R)-4-(4-fluorophenyl)piperidinylmethyl)-4-(S)-(vinyl) pyrrolidine and 1-methylindole-7-carboxylic acid (Example 47, Step 3) according to procedures described in Example 43. The residue was purified by chomatography (HPLC Waters Nova-Pak Silica 25X10 RCM 25–40% acetone in hexanes) to give the title compound.

$^1$H NMR (CD3OD) δ 7.66 (m,1H), 6.98–7.26 (m, 7H), 6.50 (m, 1H), 5.60–5.88 (m, 1H), 5.18–5.38 (m, 2H), 4.00–4.34 (m, 1H), 3.80 (m, 3H), 2.55–3.75 (m, 12H), 1.93–2.09 (m, 4H);

Mass spectrum (ESI) m/e=446 (M+1). [α]$_D$=−38.8 (c=0.025, CHCl$_3$).

EXAMPLE 58

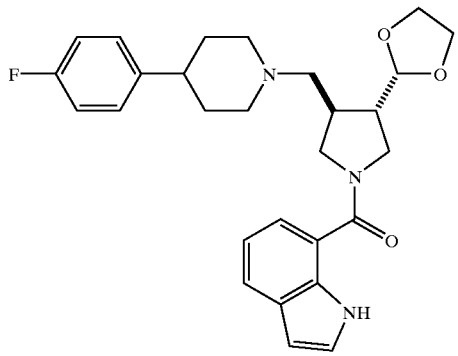

1-(7-Indolecarbonyl)-3-(RS)-4-(4-fluorophenyl) piperidinylmethyl)4-(SR)-(1,3-dioxolan-2-yl)pyrrolidine The title compound was prepared from 3-(RS)-(4-(4-fluorophenyl)piperidinylmethyl)-4-(SR)-(1,3-dioxolan-2-yl)pyrrolidine (Example 33, Step 3) and 7-indolecarboxylic acid according to procedures described in Example 42.

Mass Spectrum (CI) m/e 478 (M+1).

EXAMPLE 59

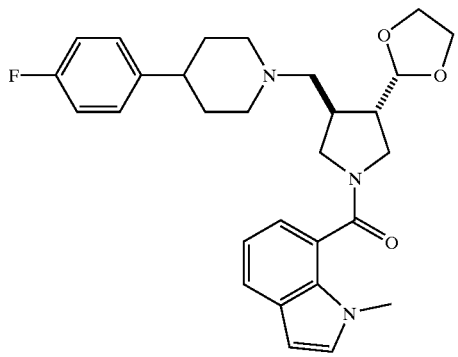

1-(1-Methyl-7-indolecarbonyl)-3-(RS)-4-(4-fluorophenyl) piperidinylmethyl)4-(SR)-(1,3-dioxolan-2-yl)pyrrolidine The title compound was prepared from 1-(7-indolecarbonyl)-3-(RS)-4-(4-fluorophenyl)

piperidinylmethyl)-4-(SR)-(1,3-dioxolan-2-yl)pyrrolidine according to procedures described in Example 43.

Mass Spectrum (CI) m/e 492 (M+1).

EXAMPLE 60

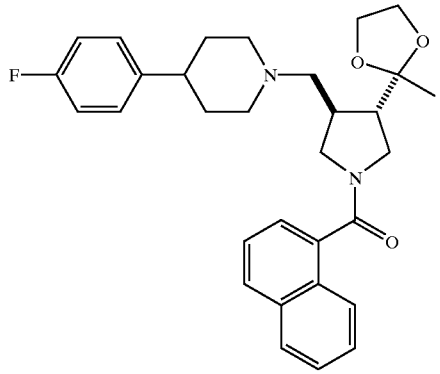

1-(1-Naphthoyl)-3-(RS)-4-(4-fluorophenyl) piperidinylmethyl)-4-(SR)-(2-methyl-1,3-dioxolan-2-yl) pyrrolidine The title compound was prepared from 1-(1-naphthoyl)-3-(RS)-4-(4-fluorophenyl)piperidinylmethyl)-4-(SR)-(acetyl)pyyrolidine (Example 27) according to procedures described in Example 33.

Mass Spectrum (CI) m/e 503 (M+1).

EXAMPLE 61

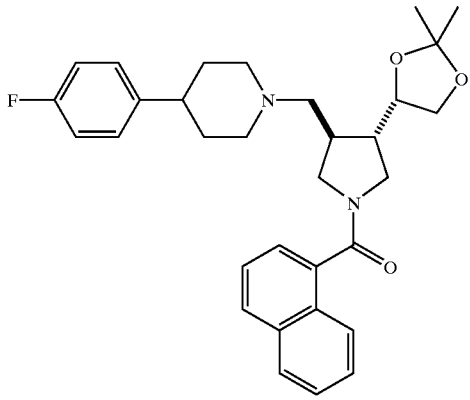

1-(1-Naphthoyl)-3-(RS)-4-(4-fluorophenyl) piperidinylmethyl)-4-(SR)-(2,2-dimethyl-1,3-dioxolan-5-yl)pyrrolidine Step 1. 1-(1-Naphthoyl)-3-(RS)-4-(4-fluorophenyl) piperidinylmethyl)-4-(SR)-(1,2-dihydroxyethyl)pyrrolidine

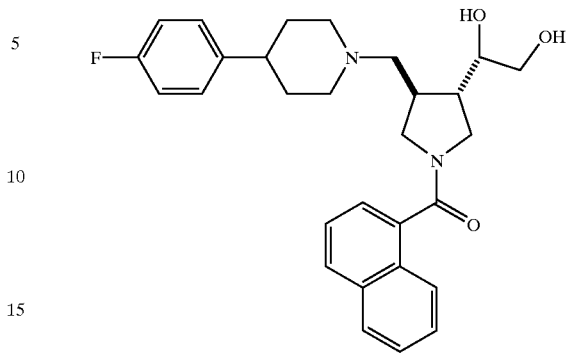

To a solution of 0.023 g (0.05 mmol) of 1-(1-Naphthoyl)-3-(RS)-4-(4-fluorophenyl)piperidinylmethyl)-4-(SR)-(vinyl)pyrrolidine (Example 50) in 1 mL of pyridine, 2 mL of THF and 1 mL of $H_2O$ at rt was added 0.016 g (0.06 mmol) of $OsO_4$, and the reaction was stirred for 2 h. The reaction mixture was diluted with THF and H2S gas was bubbled through it for 5 min. The reaction mixture was filtered through a thin pad of celite and the filtrate was concentrated. The residue was purified by chromatography (silica, $CH_2Cl_2$: $NH_3$ (2N in $CH_3OH$), 95:5) to give 0.013 g of the title compound.

Step 2. 1-(1-Naphthoyl)-3-(RS)-4-(4-fluorophenyl) piperidinylmethyl)-4-(SR)-(2,2-dimethyl-1,3-dioxolan-5-yl)pyrrolidine A solution of 0.013 g (0.027 mmol) of 1-(1-naphthoyl)-3-(RS)-4-(4-fluorophenyl)piperidinylmethyl)-4-(SR)-(1,2-dihydroxyethyl)pyrrolidine, 0.2 mL (1.6 mmol) of 2,2-dimethoxypropane and 0.1 g of p-toluenesulfonic acid in 2 mL of DMF was stirred at rt ro 16 h. The reaction mixture as concentrated and the residue was dissolved in ehter. The ehter solution was washed with sat'd $NaHCO_3$ and sat'd NaCl solutions, dried over $MgSO_4$, filtered and the filtrate was concentrated. The residue as purified by chromatography (silica, hexanes, EtOAc: NH3 (2N in $CH_3OH$), 10:10:1) to give the two isomers of the title compound.

Isomer #1
  Mass Spectrum (CI) m/e 517 (M+1).
Isomer #2
  Mass Spectrum (CI) m/e 517 (M+1).

EXAMPLE 62

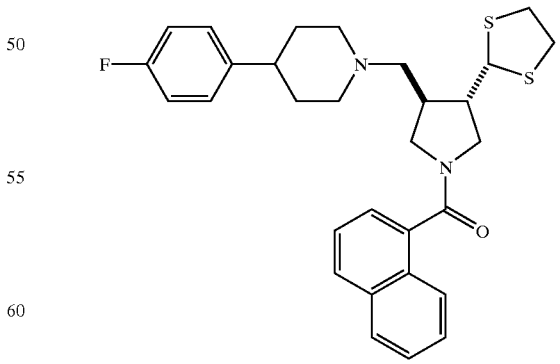

1-(1-Naphthoyl)-3-(RS)-4-(4-fluorophenyl) piperidinylmethyl)-4-(SR)-(1,3-dithiolan-2-yl)pyrrolidine A solution of 0.11 g (0.254 mmol) of 1-(1-naphthoyl)-3-(RS)-4-(4-fluorophenyl)piperidinylmethyl)-4-(SR)-(formyl)

pyrrolidine, 0.043 mL (0.5 mmol) of 1,2-ethanedithiol and 0.042 mL (0.3 mmol) of BF$_3$.2HOAc in 4 mL of CH$_2$Cl$_2$ was stirred at rt for 2 h. The reaction mixture was diluted with ether and was washed with sat'd NaHCO$_3$ and NaCl solutions, dried over Na$_2$SO$_4$, filtered and the filtrate was concentrated. The residue was purified by chromatography (silica, hexanes: EtOAc: NH$_3$ (2N CH$_3$OH), 20:20:1) to give the title compound.

Mass Spectrum (CI) m/e 521 (M+1).

EXAMPLE 63

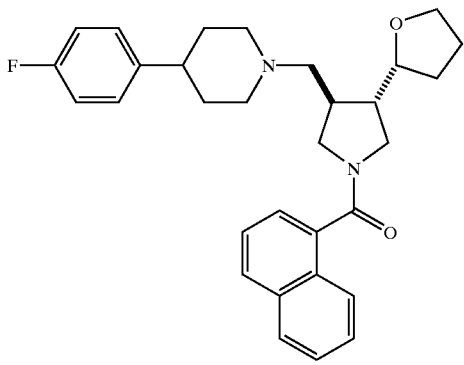

1-(1-Naphthoyl)-3-(RS)-4-(4-fluorophenyl) piperidinylmethyl)-4-(SR)-(tetrahydrofuran-2-yl) pyrrolidine Step 1. 1-(1-Naphthoyl)-3-(RS)-4-(4-fluorophenyl) piperidinylmethyl)-4-(SR)-(4-benzyloxy-1-hydroxy-n-but-1-yl)pyrrolidine

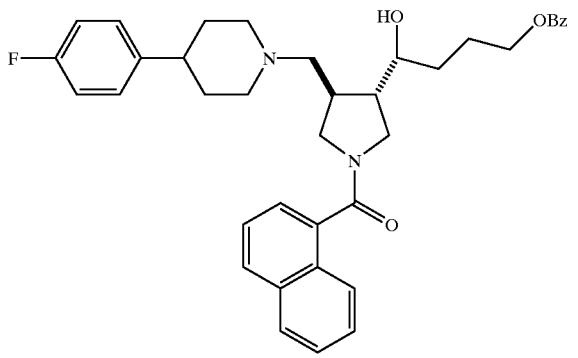

A mixture of 1 mL (5.67 mmol) of 3-benzyloxy-1-bromopropane and 0.19 g (7.9 mmol) of Mg in 4 mL of THF was stirred at 65° C. for 1 h. To this stirred reaction mixture was added a solution of 0.166 g (0.37 mmol) of 1-(1-naphthoyl)-3-(RS)-4-(4-fluorophenyl)piperidinylmethyl)-4-(SR)-(formyl)pyrrolidine in 2 mL of THF and the reaction mixture was stirred at rt for 1 h. The reaction mixture was diluted with ether and was washed with sat'd NaHCO$_3$ and NaCl solutions, dried over Na$_2$SO$_4$, filtered and the filtrate was concentrated. The residue was purified by chromatography (silica, hexanes: EtOAc: NH$_3$ (2N in CH$_3$OH) 10:10:1) to give 0.16 g of the title compound.

Step 2. 1-(1-Naphthoyl)-3-(RS)-4-(4-fluorophenyl) piperidinylmethyl)-4-(SR)-(1,4dihydroxy-n-but-1-yl) pyrrolidine

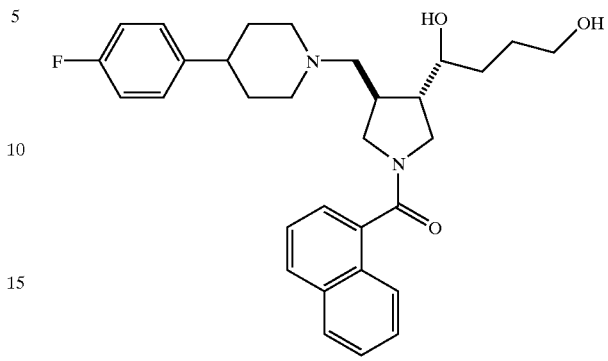

A mixture 0.1 g (0.17 mmol) of -(1-naphthoyl)-3-(RS)-4-(4-fluorophenyl)piperidinylmethyl)-4-(SR)-(4-benzyloxy-1-hydroxy-n-but-1-yl)pyrrolidine and 0.12 g of Pd/C (10%) in 8 mL of a 4.4% solution of HCO$_2$H in CH$_3$OH was heated at reflux for 2 h. The reaction mixture was filtered and the filtrate was concentrated. The residue was dissolved in CH$_2$Cl$_2$ and was washed with sat'd NaHCO$_3$ solution, dried over Na$_2$SO$_4$, filtered and the filtrate was concentrated. The title compound was used without further purification.

Step 3. 1-(1-Naphthoyl)-3-(RS)-4-(4-fluorophenyl) piperidinylmethyl)-4-(SR)-(tetrahydrofuran-2-yl) pyrrolidine A solution of 0.018 g (0.036 mmol) of 1-(1-naphthoyl)-3-(RS)-4-(4-fluorophenyl)piperidinylmethyl)-4-(SR)-(1,4dihydroxy-n-but-1-yl)pyrrolidine and 0.021 g (0.11 mmol) of p-toluenesulfonic acid in 4 mL of benzene was heated at reflux for 2 h. The reaction mixture was diluted with ether and was washed with sat'd NaHCO$_3$ and NaCl solutions, dried over Na$_2$SO$_4$, filtered and the filtrate was concentrated. The residue was purified by chromatography (silica, hexanes: EtOAc: NH$_3$ (2N in CH$_3$OH) 10:10:1) to give the title compound.

Mass Spectrum (CI) m/e 487 (M+1).

While the invention has been described and illustrated with reference to certain particular embodiments thereof, those skilled in the art will appreciate that various adaptions, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

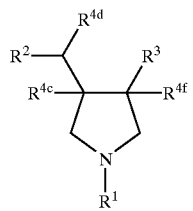

wherein:

$R^1$ is —X—$R^8$, wherein X is selected from the group consisting of:
(1) —$CH_2$—,
(2) —CO—,
(3) —$CH_2CH_2$—,
(4) —$CH_2CH_2CH_2$—, and
(5) —CH($C_{1-6}$ alkyl)-,
and wherein $R^8$ is selected from:
phenyl, naphthyl, biphenyl, fluorenyl, indenyl, indanyl, dihydronaphthyl, tetrahydronaphthyl, octahydronaphthyl, adamantyl, and heterocycle, which may be may be unsubstituted or substituted, where the substituents are independently selected from:
(a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
(A) phenyl, unsubstituted or substituted, wherein the substituents are independently selected from: halogen, hydroxy, $C_{1-6}$ alkyl, $C_{1-6}$ alkoxy, —$CO_2(C_{1-6}$ alkyl), —$NH_2$, —NH($C_{1-6}$ alkyl), —N($C_{1-6}$ alkyl)($C_{1-6}$ alkyl), and trifluoromethyl,
(B) naphthyl, unsubstituted or substituted, wherein the substituents are independently selected from: halogen, hydroxy, $C_{1-6}$ alkyl, $C_{1-6}$ alkoxy, —$CO_2(C_{1-6}$ alkyl), —$NH_2$, —NH($C_{1-6}$ alkyl), —N($C_{1-6}$ alkyl)($C_{1-6}$ alkyl), and trifluoromethyl,
(C) heterocycle, unsubstituted or substituted, wherein the substituents are independently selected from: halogen, hydroxy, $C_{1-6}$ alkyl, $C_{1-6}$ alkoxy, —$CO_2(C_{1-6}$ alkyl), —$NH_2$, —NH($C_{1-6}$ alkyl), —N($C_{1-6}$ alkyl)($C_{1-6}$ alkyl), and trifluoromethyl,
(D) hydroxy,
(E) —O($C_{1-6}$ alkyl),
(F) —$CO_2(C_{1-6}$ alkyl),
(G) —S(O)$_n$—($C_{1-6}$ alkyl), wherein n is an integer selected from 0, 1 and 2,
(H) halogen,
(I) —$NH_2$,
(J) —NH($C_{1-6}$ alkyl), and
(K) —N($C_{1-6}$ alkyl)($C_{1-6}$ alkyl), (iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9CO$—$NR^9R^{10}$,
(ix) —$S(O)_2$—$NR^9R^{10}$, wherein n is an integer selected from 0, 1 and 2,
(x) —$NR^9S(O)_2$—$R^{10}$,
(xi) —$NR^9S(O)_2$—$NR^9R^{10}$,
(xii) —$S(O)_n$—$R^9$,
(xiii) —$CF_3$,
(xiv) —$CHF_2$,
(xv) —$CH_2F$,
(xvi) —O—$R^9$,
(xvii) —O($C_{1-6}$ alkyl)-O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$,
(b) —O—$C_{1-6}$ alkyl, —O—$C_{2-6}$ alkenyl, —O—$C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$,
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9CO$—$NR^9R^{10}$,
(ix) —$S(O)_2$—$NR^9R^{10}$,
(x) —$NR^9S(O)_2$—$R^{10}$,
(xi) —$NR^9S(O)_2$—$NR^9R^{10}$,
(xii) —$S(O)_n$—$R^9$,
(xiii) —$CF_3$,
(xiv) —$CHF_2$,
(xv) —$CH_2F$,
(xvii) —O—$R^9$,
(xvii) —O($C_{1-6}$ alkyl)-O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$,
(c) —$NO_2$,
(d) hydroxy,
(e) halogen,
(f) —$NR^9R^{10}$,
(g) —$NR^9$—$COR^{10}$, (h) —NR⁹—CO₂R¹⁰,
(i) —CO—NR⁹R¹⁰,
(j) —OCO—NR⁹R¹⁰,
(k) —NR⁹CO—NR⁹R¹⁰,
(l) —S(O)₂—NR⁹R¹⁰,
(m) —NR⁹S(O)₂—R¹⁰,
(n) —NR⁹S(O)₂—NR⁹R¹⁰,
(o) —S(O)ₙ—R⁹,
(p) —CF₃,
(q) —CHF₂,
(r) —CH₂F,
(s) —OCO—R⁹,
(t) —OCO₂—R⁹, and
(u) —CO—R⁹;

R² is selected from the group consisting of:

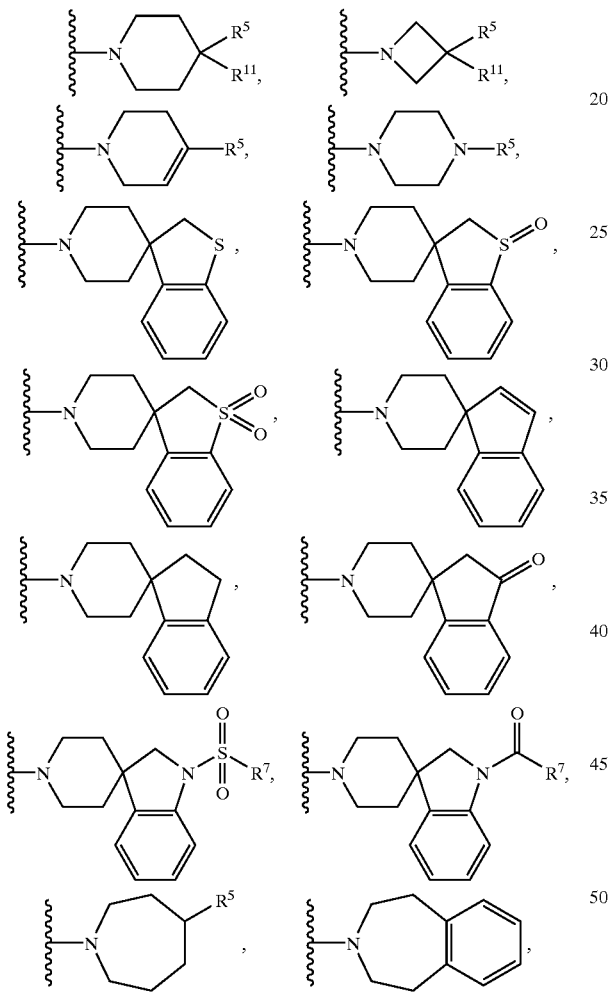

wherein R⁵ is selected from:
(1) —NR⁶CO—O—R⁷, wherein R⁶ is hydrogen, C₁₋₆ alkyl or C₁₋₆ alkyl-C₅₋₆ cycloalkyl, and R⁷ is C₁₋₆ alkyl, C₅₋₆ cycloalkyl, benzyl or phenyl, wherein the alkyl, cycloalkyl, benzyl or phenyl is unsubstituted or substituted with halogen, C₁₋₃ alkyl, C₁₋₃ alkoxy or trifluoromethyl,
(2) phenyl, which is unsubstituted or substituted with halogen, hydroxy, C₁₋₆ alkyl, C₁₋₆ alkoxy, —CO₂(C₁₋₆ alkyl), —NH₂, —NHR⁹, —NR⁹R¹⁰, or trifluoromethyl,
(3) -pyridyl,
(4) -thienyl,
(5) —C₁₋₆ alkyl-phenyl, —C₁₋₆ alkyl-naphthyl, —C₁₋₆ alkyl-indenyl, —C₁₋₆ alkyl-indanyl, and —C₁₋₆ alkyl-heterocycle, wherein the phenyl, naphthyl, indenyl, indanyl, or heterocycle is unsubstituted or substituted with: halogen, hydroxy, C₁₋₆ alkyl, C₁₋₆ alkoxy, —CO₂(C₁₋₆ alkyl), —NH₂, —NHR⁹, —NR⁹R¹⁰, or trifluoromethyl;
and wherein the —C₁₋₆ alkyl is optionally substituted with oxo, hydroxy, C₁₋₆ alkoxy, acetoxy, or halogen,
(6) —O—C₁₋₆ alkyl-phenyl, —O—C₁₋₆ alkyl-naphthyl, —O—C₁₋₆ alkyl-indenyl, —O—C₁₋₆ alkyl-indanyl, and —O—C₁₋₆ alkyl-heterocycle, wherein the phenyl, naphthyl, indenyl, indanyl, or heterocycle is unsubstituted or substituted with: halogen, hyroxy, C₁₋₆ alkyl, C₁₋₆ alkoxy, —CO₂(C₁₋₆ alkyl), —NH₂, NHR₉, —NR⁹R¹⁰, or trifluoromethyl,
(7) —C₁₋₄ alkyl-O—C₁₋₄ alkyl-phenyl, wherein the phenyl is unsubstituted or substituted with halogen, hydroxy, C₁₋₆ alkyl, C₁₋₆ alkoxy, —CO₂(C₁₋₆ alkyl), —NH₂, —NHR⁹, —NR⁹R¹⁰, or trifluoromethyl, and
(8) —C₁₋₄ alkyl-S(O)ₙ—C₁₋₄ alkyl-phenyl, wherein the phenyl is unsubstituted or substituted with halogen, hydroxy, C₁₋₆ alkyl, C₁₋₆ alkoxy, —CO₂(C₁₋₆ alkyl), —NH₂, —NHR⁹, —NR⁹R¹⁰, or trifluoromethyl;
and wherein R¹¹ is a selected from:
(1) -hydrogen,
(2) —OH,
(3) —C₁₋₆ alkyl, and
(4) -halogen;

R³ is selected from:
C₁₋₈ alkyl, C₂₋₈ alkenyl, and C₂₋₈ alkynyl, wherein the alkyl, alkenyl, or alkynyl is unsubstituted or substituted, wherein the substituents are independently selected from:
(a) halogen,
(b) hydroxy,
(c) —CO₂(C₁₋₆ alkyl),
(d) —OCO—R⁹,
(e) —OCO₂—R⁹,
(f) —CO—R⁹,
(g) phenyl or heterocycle, wherein the phenyl or heterocycle is unsubstituted or substituted, wherein the substituents are independently selected from: halogen, hydroxy, C₁₋₆ alkyl, C₁₋₆ alkoxy, —CO₂(C₁₋₆ alkyl), —NR⁹R¹⁰, and trifluoromethyl;
(h) —S(O)ₙ—R⁹,
(i) —NR⁹R¹⁰,
(j) —NR⁹—COR¹⁰,
(k) —NR⁹—CO₂R¹⁰,
(l) —CO—NR⁹R¹⁰,
(m) —OCO—NR⁹R¹⁰,
(n) —NR⁹CO—NR⁹R¹⁰,
(o) —S(O)₂—NR⁹R¹⁰,
(p) —NR⁹S(O)₂—R¹⁰,
(q) —NR⁹S(O)₂—NR⁹R¹⁰,
(r) —CF₃,
(s) —CHF₂,
(t) —CH₂F, and
(u) —O—R⁹;

R⁴ᶜ, R⁴ᵈ, and R⁴ᶠ are independently selected from the group consisting of:
(1) hydrogen, and
(2) C₁₋₆ alkyl;
and pharmaceutically acceptable salts thereof and individual diastereomers thereof.

2. A compound of the formula Ib:

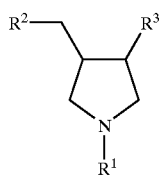

wherein:
$R^1$ is —X—$R^8$, wherein X is selected from the group consisting of:
(1) —$CH_2$—,
(2) —CO—, and
(3) —$CH_2CH_2$—,
and wherein $R^8$ is selected from:
phenyl, naphthyl, biphenyl, fluorenyl, indenyl, indanyl, dihydronaphthyl, tetrahydronaphthyl, octahydronaphthyl, adamantyl, and heterocycle, which may be unsubstituted or substituted, where the substituents are independently selected from:
(a) $C_{1-6}$ alkyl, $C_{2-6}$ alkenyl, $C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$, wherein $R^9$ and $R^{10}$ are independently selected from hydrogen, $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
(A) phenyl, unsubstituted or substituted, wherein the substituents are independently selected from: halogen, hydroxy, $C_{1-6}$ alkyl, $C_{1-6}$ alkoxy, —$CO_2(C_{1-6}$ alkyl), —$NH_2$, —NH($C_{1-6}$ alkyl), —N($C_{1-6}$ alkyl)($C_{1-6}$ alkyl), and trifluoromethyl,
(B) naphthyl, unsubstituted or substituted, wherein the substituents are independently selected from: halogen, hydroxy, $C_{1-6}$ alkyl, $C_{1-6}$ alkoxy, —$CO_2(C_{1-6}$ alkyl), —$NH_2$, —NH($C_{1-6}$ alkyl), —N($C_{1-6}$ alkyl)($C_{1-6}$ alkyl), and trifluoromethyl,
(C) heterocycle, unsubstituted or substituted, wherein the substituents are independently selected from: halogen, hydroxy, $C_{1-6}$ alkyl, $C_{1-6}$ alkoxy, —$CO_2(C_{1-6}$ alkyl), —$NH_2$, —NH($C_{1-6}$ alkyl), —N($C_{1-6}$ alkyl)($C_{1-6}$ alkyl), and trifluoromethyl,
(D) hydroxy,
(E) —O($C_{1-6}$ alkyl),
(F) —$CO_2(C_{1-6}$ alkyl),
(G) —$S(O)_n$—($C_{1-6}$ alkyl), wherein n is an integer selected from 0, 1 and 2,
(H) halogen,
(I) —$NH_2$,
(J) —NH($C_{1-6}$ alkyl), and
(K) —N($C_{1-6}$ alkyl)($C_{1-6}$ alkyl),
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9$CO—$NR^9R^{10}$,
(ix) —$S(O)_2$—$NR^9R^{10}$, wherein n is an integer selected from 0, 1 and 2,
(x) —$NR^9S(O)_2$—$R^{10}$,
(xi) —$NR^9S(O)_2$—$NR^9R^{10}$,
(xii) —$S(O)_n$—$R^9$,
(xiii) —$CF_3$,
(xiv) —$CHF_2$,
(xv) —$CH_2F$,
(xvi) —O—$R^9$,
(xvii) —O($C_{1-6}$ alkyl)-O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$,
(b) —O—$C_{1-6}$ alkyl, —O—$C_{2-6}$ alkenyl, —O—$C_{2-6}$ alkynyl, wherein the alkyl, alkenyl, or alkynyl is unsubstituted or substituted, wherein the substituents are independently selected from:
(i) hydroxy,
(ii) halogen,
(iii) —$NR^9R^{10}$,
(iv) —$NR^9$—$COR^{10}$,
(v) —$NR^9$—$CO_2R^{10}$,
(vi) —CO—$NR^9R^{10}$,
(vii) —OCO—$NR^9R^{10}$,
(viii) —$NR^9$CO—$NR^9R^{10}$,
(ix) —$S(O)_2$—$NR^9R^{10}$,
(x) —$NR^9S(O)_2$—$R^{10}$,
(xi) —$NR^9S(O)_2$—$NR^9R^{10}$,
(xii) —$S(O)_n$—$R^9$,
(xiii) —$CF_3$,
(xiv) —$CHF_2$,
(xv) —$CH_2F$,
(xvii) —O—$R^9$,
(xvii) —O($C_{1-6}$ alkyl)-O—$R^9$,
(xviii) phenyl,
(xix) naphthyl,
(xx) indenyl,
(xxi) indanyl,
(xxii) heterocycle,
(xxiii) —CO-phenyl,
(xxiv) —CO-naphthyl,
(xxv) —CO-indenyl,
(xxvi) —CO-indanyl,
(xxvii) —CO-heterocycle,
(xxviii) —OCO—$R^9$,
(xxix) —$OCO_2$—$R^9$, and
(xxx) —CO—$R^9$,
(c) —$NO_2$,
(d) hydroxy,
(e) halogen,
(f) —$NR^9R^{10}$,
(g) —$NR^9$—$COR^{10}$,
(h) —$NR^9$—$CO_2R^{10}$,
(i) —CO—$NR^9R^{10}$,
(j) —OCO—$NR^9R^{10}$,
(k) —$NR^9$CO—$NR^9R^{10}$,
(l) —$S(O)_2$—$NR^9R^{10}$, (m) —NR⁹S(O)₂—R¹⁰,
(n) —NR⁹S(O)₂—NR⁹R¹⁰,
(o) —S(O)ₙ—R⁹,
(p) —CF₃,
(q) —CHF₂,
(r) —CH₂F,
(s) —OCO—R⁹,
(t) —OCO₂—R⁹, and
(u) —CO—R⁹;

R² is:

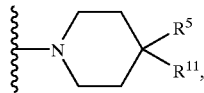

wherein R⁵ is selected from:
(1) —NR⁶CO—O—R⁷, wherein R⁶ is hydrogen, C₁₋₆ alkyl or C₁₋₆ alkyl-C₅₋₆ cycloalkyl, and R⁷ is C₁₋₆ alkyl, C₅₋₆ cycloalkyl, benzyl or phenyl, wherein the alkyl, cycloalkyl, benzyl or phenyl is unsubstituted or substituted with halogen, C₁₋₃ alkyl, C₁₋₃ alkoxy or trifluoromethyl,
(2) phenyl, which is unsubstituted or substituted with halogen, hydroxy, C₁₋₆ alkyl, C₁₋₆ alkoxy, —CO₂(C₁₋₆ alkyl), —NH₂, —NHR⁹, —NR⁹R¹⁰, or trifluoromethyl,
(3) -pyridyl,
(4) -thienyl,
(5) —C₁₋₆ alkyl-phenyl, —C₁₋₆ alkyl-naphthyl, —C₁₋₆ alkyl-indenyl, —C₁₋₆ alkyl-indanyl, and —C₁₋₆ alkyl-heterocycle, wherein the phenyl, naphthyl, indenyl, indanyl, or heterocycle is unsubstituted or substituted with: halogen, hydroxy, C₁₋₆ alkyl, C₁₋₆ alkoxy, —CO₂(C₁₋₆ alkyl), —NH₂, —NHR⁹, —NR⁹R¹⁰, or trifluoromethyl; and wherein the —C₁₋₆ alkyl is optionally substituted with oxo, hydroxy, C₁₋₆ alkoxy, acetoxy, or halogen,
(6) —O—C₁₋₆ alkyl-phenyl, —O—C₁₋₆ alkyl-naphthyl, —O—C₁₋₆ alkyl-indenyl, —O—C₁₋₆ alkyl-indanyl, and —O—C₁₋₆ alkyl-heterocycle, wherein the phenyl, naphthyl, indenyl, indanyl, or heterocycle is unsubstituted or substituted with: halogen, hyroxy, C₁₋₆ alkyl, C₁₋₆ alkoxy, —CO₂(C₁₋₆ alkyl), —NH₂, NHR₉, —NR⁹R¹⁰, or trifluoromethyl,
(7) —C₁₋₄ alkyl-O—C₁₋₄ alkyl-phenyl, wherein the phenyl is unsubstituted or substituted with halogen, hydroxy, C₁₋₆ alkyl, C₁₋₆ alkoxy, —CO₂(C₁₋₆ alkyl), —NH₂, —NHR⁹, —NR⁹R¹⁰, or trifluoromethyl, and
(8) —C₁₋₄ alkyl-S(O)ₙ—C₁₋₄ alkyl-phenyl, wherein the phenyl is unsubstituted or substituted with halogen, hydroxy, C₁₋₆ alkyl, C₁₋₆ alkoxy, —CO₂(C₁₋₆ alkyl), —NH₂, —NHR⁹, —NR⁹R¹⁰, or trifluoromethyl;
and wherein R¹¹ is a selected from:
(1) -hydrogen,
(2) —OH,
(3) —C₁₋₆ alkyl, and
(4) -halogen;
R³ is selected from:
C₁₋₈ alkyl, C₂₋₈ alkenyl, and C₂₋₈ alkynyl, wherein the alkyl, alkenyl, or alkynyl is unsubstituted or substituted, wherein the substituents are independently selected from:
(a) halogen,
(b) hydroxy,
(c) —CO₂(C₁₋₆ alkyl),
(d) —OCO—R⁹,
(e) —OCO₂—R⁹,
(f) —CO—R⁹,
(g) phenyl or heterocycle, wherein the phenyl or heterocycle is unsubstituted or substituted, wherein the substituents are independently selected from: halogen, hydroxy, C₁₋₆ alkyl, C₁₋₆ alkoxy, —CO₂(C₁₋₆ alkyl), —NR⁹R¹⁰, and trifluoromethyl;
(h) —S(O)ₙ—R⁹,
(i) —NR⁹R¹⁰,
(j) —NR⁹—COR¹⁰,
(k) —NR⁹—CO₂R¹⁰,
(l) —CO—NR⁹R¹⁰,
(m) —OCO—NR⁹R¹⁰,
(n) —NR⁹CO—NR⁹R¹⁰,
(o) —S(O)₂—NR⁹R¹⁰,
(p) —NR⁹S(O)₂—R¹⁰,
(q) —NR⁹S(O)₂—NR⁹R¹⁰,
(r) —CF₃,
(s) —CHF₂,
(t) —CH₂F, and
(u) —O—R⁹;
and pharmaceutically acceptable salts thereof and individual diastereomers thereof.

3. The compound of claim 2 of the formula Id:

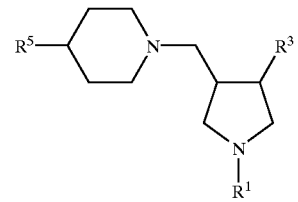

wherein:
R¹ is —X—R⁸, wherein X is selected from the group consisting of:
(1) —CH₂—, and
(2) —CO—, and wherein R⁸ is selected from: phenyl, naphthyl, indenyl, indanyl, indolyl, quinolyl, isoquinolyl, benzofuranyl, dihydrobenzofuranyl, methylenedioxybenzoyl, benzopyrazolyl, and benzotriazolyl, which may be unsubstituted or substituted, where the substituents are independently selected from:
(a) C₁₋₆ alkyl, C₂₋₆ alkenyl, C₂₋₆ alkynyl, wherein the alkyl, alkenyl, or alkynyl is unsubstituted or substituted, wherein the substituents are independently selected from:
(i) hydroxy,
(ii) halogen,
(iii) —NR⁹R¹⁰, wherein R⁹ and R¹⁰ are independently selected from hydrogen, C₁₋₆ alkyl, C₂₋₆ alkenyl, and C₂₋₆ alkynyl, wherein the alkyl, alkenyl, or alkynyl is unsubstituted or substituted, wherein the substituents are independently selected from:
(A) phenyl, unsubstituted or substituted, wherein the substituents are independently selected from: halogen, hydroxy, C₁₋₆ alkyl, C₁₋₆ alkoxy, —CO₂(C₁₋₆ alkyl), —NH₂, —NH(C₁₋₆ alkyl), —N(C₁₋₆ alkyl)(C₁₋₆ alkyl), and trifluoromethyl,
(B) naphthyl, unsubstituted or substituted, wherein the substituents are independently selected from: halogen, hydroxy, $C_{1-6}$ alkyl, $C_{1-6}$ alkoxy, $-CO_2(C_{1-6}$ alkyl), $-NH_2$, $-NH(C_{1-6}$ alkyl), $-N(C_{1-6}$ alkyl)($C_{1-6}$ alkyl), and trifluoromethyl,
- (C) heterocycle, unsubstituted or substituted, wherein the substituents are independently selected from: halogen, hydroxy, $C_{1-6}$ alkyl, $C_{1-6}$ alkoxy, $-CO_2(C_{1-6}$ alkyl), $-NH_2$, $-NH(C_{1-6}$ alkyl), $-N(C_{1-6}$ alkyl)($C_{1-6}$ alkyl), and trifluoromethyl,
- (D) hydroxy,
- (E) $-O(C_{1-6}$ alkyl),
- (F) $-CO_2(C_{1-6}$ alkyl),
- (G) $-S(O)_n-(C_{1-6}$ alkyl), wherein n is an integer selected from 0, 1 and 2,
- (H) halogen,
- (I) $-NH_2$,
- (J) $-NH(C_{1-6}$ alkyl), and
- (K) $-N(C_{1-6}$ alkyl)($C_{1-6}$ alkyl), (iv) $-NR^9-COR^{10}$,
(v) $-NR^9-CO_2R^{10}$,
(vi) $-CO-NR^9R^{10}$,
(vii) $-OCO-NR^9R^{10}$,
(viii) $-NR^9CO-NR^9R^{10}$,
(ix) $-S(O)_2-NR^9R^{10}$, wherein n is an integer selected from 0, 1 and 2,
(x) $-NR^9S(O)_2-R^{10}$,
(xi) $-NR^9S(O)_2-NR^9R^{10}$,
(xii) $-S(O)_n-R^9$,
(xiii) $-CF_3$,
(xiv) $-CHF_2$,
(xv) $-CH_2F$,
(xvi) $-O-R^9$,
(xvii) $-O(C_{1-6}$ alkyl)-O$-R^9$,
(xviii) phenyl,
(xix) naphthyl,
(xx) indenyl,
(xxi) indanyl,
(xxii) heterocycle,
(xxiii) $-CO$-phenyl,
(xxiv) $-CO$-naphthyl,
(xxv) $-CO$-indenyl,
(xxvi) $-CO$-indanyl,
(xxvii) $-CO$-heterocycle,
(xxviii) $-OCO-R^9$,
(xxix) $-OCO_2-R^9$, and
(xxx) $-CO-R^9$, (b) $-O-C_{1-6}$ alkyl, $-O-C_{2-6}$ alkenyl, $-O-C_{2-6}$ alkynyl, wherein the alkyl, alkenyl, or alkynyl is unsubstituted or substituted, wherein the substituents are independently selected from:
(i) hydroxy,
(ii) halogen,
(iii) $-NR^9R^{10}$,
(iv) $-NR^9-COR^{10}$,
(v) $-NR^9-CO_2R^{10}$,
(vi) $-CO-NR^9R^{10}$,
(vii) $-OCO-NR^9R^{10}$,
(viii) $-NR^9CO-NR^9R^{10}$,
(ix) $-S(O)_2-NR^9R^{10}$,
(x) $-NR^9S(O)_2-R^{10}$,
(xi) $-NR^9S(O)_2-NR^9R^{10}$,
(xii) $-S(O)_n-R^9$,
(xiii) $-CF_3$,
(xiv) $-CHF_2$,
(xv) $-CH_2F$,
(xvii) $-O-R^9$,
(xvii) $-O(C_{1-6}$ alkyl)-O$-R^9$,
(xviii) phenyl,
(xix) naphthyl,
(xx) indenyl,
(xxi) indanyl,
(xxii) heterocycle,
(xxiii) $-CO$-phenyl,
(xxiv) $-CO$-naphthyl,
(xxv) $-CO$-indenyl,
(xxvi) $-CO$-indanyl,
(xxvii) $-CO$-heterocycle,
(xxviii) $-OCO-R^9$,
(xxix) $-OCO_2-R^9$, and
(xxx) $-CO-R^9$, (c) $-NO_2$,
(d) hydroxy,
(e) halogen,
(f) $-NR^9R^{10}$,
(g) $-NR^9-COR^{10}$,
(h) $-NR^9-CO_2R^{10}$,
(i) $-CO-NR^9R^{10}$,
(j) $-OCO-NR^9R^{10}$,
(k) $-NR^9CO-NR^9R^{10}$,
(l) $-S(O)_2-NR^9R^{10}$,
(m) $-NR^9S(O)_2-R^{10}$,
(n) $-NR^9S(O)_2-NR^9R^{10}$,
(o) $-S(O)_n-R^9$,
(p) $-CF_3$,
(q) $-CHF_2$,
(r) $-CH_2F$,
(s) $-OCO-R^9$,
(t) $-OCO_2-R^9$, and
(u) $-CO-R^9$;

wherein $R^5$ is selected from:
- (1) phenyl, which is unsubstituted or substituted with halogen, hydroxy, $C_{1-6}$ alkyl, $C_{1-6}$ alkoxy, $-CO_2(C_{1-6}$ alkyl), $-NH_2$, $-NHR^9$, $-NR^9R^{10}$, or trifluoromethyl,
- (2) $-C_{1-6}$ alkyl-phenyl, $-C_{1-6}$ alkyl-naphthyl, $-C_{1-6}$ alkyl-indenyl, $-C_{1-6}$ alkyl-indanyl, and $-C_{1-6}$ alkyl-heterocycle, wherein the phenyl, naphthyl, indenyl, indanyl, or heterocycle is unsubstituted or substituted with: halogen, hydroxy, $C_{1-6}$ alkyl, $C_{1-6}$ alkoxy, $-CO_2(C_{1-6}$ alkyl), $-NH_2$, $-NHR^9$, $-NR^9R^{10}$, or trifluoromethyl; and wherein the $-C_{1-6}$ alkyl is optionally substituted with oxo, hydroxy, $C_{1-6}$ alkoxy, acetoxy, or halogen,
- (3) $-O-C_{1-6}$ alkyl-phenyl, $-O-C_{1-6}$ alkyl-naphthyl, $-O-C_{1-6}$ alkyl-indenyl, $-O-C_{1-6}$ alkyl-indanyl, and $-O-C_{1-6}$ alkyl-heterocycle, wherein the phenyl, naphthyl, indenyl, indanyl, or heterocycle is unsubstituted or substituted with: halogen, hyroxy, $C_{1-6}$ alkyl, $C_{1-6}$ alkoxy, $-CO_2(C_{1-6}$ alkyl), $-NH_2$, $NHR_9$, $-NR^9R^{10}$, or trifluoromethyl,
- (4) $-C_{1-4}$ alkyl-O$-C_{1-4}$ alkyl-phenyl, wherein the phenyl is unsubstituted or substituted with halogen, hydroxy, $C_{1-6}$ alkyl, $C_{1-6}$ alkoxy, $-CO_2(C_{1-6}$ alkyl), $-NH_2$, $-NHR^9$, $-NR^9R^{10}$, or trifluoromethyl, and
- (5) $-C_{1-4}$ alkyl-S(O)$_n$-$C_{1-4}$ alkyl-phenyl, wherein the phenyl is unsubstituted or substituted with halogen, hydroxy, $C_{1-6}$ alkyl, $C_{1-6}$ alkoxy, $-CO_2(C_{1-6}$ alkyl), $-NH_2$, $-NHR^9$, $-NR^9R^{10}$, or trifluoromethyl;

$R^3$ is selected from:
$C_{1-8}$ alkyl, $C_{2-8}$ alkenyl, and $C_{2-8}$ alkynyl, wherein the alkyl, alkenyl, or alkynyl is unsubstituted or substituted, wherein the substituents are independently selected from:

(a) halogen,
(b) hydroxy,
(c) —CO$_2$(C$_{1-6}$ alkyl),
(d) —OCO—R$^9$,
(e) —OCO$_2$—R$^9$,
(f) —CO—R$^9$,
(g) phenyl or heterocycle, wherein the phenyl or heterocycle is unsubstituted or substituted, wherein the substituents are independently selected from: halogen, hydroxy, C$_{1-6}$ alkyl, C$_{1-6}$ alkoxy, —CO$_2$(C$_{1-6}$ alkyl), —NR$^9$R$^{10}$, and trifluoromethyl;
(h) —S(O)$_n$—R$^9$,
(i) —NR$^9$R$^{10}$,
(j) —NR$^9$—COR$^{10}$,
(k) —NR$^9$—CO$_2$R$^{10}$,
(l) —CO—NR$^9$R$^{10}$,
(m) —OCO—NR$^9$R$^{10}$,
(n) —NR$^9$CO—NR$^9$R$^{10}$,
(o) —S(O)$_2$—NR$^9$R$^{10}$,
(p) —NR$^9$S(O)$_2$—R$^{10}$,
(q) —NR$^9$S(O)$_2$—NR$^9$R$^{10}$,
(r) —CF$_3$,
(s) —CHF$_2$,
(t) —CH$_2$F, and
(u) —O—R$^9$;

and pharmaceutically acceptable salts thereof and individual diastereomers thereof.

4. The compound of claim 1 wherein:
R$^1$ is selected from the group consisting of:
(1) —CH$_2$-phenyl,
(2) —CO-phenyl,
(3) —CH$_2$-(2,4-dichlorophenyl),
(4) —CO-(2,4-dichlorophenyl),
(5) —CH$_2$-(2-naphthyl),
(6) —CO-(1-naphthyl),
(7) —CH$_2$-indolyl, and
(8) —CO-indolyl.

5. The compound of claim 1 wherein:
R$^1$ is selected from the group consisting of:
(1) —CH$_2$-phenyl,
(2) —CO-phenyl,
(3) —CH$_2$-(2,4-dichlorophenyl),
(4) —CH$_2$-(7-indolyl), and
(5) —CO-(7-indolyl).

6. The compound of claim 1 wherein:
R$^2$ is:

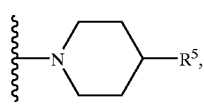

wherein R$^5$ is selected from:
(1) phenyl, which is unsubstituted or substituted with halogen, hydroxy, C$_{1-6}$alkyl, C$_{1-6}$alkoxy, or trifluoromethyl,
(2) —C$_{1-6}$alkyl-phenyl, wherein the phenyl is unsubstituted or substituted with: halogen, hydroxy, C$_{1-6}$alkyl, C$_{1-6}$alkoxy, or trifluoromethyl; and wherein the —C$_{1-6}$-alkyl is optionally substituted with oxo, hydroxy, C$_{1-6}$alkoxy, acetoxy, or halogen,
(3) —O—C$_{1-6}$alkyl-phenyl, wherein the phenyl is unsubstituted or substituted with halogen, hydroxy, C$_{1-6}$alkyl, C$_{1-6}$alkoxy, or trifluoromethyl,
(4) —C$_{1-4}$alkyl-O—C$_{1-4}$alkyl-phenyl, wherein the phenyl is unsubstituted or substituted with halogen, hydroxy, C$_{1-6}$alkyl, C$_{1-6}$alkoxy, or trifluoromethyl, and
(5) —C$_{1-4}$alkyl-S(O)$_n$—C$_{1-4}$alkyl-phenyl, wherein n is an integer selected from 0, 1 and 2, and wherein the phenyl is unsubstituted or substituted with halogen, hydroxy, C$_{1-6}$alkyl, C$_{1-6}$alkoxy, or trifluoromethyl.

7. The compound of claim 1 wherein:
R$^2$ is:

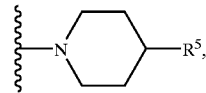

wherein R$^5$ is selected from:
(1) phenyl, which is unsubstituted or substituted with halogen, hydroxy, C$_{1-6}$alkyl, C$_{1-6}$alkoxy, or trifluoromethyl,
(2) —C$_{2-4}$alkyl-phenyl, wherein the phenyl is unsubstituted or substituted with chloro, fluoro, trifluoromethyl, methyl or ethyl and wherein the —C$_{2-4}$alkyl is optionally substituted with oxo, hydroxy, halogen, or methoxy,
(3) —C$_{1-3}$alkyl-O—C$_{1-3}$alkyl-phenyl, wherein the phenyl is unsubstituted or substituted with chloro, fluoro, trifluoromethyl, methyl or ethyl, and
(4) —C$_{1-3}$alkyl-S(O)$_n$—C$_{1-3}$alkyl-phenyl, wherein the phenyl is unsubstituted or substituted with chloro, fluoro, trifluoromethyl, methyl or ethyl.

8. The compound of claim 1 wherein:
R$^2$ is:

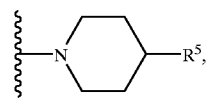

wherein R$^5$ is a selected from:
(1) phenyl, which is unsubstituted or substituted with halogen, hydroxy, C$_{1-6}$alkyl, C$_{1-6}$alkoxy, or trifluoromethyl,
(2) —C$_{3-4}$alkyl-phenyl, wherein the phenyl is unsubstituted or substituted with chloro, fluoro or methyl, and wherein the —C$_{3-4}$alkyl is optionally substituted with oxo, hydroxy, or methoxy,
(3) —C$_{1-3}$alkyl-O—C$_{1-3}$alkyl-phenyl, wherein the phenyl is unsubstituted or substituted with chloro, fluoro or methyl, and
(4) —C$_{1-3}$alkyl-S(O)$_n$—C$_{1-3}$alkyl-phenyl, wherein the phenyl is unsubstituted or substituted with chloro, fluoro or methyl.

9. The compound of claim 1 wherein:
R$^2$ is:

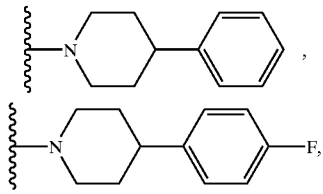

-continued

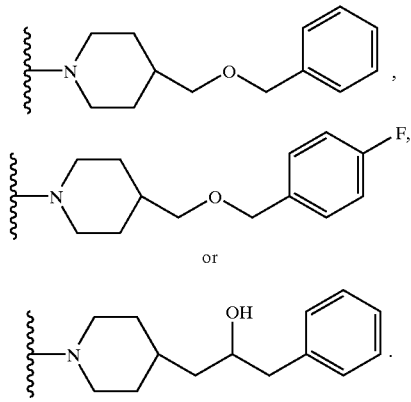

10. The compound of claim 1 wherein:
$R^3$ is selected from:
  $C_{1-8}$ alkyl, $C_{2-8}$ alkenyl, $C_{2-8}$ alkynyl, wherein the alkyl, alkenyl, or alkynyl is unsubstituted or substituted, wherein the substituents are independently selected from:
  (a) halogen,
  (b) hydroxy,
  (c) —$CO_2$($C_{1-6}$ alkyl),
  (d) —OCO—$R^9$,
  (e) —$OCO_2$—$R^9$,
  (f) —CO—$R^9$,
  (g) phenyl, wherein the phenyl is unsubstituted or substituted with: halogen, hydroxy, $C_{1-6}$alkyl, $C_{1-6}$alkoxy, —$CO_2$($C_{1-6}$ alkyl), —$NR^9R^{10}$, or trifluoromethyl;
  (h) —S(O)$_n$—$R^9$,
  (i) —$NR^9R^{10}$,
  (j) —$NR^9$—$COR^{10}$,
  (k) —$NR^9$—$CO_2R^{10}$,
  (l) —CO—$NR^9R^{10}$,
  (m) —OCO—$NR^9R^{10}$,
  (n) —$NR^9$CO—$NR^9R^{10}$,
  (o) —S(O)$_2$—$NR^9R^{10}$,
  (p) —$NR^9$S(O)$_2$—$R^{10}$,
  (q) —$NR^9$S(O)$_2$—$NR^9R^{10}$,
  (r) —$CF_3$,
  (s) —$CHF_2$, and
  (t) —$CH_2F$.

11. The compound of claim 1 wherein:
$R^3$ is selected from:
  $C_{1-6}$ alkyl, $C_{2-6}$ alkenyl, and $C_{2-6}$ alkynyl, wherein the alkyl, alkenyl, or alkynyl is unsubstituted or substituted, wherein the substituents are independently selected from:
  (a) halogen,
  (b) hydroxy,
  (c) —O—$C_{1-6}$ alkyl,
  (d) phenyl,
  (e) —O-phenyl,
  (f) —$CO_2$—$C_{1-6}$ alkyl, and
  (g) —$CF_3$.

12. The compound of claim 1 wherein:
$R^3$ is selected from:
  (1) —$C(CH_3)_3$,
  (2) —CH=$CH_2$,
  (3) —$CF_3$,
  (4) —$CH_2OH$,
  (5) —CH(OH)$CH_3$,
  (6) —C(OH)($CH_3$)$_2$,
  (7) —CH(OH)$CH_2CH_3$,
  (8) —CH(OH)CH=$CH_2$,
  (9) —CH(OH)$CH_2$CH=$CH_2$,
  (10) —CH(OH)C≡CH,
  (11) —CH(OH)phenyl,
  (12) —CH(OH)$CH_2$-phenyl,
  (13) —$CH_2$—O-phenyl,
  (14) —$CH_2$—O—$CH_3$,
  (15) —$CH_2$—O—$CH_2CH_3$,
  (16) —CH($CH_3$)—O—$CH_3$,
  (17) —CH(—O—$CH_3$)$_2$,
  (18) —CH(—O—$CH_2CH_3$)$_2$, and
  (19) —$CH_2NHCH_2$-phenyl.

13. The compound of claim 1 wherein:
$R^{4c}$, and $R^{4h}$ are each hydrogen and $R^{4d}$ is selected from the group consisting of hydrogen, and —$CH_3$.

14. The compound of claim 1 which is of the stereochemical configuration:

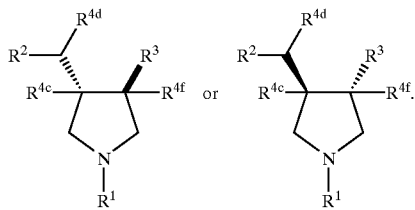

15. A compound which is selected from the group consisting of:
  1-(1-Naphthoyl)-3-(RS)-(4-(4-fluorophenyl)piperidinylmethyl)-4-(RS)-(t-butyl)pyrrolidine;
  1-(3,4-Dichlorobenzoyl)-3-(RS)-(4-(4-fluorophenyl)piperidinylmethyl)-4-(RS)-(t-butyl)pyrrolidine;
  1-(1-Naphthoyl)-3-(RS)-(4-(4-fluorophenyl)piperidinylmethyl)-4-(SR)-(vinyl)pyrrolidine;
  1-Benzyl-3-(RS)-(4-(4-fluorophenyl)piperidinylmethyl)-4-(SR)-(trifluoromethyl)pyrrolidine;
  1-(2-Naphthoyl)-3-(RS)-(4-(4-fluorophenyl)piperidinylmethyl)-4-(SR)-(trifluoromethyl)pyrrolidine;
  1-(7-Indolecarbonyl)-3-(RS)-(4-(4-fluorophenyl)piperidinylmethyl)-4-(SR)-(trifluoromethyl)pyrrolidine;
  1-(1-Methyl-7-indolecarbonyl)-3-(RS)-(4-(4-fluorophenyl)piperidinyl-methyl)-4-(SR)-(trifluoromethyl)pyrrolidine;
  1-(1-t-Butoxycarbonylmethyl)-7-indolecarbonyl)-3-(RS)-(4-(4-fluorophenyl)piperidinylmethyl)-4-(SR)-(trifluoromethyl)pyrrolidine;
  1-(1-Carboxymethyl)-7-indolecarbonyl)-3-(RS)-(4-(4-fluorophenyl)piperidinylmethyl)-4-(SR)-(trifluoromethyl)pyrrolidine;
  1-(1-Naphthoyl)-3-(RS)-(4-(4-fluorophenyl)piperidinylmethyl)-4-(RS)-(ethylaminomethyl)pyrrolidine;
  1-(1-Naphthoyl)-3-(RS)-(4-(4-fluorophenyl)piperidinylmethyl)-4-(RS)-(benzylaminomethyl)pyrrolidine;
  1-(1-Naphthoyl)-3-(RS)-(4-(4-fluorophenyl)piperidinylmethyl)-4-(RS)-(1-morpholinomethyl)pyrrolidine;

1-Benzyl-3-(RS)-(4-(4-fluorophenyl)piperidinylmethyl)-4-(SR)-hydroxymethylpyrrolidine;

1-(1-Naphthoyl)-3-(RS)-(4-(4-fluorophenyl)piperidinylmethyl)-4-(SR)-hydroxyethylpyrrolidine;

1-(1-Naphthoyl)-3-(RS)-(4-(4-fluorophenyl)piperidinylmethyl)-4-(SR)-(1-hydroxyethyl)pyrrolidine;

1-(1-Naphthoyl)-3-(RS)-(4-(4-fluorophenyl)piperidinylmethyl)-4-(SR)-(1-hydroxypropyl)pyrrolidine;

1-(1-Naphthoyl)-3-(RS)-(4-(4-fluorophenyl)piperidinylmethyl)-4-(SR)-(1-hydroxy-2-propenyl)pyrrolidine;

1-(1-Naphthoyl)-3-(RS)-(4-(4-fluorophenyl)piperidinylmethyl)-4-(SR)-(1-hydroxy-3-butenyl)pyrrolidine;

1-(1-Naphthoyl)-3-(RS)-(4-(4-fluorophenyl)piperidinylmethyl)-4-(SR)-(1-hydroxy-2-propynyl)pyrrolidine;

1-(1-Naphthoyl)-3-(RS)-(4-(4-fluorophenyl)piperidinylmethyl)-4-(SR)-(phenylhydroxymethyl)pyrrolidine;

1-(1-Naphthoyl)-3-(RS)-(4-(4-fluorophenyl)piperidinylmethyl)-4-(SR)-(2-phenyl-1-hydroxyethyl)pyrrolidine;

1-(1-Naphthoyl)-3-(RS)-(4-(4-fluorophenyl)piperidinylmethyl)-4-(SR)-(1-hydroxy-1-methylethyl)pyrrolidine;

1-(1-Methyl-7-indolecarbonyl)-3-(RS)-(4-(4-fluorophenyl)piperidinyl-methyl)-4-(SR)-(phenylhydroxymethyl)pyrrolidine;

1-Benzyl-3-(RS)-(4-(4-fluorophenyl)piperidinylmethyl)-4-(SR)-(phenylhydroxymethyl)pyrrolidine;

1-(1-Naphthoyl)-3-(RS)-(4-(4-fluorophenyl)piperidinylmethyl)-4-(SR)-(phenoxymethyl)pyrrolidine;

1-(1-Naphthoyl)-3-(RS)-(4-(4-fluorophenyl)piperidinylmethyl)-4-(S,R)-(ethoxymethyl)pyrrolidine;

1-(1-Naphthoyl)-3-(RS)-(4-(4-fluorophenyl)piperidinylmethyl)-4-(SR)-(methoxymethyl)pyrrolidine;

1-(1-Naphthoyl)-3-(RS)-(4-(4-fluorophenyl)piperidinylmethyl)-4-(SR)-(1-methoxyethyl)pyrrolidine;

1-(1-Naphthoyl)-3-(RS)-(4-(4-fluorophenyl)piperidinylmethyl)-4-(S,R)-(1,1-dimethoxymethyl)pyrrolidine;

1-(1-Naphthoyl)-3-(RS)-(4-(4-fluorophenyl)piperidinylmethyl)-4-(SR)-(1,1-diethoxymethyl)pyrrolidine;

1-(1-Naphthoyl)-3-(RS)-(4-(4-fluorophenyl)piperidinylmethyl)-4-(SR)-(1-acetoxyethyl)pyrrolidine;

1-(1-Naphthoyl)-3-(RS)-(4-(4-fluorophenyl)piperidinyl-methyl)-4-(SR)-(4-nitrophenoxycarbonyloxymethyl)-pyrrolidine;

1-(1-Naphthoyl)-3-(RS)-(4-(4-fluorophenyl)piperidinylmethyl)-4-(SR)-(N,N-diethylcarbamoyloxymethyl)pyrrolidine;

1-(1-Naphthoyl)-3-(RS)-(4-(4-fluorophenyl)piperidinylmethyl)-4-(SR)-(N-ethylcarbamoyloxymethyl)pyrrolidine;

and pharmaceutically acceptable salts thereof and individual diastereomers thereof.

16. A pharmaceutical composition which comprises an inert carrier and a compound of claim 1.

* * * * *